(12) United States Patent
Naughton et al.

(10) Patent No.: US 8,535,913 B2
(45) Date of Patent: *Sep. 17, 2013

(54) SOLUBLE COMPOSITION FOR PROMOTING HAIR GROWTH PRODUCED BY HYPOXIC CULTURE OF FIBROBLASTS CELLS

(75) Inventors: Gail K. Naughton, San Diego, CA (US); Frank Ziegler, Encinitas, CA (US); Mark Baumgartner, San Diego, CA (US); Kyle Nickey, Vista, CA (US)

(73) Assignee: Histogen, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/632,721

(22) Filed: Dec. 7, 2009

(65) Prior Publication Data

US 2010/0210530 A1 Aug. 19, 2010

Related U.S. Application Data

(63) Continuation-in-part of application No. 12/509,171, filed on Jul. 24, 2009, which is a continuation-in-part of application No. 12/501,312, filed on Jul. 10, 2009, now abandoned, which is a continuation-in-part of application No. 12/363,488, filed on Jan. 30, 2009, now Pat. No. 8,257,947.

(60) Provisional application No. 61/024,854, filed on Jan. 30, 2008, provisional application No. 61/034,361, filed on Mar. 6, 2008, provisional application No. 61/050,940, filed on May 6, 2008.

(51) Int. Cl.
*C12P 21/04* (2006.01)
*C12N 15/02* (2006.01)

(52) U.S. Cl.
USPC .......................... 435/70.3; 435/377; 435/395

(58) Field of Classification Search
None
See application file for complete search history.

(56) References Cited

U.S. PATENT DOCUMENTS

| | | | |
|---|---|---|---|
| 4,970,298 A | 11/1990 | Silver et al. |
| 5,032,508 A | 7/1991 | Naughton et al. |
| 5,091,173 A | 2/1992 | Buultjens et al. |
| 5,160,490 A | 11/1992 | Naughton et al. |
| 5,266,480 A | 11/1993 | Naughton et al. |
| 5,443,950 A | 8/1995 | Naughton et al. |
| 5,512,475 A | 4/1996 | Naughton et al. |
| 5,516,680 A | 5/1996 | Naughton et al. |
| 5,516,681 A | 5/1996 | Naughton et al. |
| 5,518,915 A | 5/1996 | Naughton et al. |
| 5,541,107 A | 7/1996 | Naughton et al. |
| 5,578,485 A | 11/1996 | Naughton et al. |
| 5,580,781 A | 12/1996 | Naughton et al. |
| 5,785,964 A | 7/1998 | Naughton et al. |
| 5,858,721 A | 1/1999 | Naughton et al. |
| 5,866,165 A | 2/1999 | Liu et al. |
| 5,888,551 A | 3/1999 | Jimenez et al. |
| 6,372,494 B1 | 4/2002 | Naughton et al. |
| 6,610,540 B1 | 8/2003 | Csete et al. |
| 6,733,776 B1 | 5/2004 | Li et al. |
| 6,924,141 B2 | 8/2005 | Morgan et al. |
| 7,118,746 B1 | 10/2006 | Naughton et al. |
| 7,175,842 B2 | 2/2007 | Morgan et al. |
| 2001/0005592 A1 | 6/2001 | Bhatnagar et al. |
| 2002/0114772 A1 | 8/2002 | Morgan et al. |
| 2002/0155440 A1 | 10/2002 | Ljubimova et al. |
| 2004/0005704 A1 | 1/2004 | Csete et al. |
| 2004/0076656 A1 | 4/2004 | Pavesio et al. |
| 2004/0142861 A1 | 7/2004 | Mansbridge |
| 2005/0032208 A1 | 2/2005 | Oh et al. |
| 2006/0036126 A1 | 2/2006 | Ross et al. |
| 2006/0115460 A1* | 6/2006 | Naughton ................. 424/93.21 |
| 2007/0077232 A1 | 4/2007 | Naughton et al. |
| 2007/0237750 A1 | 10/2007 | Naughton |
| 2011/0293526 A1 | 12/2011 | Plikus et al. |

FOREIGN PATENT DOCUMENTS

| | | |
|---|---|---|
| WO | WO 2005/104766 A2 | 11/2005 |
| WO | WO 2006/026617 A2 | 3/2006 |
| WO | WO 2006/026652 A2 | 3/2006 |
| WO | WO 2007/067618 A2 | 6/2007 |

OTHER PUBLICATIONS

Botcharev et al. Molecular Control of Epithelial-Mesenchymal Interactions During Hair Follicle Cycling Journal of Investigative Dermatology Symposium Proceedings, 2003, vol. 8, pp. 46-55.*
Dale, "Signal transduction by the Wnt family of ligands", *Biochem J.*, 329:209-223 (1998).
Huelsken et al., "Beta-Catenin Controls Hair Follicle Morphogenesis and Stem Cell Differentiation in Skin", *Cell Press*, 105:533-545, May 18, 2001.
Kishimoto et al., "Wnt signaling maintains the hair-inducing activity of the dermal papilla", *Genes & Development*, 11:1181-1185, 2000.
Yates and Glowacki, Gene expression changes in an in vitro model of chondroinduction: A comparison of two methods, *Wound Rep. Reg.*, 11:386-392, 2003.

(Continued)

*Primary Examiner* — Deborah Crouch
(74) *Attorney, Agent, or Firm* — DLA Piper LLP (US)

(57) ABSTRACT

The present invention is directed to a method of producing compositions including embryonic proteins. The method includes culturing cells under hypoxic conditions on a biocompatible three-dimensional surface in vitro. The culturing method produces both soluble and non-soluble fractions, which may be used separately or in combination to obtain physiologically acceptable compositions useful in a variety of medical and therapeutic applications.

17 Claims, 26 Drawing Sheets

(56) References Cited

OTHER PUBLICATIONS

Ito et al., "Wnt-dependent de novo hair follicle regeneration in adult mouse skin after wounding", Nature, 447(7142):316-320 (2007).
Horino et al., "Prolonged hypoxia accelerates the posttranscriptional process of collagen synthesis in cultured fibroblasts", *Life Sci.*, 71(26):3031-3045 (2002).
Kellar et al., "Hypoxic conditioned culture medium from fibroblasts grown under embryonic-like conditions supports healing following post-laser resurfacing", J. Cosmet. Dermatol., 8(3):190-196 (2009).
Levene et al., "The effect of hypoxia on the synthesis of collagen and glycosaminoglycans by cultured pig aortic endothelium", Atherosclerosis., 44(3):327-337 (1982).
Park et al., "Adipose-derived stem cells and their secretory factors as a promising therapy for skin aging", Dermatol. Surg., 34(10):1323-1326 (2008).
Pinney et al., "Wound Healing Potential of Dermagraft Conditioned Medium", J. Invest. Dermatol., 114(4):828 (2000).
Poulios et al., "Comparative effects of hypoxia on normal and immortalized human diploid fibroblasts", *Anticancer Res.*, 26(3A):2165-2168 (2006).
Rehman et al., "Secretion of angiogenic and antiapoptotic factors by human adipose stromal cells", Circulation, 109(10):1292-1298 (2004).
Wan et al., "Differential gene expression between juvenile and adult dura mater: a window into what genes play a role in the regeneration of membranous bone", Plast. Reconstr. Surg., 118(4):851-861 (2006).
Blanc et al., "Wnt-5a gene expression in malignant human neuroblasts", Cancer Lett., 228(1-2):117-123 (2005).
Kurayoshi et al., "Expression of Wnt-5a is correlated with aggressiveness of gastric cancer by stimulating cell migration and invasion", *Cancer Res.*, 66(21):10439-10448 (2006).
Murphy and Sambanis, "Effect of oxygen tension and alginate encapsulation on restoration of the differentiated phenotype of passaged chondrocytes", *Tissue Eng.*, 7(6):791-803 (2001).
O'Connell et al., "Assaying Wnt5A-mediated invasion in melanoma cells", *Methods Mol. Biol.*, 468:243-253 (2008).
Pukrop et al., "Wnt 5a signaling is critical for macrophage-induced invasion of breast cancer cell lines", *Proc. Natl. Acad. Sci. USA.*, 103(14):5454-5459 (2006).
Street et al., "Hypoxia regulates the paracrine coupling of angiogenesis and bone formation", *Eur. J. Orthop. Surg. Traumatol.*, 15(3):214-225 (2005).
Taki et al., "Down-regulation of Wnt-4 and up-regulation of Wnt-5a expression by epithelial-mesenchymal transition in human squamous carcinoma cells", *Cancer Sci.*, 94(7):593-597 (2003).
Weeraratna et al., "Wnt5a signaling directly affects cell motility and invasion of metastatic melanoma", *Cancer Cell.*, 1(3):279-288 (2002).
Zhuang et al., "Aberrant expression of growth factor Wnt-5A in six urinary malignant cell lines", Chin. Med. J. (Engl)., 112(3):251-255 (1999).
Zhuang et al., "Different Wnt-5A gene expressions in the renal cell carcinoma GRC-1 cell line during the cell cycle", *Chin. Med. J. (Engl).*, 113(4):306-309 (2000).
Guo et al., "Hypoxia induces the expression and secretion of connective tissue growth factor and fibronectin by cultured renal cortical myofibroblasts", *Beijing Da Xue Xue Bao.*, 39(1):67-71 (2007). Abstract only.
Siddiqui et al., "Differential effects of oxygen on human dermal fibroblasts: acute versus chronic hypoxia", *Wound Repair Regen.*, 4(2):211-8 (1996).
Fang et al., "Effects of Reg-2 on Survival of Spinal Cord Neurons In vitro", *The Anatomical Record: Advances in Integrative Anatomy and Evolutionary Biology*, vol. 293, No. 3, Jan. 20, 2010.
Nasu K et al., "Hypoxia simultaneously inhibits endostatin production and stimulates vascular endothelial growth factor production by cultured human endometrial stromal cells", *Fertility and Sterility, Elsevier Science Inc.*, vol. 82, No. 3, Sep. 1, 2004.
Sakaki et al., "Brief exposure to hypoxia induces bFGF mRNA and protein and protects rat cortical neurons from prolonged hypoxic stress", *Neuroscience Research* pp. 289-296, Jan. 1, 1995.
Zhang et al., Characteristics of 1-14 neural stem cells expanded in lowered oxygen and the potential role of hypoxia-inducible factor-1Alpha, *NeuroSignals*, pp. 259-265, Jan. 1, 2006.

\* cited by examiner

| 12 weeks | No perturbation | | Microdermabrasion | | Palomar | | RLLL | |
|---|---|---|---|---|---|---|---|---|
| | 109 | 126 | 109 | 126 | 109 | 126 | 109 | 126 |
| Hair Count | 0.036037* | 0.740274 | 0.630982 | | 0.261192 | 0.858779 | 0.261192 | 0.858779 |
| Density (n/cm²) | 0.036037* | 0.740274 | 0.630982 | | 0.261192 | 0.858779 | 0.261192 | 0.858779 |
| CumThickness (mm) | 0.041777* | 0.772055 | 0.77234 | | 0.473452 | 0.983672 | 0.473452 | 0.983672 |
| CumThicknessDensity (mm/cm²) | 0.041777* | 0.772055 | | | 0.473452 | 0.983672 | 0.473452 | 0.983672 |
| ThicknessMean (µm) | 0.285858 | 0.822739 | 0.914817 | | 0.680788 | 0.490353 | 0.680788 | 0.490353 |
| ThicknessMedian (µm) | 0.053416** | 0.801615 | 0.423532 | | 0.830499 | 0.183503*** | 0.830499 | 0.183503*** |
| DensityTerminal Hairs (n/cm²) | 0.031394* | 0.504405 | 0.998032 | | 0.840723 | 0.722296 | 0.840723 | 0.722296 |
| DensityVellus Hairs (m/cm²) | 0.899741 | 0.689657 | 0.458447 | | 0.411957 | 0.913446 | 0.411957 | 0.913446 |
| Anagen (%) | 0.910408 | | | | | | | |
| Telogen (%) | 0.749126 | | | | | | | |
| GrowthRate (mm/day) | 0.09524** | | | | | | | |

| 22 weeks | No perturbation | | Microdermabrasion | | Palomar | | RLLL | |
|---|---|---|---|---|---|---|---|---|
| | 109 | 126 | 109 | 126 | 109 | 126 | 109 | 126 |
| Hair Count | 0.178419*** | 0.740274 | 0.282805 | | 0.858779 | 0.124619*** | 0.19438*** | 0.124619*** |
| Density (n/cm$^2$) | 0.178419*** | 0.740274 | 0.282805 | | 0.858779 | 0.124619*** | 0.19438*** | 0.124619*** |
| CumThickness (mm) | 0.100193*** | 0.772055 | 0.280809 | | 0.983672 | 0.177552*** | 0.672424 | 0.177552*** |
| CumThicknessDensity (mm/cm$^2$) | 0.100193*** | 0.772055 | 0.280809 | | 0.983672 | 0.177552*** | 0.672424 | 0.177552*** |
| ThicknessMean (µm) | 0.048291* | 0.822739 | 0.707774 | | 0.490353 | 0.824491 | 0.807025 | 0.824491 |
| ThicknessMedian (µm) | 0.018761* | 0.801615 | 0.713708 | | 0.183503 | | 0.830499 | |
| DensityTerminal Hairs (n/cm$^2$) | 0.054341** | 0.504405 | 0.287598 | | 0.722296 | 0.287512 | 0.818073 | 0.287512 |
| DensityVellus Hairs (m/cm$^2$) | 0.47652 | 0.689657 | 0.295615 | | 0.913446 | 0.834836 | 0.779609 | 0.834836 |

SOLUBLE COMPOSITION FOR PROMOTING HAIR GROWTH PRODUCED BY HYPOXIC CULTURE OF FIBROBLASTS CELLS

CROSS REFERENCE TO RELATED APPLICATION(S)

This application is a continuation-in-part and claims the benefit of priority under 35 U.S.C. §120 of U.S. patent application Ser. No. 12/509,171, filed Jul. 24, 2009, currently pending, which is a continuation-in-part and claims the benefit of priority under 35 U.S.C. §120 of U.S. patent application Ser. No. 12/501,312, filed Jul. 10, 2009, currently pending, which is a continuation-in-part and claims the benefit of priority under 35 U.S.C. §120 of U.S. patent application Ser. No. 12/363,488, filed Jan. 30, 2009, currently pending, which claims the benefit of priority under 35 U.S.C. §119(e) of U.S. Ser. No. 61/024,854, filed Jan. 30, 2008; the benefit of priority under 35 U.S.C. §119(e) of U.S. Application Ser. No. 61/034,361, filed Mar. 6, 2008; and the benefit of priority under 35 U.S.C. §119(e) of U.S. Application Ser. No. 61/050,940, filed May 6, 2008. The disclosure of each of the prior applications is considered part of and is incorporated by reference in the disclosure of this application.

BACKGROUND OF THE INVENTION

1. Field of the Invention

The present invention relates generally to the production and use of extracellular matrix compositions and more specifically to proteins obtained by culturing cells under hypoxic conditions on a surface in a suitable growth medium.

2. Background Information

The extracellular matrix (ECM) is a complex structural entity surrounding and supporting cells that are found in vivo within mammalian tissues. The ECM is often referred to as the connective tissue. The ECM is primarily composed of three major classes of biomolecules including structural proteins such as collagens and elastins, specialized proteins such as fibrillins, fibronectins, and laminins, and proteoglycans.

Growth of ECM compositions in vitro and their use in a variety of therapeutic and medical applications have been described in the art. One therapeutic application of such ECM compositions includes treatment and repair of soft tissue and skin defects such as wrinkles and scars.

The repair or augmentation of soft tissue defects caused by defects, such as, acne, surgical scarring or aging has proven to be very difficult. A number of materials have been used to correct soft tissue defects with varying degrees of success, however, no material has been completely safe and effective. For example, silicon causes a variety of physiological and clinical problems including long term side effects, such as nodules, recurring cellulitis and skin ulcers.

Collagen compositions have also been used as an injectable material for soft tissue augmentation. Collagen is the main protein of connective tissue and the most abundant protein in mammals, making up about 25% of the total protein content. There are currently 28 types of collagen described in literature (see, e.g., Tables 1 and 2 infra, for a detailed listing). However, over 90% of the collagen in the body are Collagens I, II, III, and IV.

Different collagen materials have been used for treatment of soft tissue defects, such as reconstituted injectable bovine collagen, crosslinked collagen, or other xenogeneic collagens. However, several problems exist with such collagens. A common problem includes the complexity and high cost of producing the implant materials to remove potentially immunogenic substances to avoid allergic reactions in the subject. Additionally, treatments using such collagens have not proven long lasting.

Other materials have also been described that may be used for soft tissue repair or augmentation, such as, biocompatible ceramic particles in aqueous gels (U.S. Pat. No. 5,204,382), thermoplastic and/or thermosetting materials (U.S. Pat. No. 5,278,202), and lactic acid based polymer blends (U.S. Pat. No. 4,235,312). Additionally, use of naturally secreted ECM compositions have also been described (U.S. Pat. No. 6,284,284). However, such materials have all proven to have limitations.

Accordingly, new materials are needed for soft tissue repair and augmentation that overcome the deficiencies of prior materials. The need exists to provide a safe, injectable, long lasting, bioabsorbable, soft tissue repair and augmentation material.

In vitro cultured ECM compositions can additionally be used to treat damaged tissue, such as, damaged cardiac muscle and related tissue. The compositions are useful as implants or biological coatings on implantable devices, such as, stents; vascular prosthesis to promote vascularization in organs, such as the heart and related tissue; and devices useful in hernia repair, pelvic floor repair, wound repair, and rotator cuff repair, such as patches and the like.

Coronary heart disease (CHD), also called coronary artery disease (CAD), ischaemic heart disease, and atherosclerotic heart disease, is characterized by a narrowing of the small blood vessels that supply blood and oxygen to the heart. Coronary heart disease is usually caused by a condition called atherosclerosis, which occurs when fatty material and plaque builds up on the walls of arteries causing the arteries to narrow. As the coronary arteries narrow, blood flow to the heart can slow down or stop, causing chest pain (stable angina), shortness of breath, heart attack, and other symptoms.

Coronary heart disease (CHD) is the leading cause of death in the United States for men and women. According to the American Heart Association, more than 15 million people have some form of the condition. While the symptoms and signs of coronary heart disease are evident in the advanced state of the disease, most individuals with coronary heart disease show no evidence of disease for decades as the disease progresses before a sudden heart attack occurs. The disease is the most common cause of sudden death, and is also the most common reason for death of men and women over 20 years of age. According to present trends in the United States, half of healthy 40-year-old males will develop CHD in the future, as well as one in three healthy 40-year-old women.

Current methods for improving blood flow in a diseased or otherwise damaged heart involve invasive surgical techniques, such as, coronary by-pass surgery, angioplasty, and endarterectomy. Such procedures naturally involve high-degrees of inherent risk during and after surgery, and often only provide a temporary remedy to cardiac ischemia. Accordingly, new treatment options are required to increase the success of currently available techniques for treating CHD and related symptoms.

In vitro cultured ECM compositions can additionally be used to repair and/or regenerate damaged cells or tissue, such as chondral or osteochondral cells. Osteochondral tissue is any tissue that relates to or contains bone or cartilage. The compositions of the present invention are useful for treatment of osteochondral defects, such as degenerative connective tissue diseases, such as rheumatoid and/or osteoarthritis as well as defects in patients who have cartilage defects due to trauma.

Current attempts at repairing osteochondral defects include implantation of human chondrocytes in biocompatible and biodegradable hydrogel grafts in attempts to improve the possibilities to restore articular cartilage lesions. Additionally, the technique of chondrocyte culture in alginate beads or a matrix including polysulphated alginate has been described to generate a hyaline-like cartilagineous tissue. However, attempts at repairing enchondral lesions of articular cartilage by implantation of human autologous chondrocytes have had limited success. Accordingly, new treatment options are required to increase the success of currently available techniques for treating ostechondral defects.

In vitro cultured ECM compositions are also useful in tissue culture systems for generation of engineered tissue implants. The field of tissue engineering involves the use of cell culture technology to generate new biological tissues or repair damaged tissues. Fueled in part, by the stem cell revolution, tissue engineering technology offers the promise of tissue regeneration and replacement following trauma or treatment of degenerative diseases. It can also be used in the context of cosmetic procedures.

Tissue engineering techniques can be used to generate both autologous and heterologous tissue or cells using a variety of cell types and culture techniques. In creating an autologous implant, donor tissue may be harvested and dissociated into individual cells, and subsequently attached and cultured on a substrate to be implanted at the desired site of the functioning tissue. Many isolated cell types can be expanded in vitro using cell culture techniques, however, anchorage dependent cells require specific environments, often including the presence of a three-dimensional scaffold, to act as a template for growth.

Current tissue engineering technology provide generally, artificial implants. Successful cell transplantation therapy depends on the development of suitable substrates for both in vitro and in vivo tissue culture. Thus the development of an ECM that contains only natural materials and that is suitable for implantation would have more of the characteristics of the endogenous tissue. Accordingly, generation of natural ECM material is an ongoing challenge in the field of tissue engineering.

SUMMARY OF THE INVENTION

The present invention is based in part on the seminal discovery that cells cultured on surfaces (e.g., two-dimensional or three-dimensional) under conditions that stimulate the early embryonic environment (e.g., hypoxia and reduced gravitational forces) produce ECM compositions with fetal properties. The ECM compositions produced by culturing cells under hypoxic conditions on a surface containing one or more embryonic proteins have a variety of beneficial applications.

In one embodiment, the present invention provides a method of making ECM compositions containing one or more embryonic proteins. The method includes culturing cells under hypoxic conditions on a surface (e.g., two-dimensional or three-dimensional) in a suitable growth medium to produce a soluble and non-soluble fraction. In various aspects, the compositions include the soluble or non-soluble fraction separately, as well as combinations of the soluble and insoluble fraction. In various aspects, the compositions produced include upregulation of gene expression and production of laminins, collagens and Wnt factors. In other aspects the compositions produced include downregulation of gene expression of laminins, collagens and Wnt factors. In other aspects, the compositions are species specific and include cells and/or biological material from a single animal species.

While in vitro cultured ECM compositions are useful in the treatment of humans, such compositions may be applied to other species of animals. Accordingly, such compositions are well suited for veterinary applications.

In another embodiment, the present invention provides a method of producing a Wnt protein and a vascular endothelial growth factor (VEGF). The method includes culturing cells under hypoxic conditions on a surface (e.g., two-dimensional or three-dimensional) in a suitable growth medium, thereby producing the Wnt protein and the VEGF. In various aspects, the growth medium is serum-free and the hypoxic oxygen conditions are 1-5% oxygen. In related aspects, the Wnt species are upregulated as compared with media produced in oxygen conditions of about 15-20% oxygen. In an exemplary aspect, the Wnt species are wnt 7a and wnt 11.

In another embodiment, the present invention includes a method of repair and/or regeneration of cells by contacting cells to be repaired or regenerated with the ECM compositions described herein. In one aspect, the cells are osteochondral cells. Accordingly, the method contemplates repair of osteochondral defects.

In another embodiment, ECM compositions are useful as implants or biological coatings on implantable devices. In various aspects, the compositions of the present invention are included in implants or utilized as biological coatings on implantable devices, such as, stents; and vascular prosthesis to promote vascularization in organs, such as the heart and related tissue. In a related aspect, the compositions are included in tissue regeneration patches or implants, useful in hernia repair, pelvic floor repair, wound repair, rotator cuff repair, and the like.

In yet another embodiment the present invention includes a method for improvement of a skin surface in a subject including administering to the subject at the site of a wrinkle, the ECM compositions described herein. In yet a further embodiment, the present invention includes a method for soft tissue repair or augmentation in a subject including administering to the subject at the site of a wrinkle, the ECM compositions described herein.

In another embodiment, the present invention includes a tissue culture system. In various aspects, the culture system is composed of the ECM compositions described herein, such as being included in two-dimensional or three-dimensional support materials. In another aspect, the ECM compositions described herein serve as a support or two-dimensional or three-dimensional support for the growth of various cell types. For example, the culture system can be used to support the growth of stem cells. In one aspect, the stem cells are embryonic stem cells, mesenchymal stem cells or neuronal stem cells.

In another embodiment, the compositions of the present invention can be used to provide a surface coating used in association with implantation of a device in a subject to promote endothelialization and vascularization.

In another embodiment, the compositions of the present invention can be used to provide a method of treating damaged tissue. The method includes contacting the damaged tissue with a composition generated by culturing cells under hypoxic conditions on a two-dimensional or three-dimensional surface containing one or more embryonic proteins under conditions that allow for treatment of the damaged tissue.

In another embodiment, the present invention includes a biological vehicle for cell delivery or maintenance at a site of delivery including the ECM compositions described herein.

The vehicle can be used in such applications as injections of cells, such as stem cells, into damaged heart muscle or for tendon and ligament repair.

In another embodiment, the present invention provides a method for stimulating or promoting hair growth. The method includes contacting a cell with the ECM compositions described herein. In an exemplary aspect, the cell is a hair follicle cell. In various aspects the cell may be contacted in vivo or ex vivo.

BRIEF DESCRIPTION OF THE DRAWINGS

FIG. 1 shows graphical representations of FBGC formation 2 weeks after implantation of polypropylene mesh coated with hECM.

FIG. 2 shows graphical representations of FBGC formation 2 weeks after implantation of polypropylene mesh coated with hECM.

FIG. 3 shows pictorial representations of human hair follicle cells. FIG. 3A is an image of human hair follicle cells after cell culture for four weeks in the presence of hECM and subsequent transplantation into a mouse and growth for 4 additional weeks, while

FIG. 14 shows graphical representations of FBGC formation 2 weeks after implantation of polypropylene mesh coated with hECM.

FIG. 15 shows graphical representations of FBGC formation 5 weeks after implantation of polypropylene mesh coated with hECM.

FIG. 16 shows graphical representations of the mean fibrous capsule thicknesses determined 2 weeks after implantation of polypropylene mesh coated with hECM.

FIG. 17 shows graphical representations of the mean fibrous capsule thicknesses determined 5 weeks after implantation of polypropylene mesh coated with hECM.

FIG. 18 shows a graphical representation of a histogram showing hair growth characteristics after administration of hECM including wnt 7a.

FIG. 19 shows a tabular representation showing hair growth characteristics for 2 test subjects at 12 weeks after inception of a study testing the efficacy of administration of hECM including wnt 7a.

FIG. 20 shows a tabular representation showing hair growth characteristics for 2 test subjects at 22 weeks after inception of a study testing the efficacy of administration of hECM including wnt 7a.

FIG. 21 shows graphical representations of the aggregate results of control subjects as compared to treated subjects, neither including perturbation.

FIG. 22 shows graphical representations of the aggregate results of control subjects as compared to hECM treated subjects, neither including perturbation.

DETAILED DESCRIPTION OF THE INVENTION

Figure 1A:
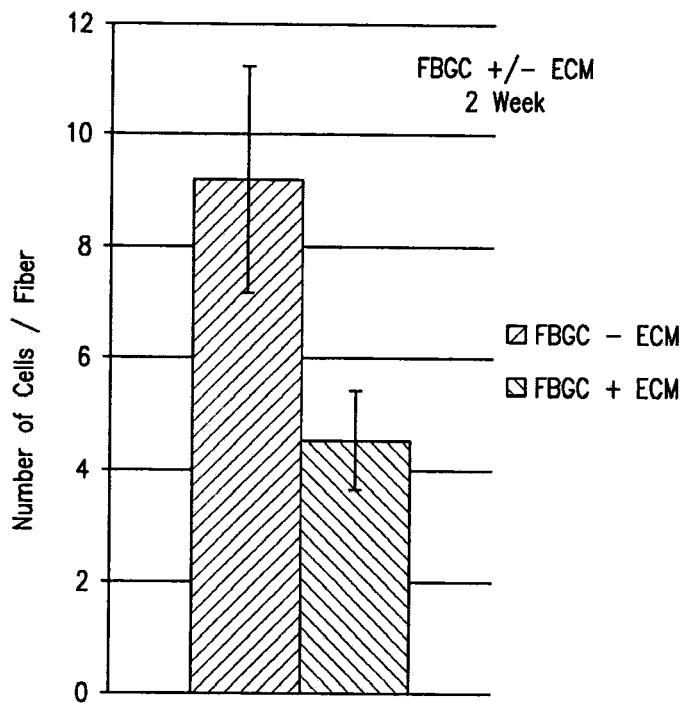
FIG. 1A shows the number of FBGCs per fiber 2 weeks after implantation for uncoated (first column) and hECM coated fibers (second column).

The present invention relates to a method for making ECM compositions that include one or more embryonic proteins. In particular the compositions are generated by culturing cells under hypoxic conditions on a surface (e.g., two-dimensional or three-dimensional) in a suitable growth medium. The culturing method produces both soluble and non-soluble fractions which may be used separately or in combination to obtain physiologically acceptable compositions having a variety of applications.

The compositions of the present invention have a variety of applications including, but not limited to, promoting repair and/or regeneration of damaged cells or tissues, use in patches and implants to promote tissue regeneration (e.g., hernial repair, pelvic floor repair, rotator cuff repair, and wound repair), use in tissue culture systems for culturing cells, such as stem cells, use in surface coatings used in association with implantable devices (e.g., pacemakers, stents, stent grafts, vascular prostheses, heart valves, shunts, drug delivery ports or catheters, hernial and pelvic floor repair patches), promoting soft tissue repair, augmentation, and/or improvement of a skin surface, such as wrinkles, use as a biological anti-adhesion agent or as a biological vehicle for cell delivery or maintenance at a site of delivery.

The invention is based in part, on the discovery that cells cultured on three-dimensional surfaces under conditions that stimulate the early embryonic environment (hypoxia and reduced gravitational forces) prior to angiogenesis produces ECM compositions with fetal properties, including generation of embryonic proteins. Growth of cells under hypoxic conditions demonstrate a unique ECM with fetal properties and growth factor expression. Unlike the culturing of ECM under traditional culture conditions, over 5000 genes are differentially expressed in ECM cultured under hypoxic conditions. This results in a cultured ECM that has different properties and a different biological composition. For example, an ECM produced under hypoxic conditions is similar to fetal mesenchymal tissue in that it is relatively rich in collagens type III, IV, and V, and glycoproteins such as fibronectin, SPARC, thrombospondin, and hyaluronic acid.

Hypoxia also enhances expression of factors which regulate wound healing and organogenesis, such as VEGF, FGF-7, and TGF-$\beta$, as well as multiple Wnt factors including wnts 2b, 4, 7a, 10a, and 11. Cultured embryonic human ECM also stimulates an increase of metabolic activity in human fibroblasts in vitro, as measured by increased enzymatic activity. Additionally, there is an increase in cell number in response to the cultured embryonic ECM.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

In various embodiments, the present invention involves methods for making ECM compositions that include one or more embryonic proteins and applications thereof. In particular the compositions are generated by culturing cells under hypoxic conditions on a two-dimensional or three-dimensional surface in a suitable growth medium. The compositions are derived by growing cells on a three-dimensional framework resulting in a multi-layer cell culture system. Cells grown on a three-dimensional framework support, in accordance with the present invention, grow in multiple layers, forming a cellular matrix. Growth of the cultured cells under hypoxic conditions results in differential gene expression as the result of hypoxic culturing conditions versus traditional culture.

ECM is a composition of proteins and biopolymers that substantially comprise tissue that is produced by cultivation of cells. Stromal cells, such as fibroblasts, are an anchorage dependant cell type requiring growth while attached to materials and surfaces suitable for cell culture. The ECM materials produced by the cultured cells are deposited in a three-dimensional arrangement providing spaces for the formation of tissue-like structures.

The cultivation materials providing three-dimensional architectures are referred to as scaffolds. Spaces for deposition of ECM are in the form of openings within, for example woven mesh or interstitial spaces created in a compacted configuration of spherical beads, called microcarriers.

As used herein, "extracellular matrix composition" includes both soluble and non-soluble fractions or any portion thereof. The non-soluble fraction includes those secreted ECM proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

The three-dimensional support or scaffold used to culture stromal cells may be of any material and/or shape that: (a) allows cells to attach to it (or can be modified to allow cells to attach to it); and (b) allows cells to grow in more than one layer (i.e., form a three dimensional tissue). In other embodiments, a substantially two-dimensional sheet or membrane or beads may be used to culture cells that are sufficiently three dimensional in form.

The biocompatible material is formed into a three-dimensional structure or scaffold, where the structure has interstitial spaces for attachment and growth of cells into a three dimensional tissue. The openings and/or interstitial spaces of the framework in some embodiments are of an appropriate size to allow the cells to stretch across the openings or spaces. Maintaining actively growing cells stretched across the framework appears to enhance production of the repertoire of growth factors responsible for the activities described herein. If the openings are too small, the cells may rapidly achieve confluence but be unable to easily exit from the mesh. These trapped cells may exhibit contact inhibition and cease production of the appropriate factors necessary to support proliferation and maintain long term cultures. If the openings are too large, the cells may be unable to stretch across the opening, which may lead to a decrease in stromal cell production of the appropriate factors necessary to support proliferation and maintain long term cultures. Typically, the interstitial spaces are at least about 100 um, at least 140 um, at least about 150 um, at least about 180 um, at least about 200 um, or at least about 220 um. When using a mesh type of matrix, as exemplified herein, we have found that openings ranging from about 100 μm to about 220 μm will work satisfactorily. However, depending upon the three-dimensional structure and intricacy of the framework, other sizes are permissible. Any shape or structure that allows the cells to stretch and continue to replicate and grow for lengthy time periods may function to elaborate the cellular factors in accordance with the methods herein.

In some aspects, the three dimensional framework is formed from polymers or threads that are braided, woven, knitted or otherwise arranged to form a framework, such as a mesh or fabric. The materials may also be formed by casting of the material or fabrication into a foam, matrix, or sponge-like scaffold. In other aspects, the three dimensional framework is in the form of matted fibers made by pressing polymers or other fibers together to generate a material with interstitial spaces. The three dimensional framework may take any form or geometry for the growth of cells in culture. Thus, other forms of the framework, as further described below, may suffice for generating the appropriate conditioned medium.

A number of different materials may be used to form the scaffold or framework. These materials include non-polymeric and polymeric materials. Polymers, when used, may be any type of polymer, such as homopolymers, random polymers, copolymers, block polymers, coblock polymers (e.g., di, tri, etc.), linear or branched polymers, and crosslinked or non-crosslinked polymers. Non-limiting examples of materials for use as scaffolds or frameworks include, among others, glass fibers, polyethylenes, polypropylenes, polyamides (e.g., nylon), polyesters (e.g., dacron), polystyrenes, polyacrylates, polyvinyl compounds (e.g., polyvinylchloride; PVC), polycarbonates, polytetrafluorethylenes (PTFE; TEFLON), thermanox (TPX), nitrocellulose, polysaacharides (e.g., celluloses, chitosan, agarose), polypeptides (e.g., silk, gelatin, collagen), polyglycolic acid (PGA), and dextran.

In some aspects, the framework or beads may be made of materials that degrade over time under the conditions of use. Biodegradable also refers to absorbability or degradation of a compound or composition when administered in vivo or under in vitro conditions. Biodegradation may occur through the action of biological agents, either directly or indirectly. Non-limiting examples of biodegradable materials include, among others, polylactide, polyglycolide, poly(trimethylene carbonate), poly(lactide-co-glycolide) (i.e., PLGA), polyethylene terephtalate (PET), polycaprolactone, catgut suture material, collagen (e.g., equine collagen foam), polylactic acid, or hyaluronic acid. For example, these materials may be woven into a three-dimensional framework such as a collagen sponge or collagen gel.

In other aspects, where the cultures are to be maintained for long periods of time, cryopreserved, and/or where additional structural integrity is desired, the three dimensional framework may be comprised of a nonbiodegradable material. As used herein, a nonbiodegradable material refers to a material that does not degrade or decompose significantly under the conditions in the culture medium. Exemplary nondegradable materials include, as non-limiting examples, nylon, dacron, polystyrene, polyacrylates, polyvinyls, polytetrafluoroethylenes (PTFE), expanded PTFE (ePTFE), and cellulose. An exemplary nondegrading three dimensional framework comprises a nylon mesh, available under the tradename Nitex®, a nylon filtration mesh having an average pore size of 140 μm and an average nylon fiber diameter of 90 μm (#3-210/36, Tetko, Inc., N.Y.).

In other aspects, the beads, scaffold or framework is a combination of biodegradeable and non-biodegradeable materials. The non-biodegradable material provides stability to the three dimensional scaffold during culturing while the biodegradeable material allows formation of interstitial spaces sufficient for generating cell networks that produce the cellular factors sufficient for therapeutic applications. The biodegradeable material may be coated onto the non-biodegradable material or woven, braided or formed into a mesh. Various combinations of biodegradable and non-biodegradable materials may be used. An exemplary combination is poly(ethylene therephtalate) (PET) fabrics coated with a thin biodegradable polymer film, poly[D-L-lactic-co-glycolic acid), in order to obtain a polar structure.

In various aspects, the scaffold or framework material may be pre-treated prior to inoculation with cells to enhance cell attachment. For example, prior to inoculation with cells, nylon screens in some embodiments are treated with 0.1 M acetic acid, and incubated in polylysine, fetal bovine serum, and/or collagen to coat the nylon. Polystyrene could be similarly treated using sulfuric acid. In other embodiments, the growth of cells in the presence of the three-dimensional support framework may be further enhanced by adding to the framework or coating it with proteins (e.g., collagens, elastin fibers, reticular fibers), glycoproteins, glycosaminoglycans (e.g., heparan sulfate, chondroitin-4-sulfate, chondroitin-6-sulfate, dermatan sulfate, keratan sulfate, etc.), fibronectins, and/or glycopolymer (poly[N-p-vinylbenzyl-D-lactoamide], PVLA) in order to improve cell attachment. Treatment of the scaffold or framework is useful where the material is a poor substrate for the attachment of cells.

In one aspect, mesh is used for production of ECM. The mesh is a woven nylon 6 material in a plain weave form with approximately 100 μm openings and approximately 125 μm thick. In culture, fibroblast cells attach to the nylon through charged protein interactions and grow into the voids of the mesh while producing and depositing ECM proteins. Mesh openings that are excessively large or small may not be effective but could differ from those above without substantially altering the ability to produce or deposit ECM. In another aspect, other woven materials are used for ECM production, such as polyolefin's, in weave configurations giving adequate geometry for cell growth and ECM deposition.

For example, nylon mesh is prepared for cultivation in any of the steps of the invention by cutting to the desired size, washing with 0.1-0.5M acetic acid followed by rinsing with high purity water and then steam sterilized. For use as a three-dimensional scaffold for ECM production the mesh is sized into squares approximately 10 cm×10 cm. However, the mesh could be any size appropriate to the intended application and may be used in any of the methods of the present invention, including cultivation methods for inoculation, cell growth and ECM production and preparation of the final form.

In other aspects, the scaffold for generating the cultured tissues is composed of microcarriers, which are beads or particles. The beads may be microscopic or macroscopic and may further be dimensioned so as to permit penetration into tissues or compacted to form a particular geometry. In some tissue penetrating embodiments, the framework for the cell cultures comprises particles that, in combination with the cells, form a three dimensional tissue. The cells attach to the particles and to each other to form a three dimensional tissue. The complex of the particles and cells is of sufficient size to be administered into tissues or organs, such as by injection or catheter. Beads or microcarriers are typically considered a two-dimensional system or scaffold.

As used herein, a "microcarriers" refers to a particle having size of nanometers to micrometers, where the particles may be any shape or geometry, being irregular, non-spherical, spherical, or ellipsoid.

The size of the microcarriers suitable for the purposes herein can be of any size suitable for the particular application. In some embodiments, the size of microcarriers suitable for the three dimensional tissues may be those administrable by injection. In some embodiments, the microcarriers have a particle size range of at least about 1 µm, at least about 10 µm, at least about 25 µm, at least about 50 µm, at least about 100 µm, at least about 200 µm, at least about 300 µm, at least about 400 µm, at least about 500 µm, at least about 600 µm, at least about 700 µm, at least about 800 µm, at least about 900 µm, at least about 1000 µm.

In some aspects in which the microcarriers are made of biodegradable materials. In some aspects, microcarriers comprising two or more layers of different biodegradable polymers may be used. In some embodiments, at least an outer first layer has biodegradable properties for forming the three dimensional tissues in culture, while at least a biodegradable inner second layer, with properties different from the first layer, is made to erode when administered into a tissue or organ.

In some aspects, the microcarriers are porous microcarriers. Porous microcarriers refer to microcarriers having interstices through which molecules may diffuse in or out from the microparticle. In other embodiments, the microcarriers are non-porous microcarriers. A nonporous microparticle refers to a microparticle in which molecules of a select size do not diffuse in or out of the microparticle.

Microcarriers for use in the compositions are biocompatible and have low or no toxicity to cells. Suitable microcarriers may be chosen depending on the tissue to be treated, type of damage to be treated, the length of treatment desired, longevity of the cell culture in vivo, and time required to form the three dimensional tissues. The microcarriers may comprise various polymers, natural or synthetic, charged (i.e., anionic or cationic) or uncharged, biodegradable, or nonbiodegradable. The polymers may be homopolymers, random copolymers, block copolymers, graft copolymers, and branched polymers.

In some aspects, the microcarriers comprise non-biodegradable microcarriers. Non-biodegradable microcapsules and microcarriers include, but not limited to, those made of polysulfones, poly(acrylonitrile-co-vinyl chloride), ethylene-vinyl acetate, hydroxyethylmethacrylate-methyl-methacrylate copolymers. These are useful to provide tissue bulking properties or in embodiments where the microcarriers are eliminated by the body.

In some aspects, the microcarriers comprise degradable scaffolds. These include microcarriers made from naturally occurring polymers, non-limiting example of which include, among others, fibrin, casein, serum albumin, collagen, gelatin, lecithin, chitosan, alginate or poly-amino acids such as poly-lysine. In other aspects, the degradable microcarriers are made of synthetic polymers, non-limiting examples of which include, among others, polylactide (PLA), polyglycolide (PGA), poly(lactide-co-glycolide) (PLGA), poly(caprolactone), polydioxanone trimethylene carbonate, polyhybroxyalkonates (e.g., poly(hydroxybutyrate), poly(ethyl glutamate), poly(DTH iminocarbony(bisphenol A iminocarbonate), poly(ortho ester), and polycyanoacrylates.

In some aspects, the microcarriers comprise hydrogels, which are typically hydrophilic polymer networks filled with water. Hydrogels have the advantage of selective trigger of polymer swelling. Depending on the composition of the polymer network, swelling of the microparticle may be triggered by a variety of stimuli, including pH, ionic strength, thermal, electrical, ultrasound, and enzyme activities. Non-limiting examples of polymers useful in hydrogel compositions include, among others, those formed from polymers of poly(lactide-co-glycolide); poly(N-isopropylacrylamide); poly(methacrylic acid-g-polyethylene glycol); polyacrylic acid and poly(oxypropylene-co-oxyethylene) glycol; and natural compounds such as chrondroitan sulfate, chitosan, gelatin, fibringogen, or mixtures of synthetic and natural polymers, for example chitosan-poly(ethylene oxide). The polymers may be crosslinked reversibly or irreversibly to form gels adaptable for forming three dimensional tissues.

In exemplary aspects, the microcarriers or beads for use in the present invention are composed wholly or composed partly of dextran.

In accordance with the present invention the culturing method is applicable to proliferation of different types of cells, including stromal cells, such as fibroblasts, and particularly primary human neonatal foreskin fibroblasts. In various aspects, the cells inoculated onto the scaffold or framework can be stromal cells comprising fibroblasts, with or without other cells, as further described below. In some embodiments, the cells are stromal cells that are typically derived from connective tissue, including, but not limited to: (1) bone; (2) loose connective tissue, including collagen and elastin; (3) the fibrous connective tissue that forms ligaments and tendons, (4) cartilage; (5) the ECM of blood; (6) adipose tissue, which comprises adipocytes; and (7) fibroblasts.

Stromal cells can be derived from various tissues or organs, such as skin, heart, blood vessels, bone marrow, skeletal muscle, liver, pancreas, brain, foreskin, which can be obtained by biopsy (where appropriate) or upon autopsy. In one aspect, fetal fibroblasts can be obtained in high quantity from foreskin, such as neonatal foreskins.

In some aspects, the cells comprise fibroblasts, which can be from a fetal, neonatal, adult origin, or a combination thereof. In some aspects, the stromal cells comprise fetal fibroblasts, which can support the growth of a variety of different cells and/or tissues. As used herein, a fetal fibroblast refers to fibroblasts derived from fetal sources. As used herein, neonatal fibroblast refers to fibroblasts derived from newborn sources. Under appropriate conditions, fibroblasts can give rise to other cells, such as bone cells, fat cells, and smooth muscle cells and other cells of mesodermal origin. In some embodiments, the fibroblasts comprise dermal fibroblasts, which are fibroblasts derived from skin. Normal human dermal fibroblasts can be isolated from neonatal foreskin. These cells are typically cryopreserved at the end of the primary culture.

In other aspects, the three-dimensional tissue can be made using stem or progenitor cells, either alone, or in combination with any of the cell types discussed herein. Stem and progenitor cells include, by way of example and not limitation, embryonic stem cells, hematopoietic stem cells, neuronal stem cells, epidermal stem cells, and mesenchymal stem cells.

In some embodiments, a "specific" three-dimensional tissue can be prepared by inoculating the three-dimensional scaffold with cells derived from a particular organ, i.e., skin, heart, and/or from a particular individual who is later to receive the cells and/or tissues grown in culture in accordance with the methods described herein.

For certain uses in vivo it is preferable to obtain the stromal cells from the patient's own tissues. The growth of cells in the presence of the three-dimensional stromal support framework can be further enhanced by adding to the framework, or coating the framework support with proteins, e.g., collagens, laminins, elastic fibers, reticular fibers, glycoproteins; glycosaminoglycans, e.g., heparin sulfate, chondroitin-4-sulfate, chondroitin-6-sulfate, dermatan sulfate, keratan sulfate, etc.; a cellular matrix, and/or other materials.

Thus, since the two-dimensional or three-dimensional culture systems described herein are suitable for growth of diverse cell types and tissues, and depending upon the tissue to be cultured and the collagen types desired, the appropriate stromal cells may be selected to inoculate the framework.

While the methods and applications of the present invention are suitable for use with different cell types, such as tissue specific cells or different types of stromal cells as discussed herein, derivation of the cells for use with the present invention may also be species specific. Accordingly, ECM compositions may be generated that are species specific. For example, the cells for use in the present invention may include human cells. For example, the cells may be human fibroblasts. Likewise, the cells are from another species of animal, such as equine (horse), canine (dog) or feline (cat) cells. Additionally, cells from one species or strain of species may be used to generate ECM compositions for use in other species or related strains (e.g., allogeneic, syngeneic and xenogeneic). It is also to be appreciated that cells derived from various species may be combined to generate multi-species ECM compositions.

Accordingly, the methods and compositions of the present invention are suitable in applications involving non-human animals. As used herein, "veterinary" refers to the medical science concerned or connected with the medical or surgical treatment of animals, especially domestic animals. Common veterinary animals may include mammals, amphibians, avians, reptiles and fishes. For example, typical mammals may include dogs, cats, horses, rabbits, primates, rodents, and farm animals, such as cows, horses, goats, sheep, and pigs.

As discussed above, additional cells may be present in the culture with the stromal cells. These additional cells may have a number of beneficial effects, including, among others, supporting long term growth in culture, enhancing synthesis of growth factors, and promoting attachment of cells to the scaffold. Additional cell types include as non-limiting examples, smooth muscle cells, cardiac muscle cells, endothelial cells, skeletal muscle cells, endothelial cells, pericytes, macrophages, monocytes, and adipocytes. Such cells may be inoculated onto the framework along with fibroblasts, or in some aspects, in the absence of fibroblasts. These stromal cells may be derived from appropriate tissues or organs, including, by way of example and not limitation, skin, heart, blood vessels, bone marrow, skeletal muscle, liver, pancreas, and brain. In other aspects, one or more other cell types, excluding fibroblasts, are inoculated onto the scaffold. In still other aspects, the scaffolds are inoculated only with fibroblast cells.

Fibroblasts may be readily isolated by disaggregating an appropriate organ or tissue which is to serve as the source of the fibroblasts. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, hyaluronidase, DNase, pronase, and/or dispase etc. Mechanical disruption can also be accomplished by a number of methods including, but not limited to the use of grinders, blenders, sieves, homogenizers, pressure cells, or insonators to name but a few. In one aspect, excised foreskin tissue is treated using digestive enzymes, typically collagenase and/or trypsinase to disassociate the cells from encapsulating structures.

The isolation of fibroblasts, for example, can be carried out as follows: fresh tissue samples are thoroughly washed and minced in Hanks' balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional framework, see Naughton et al., 1987, J. Med. 18 (3&4):219-250. Inoculation of the three-dimensional framework with a high concentration of stromal cells, e.g., approximately $10^6$ to $5 \times 10^7$ cells/ml, will result in the establishment of the three-dimensional stromal support in shorter periods of time.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168.

In one aspect, isolated fibroblast cells can be grown to produce cell banks. Cell banks are created to allow for initiating various quantities and timing of cultivation batches and to allow preemptive testing of cells for contaminants and specific cellular characteristics. Fibroblasts from the cell banks are subsequently grown to increase cell number to appropriate levels for seeding scaffolds. Operations involving environmental exposure of cells and cell contacting materials are performed by aseptic practices to reduce the potential for contamination of foreign materials or undesirable microbes.

In another aspect of the invention, after isolation, cells can be grown through several passages to a quantity suitable for building master cell banks. The cell banks can then be, harvested and filled into appropriate vessels and preserved in cryogenic conditions. Cells in frozen vials from master cell banks can be thawed and grown through additional passages (usually two or more). The cells can then be used to prepare cryogenically preserved working cell banks.

A cell expansion step uses vials of cells at the working cell bank stage to further increase cell numbers for inoculating three-dimensional scaffolds or supports, such as mesh or microcarriers. Each passage is a series of sub-culture steps that include inoculating cell growth surfaces, incubation, feeding the cells and harvesting.

Cultivation for cell banks and cell expansion can be conducted by inoculating culture vessels, such as culture flasks, roller bottles or microcarriers. Stromal cells, such as fibroblasts, attach to the intended growth surfaces and grow in the presence of culture media. Culture vessels, such as culture flasks, roller bottles and microcarriers are specifically configured for cell culture and are commonly made from various plastic materials qualified for intended applications. Microcarriers typically are microscopic or macroscopic beads and are typically made of various plastic materials. However, they can be made from other materials such as glasses or solid/semi-solid biologically based materials such as collagens or other materials such as Dextran, a modified sugar complex as discussed above.

During cultivation, expended media is periodically replaced with fresh media during the course of cell growth to maintain adequate availability of nutrients and removal of inhibitory products of cultivation. Culture flasks and roller bottles provide a surface for the cells to grow onto and are typically used for cultivation of anchorage dependent cells.

In one aspect, incubation is performed in a chamber heated at 37° C. Cultivation topologies requiring communication of media and the chamber environment use a 5% $CO_2$ v/v with air in the chamber gas space to aid in regulation of pH. Alternately, vessels equipped to maintain cultivation temperature and pH can be used for both cell expansion and ECM production operations. Temperatures below 35° C. or above 38° C. and $CO_2$ concentrations below 3% or above 12% may not be appropriate.

Harvesting cells from attachment surfaces can conducted by removal of growth media and rinsing the cells with a buffered salt solution to reduce enzyme competing protein, application of disassociating enzymes then neutralization of the enzymes after cell detachment. Harvested cell suspension is collected and harvest fluids are separated by centrifugation. Cell suspensions from sub-culture harvests can be sampled to assess the quantity of cells recovered and other cellular attributes and are subsequently combined with fresh media and applied as inoculums. The number of passages used for preparing cell banks and scaffold inoculum is critical with regard to achieving acceptable ECM characteristics.

After an appropriate three-dimensional scaffold is prepared, it is inoculated by seeding with the prepared stromal cells. Inoculation of the scaffold may be done in a variety of ways, such as sedimentation. Mesh prepared for culture of ECM under aerobic conditions are prepared in the same manner as for hypoxic grown mesh with the exception that an anaerobic chamber is not used to create hypoxic conditions.

For example, for both mesh prepared for culture of ECM under both aerobic and hypoxic conditions, prepared and sterilized mesh is placed in sterile 150 mm diameter×15 mm deep petri dishes and stacked to a thickness of approximately 10 pieces. Stacks of mesh are then inoculated by sedimentation. Cells are added to fresh media to obtain the appropriate concentration of cells for inoculum. Inoculum is added to the stack of mesh where cells settle onto the nylon fibers and attach while in incubated conditions. After an adequate time, individually seeded mesh sheets can be aseptically separated from the stack and placed individually into separate 150 mm×15 mm petri dishes containing approximately 50 ml of growth media.

Incubation of the inoculated culture is performed under hypoxic conditions, which is discovered to produce an ECM and surrounding media with unique properties as compared to ECM generated under normal culture conditions. As used herein, hypoxic conditions are characterized by a lower oxygen concentration as compared to the oxygen concentration of ambient air (approximately 15%-20% oxygen). In one aspect, hypoxic conditions are characterized by an oxygen concentration less than about 10%. In another aspect hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%. In a certain aspect, the system maintains about 1-3% oxygen within the culture vessel. Hypoxic conditions can be created and maintained by using a culture apparatus that allows one to control ambient gas concentrations, for example, an anaerobic chamber.

Incubation of cell cultures is typically performed in normal atmosphere with 15-20% oxygen and 5% $CO_2$ for expansion and seeding, at which point low oxygen cultures are split to an airtight chamber that is flooded with 95% nitrogen/5% $CO_2$ so that a hypoxic environment is created within the culture medium.

For example, petri dishes with mesh cultured for producing ECM under hypoxic conditions are initially grown in incubation at 37° C. and 95% air/5% $CO_2$ for 2-3 weeks. Following the period of near atmospheric cultivation, the petri dishes of mesh are incubated in a chamber designed for anaerobic cultivation that is purged with a gas mixture of approximately 95% nitrogen and 5% $CO_2$. Expended growth media is replaced with fresh media at atmospheric oxygen level through the culture period and after media is exchanged the mesh filled petri dishes are place in the anaerobic chamber, the chamber is purged with 95% nitrogen/5% $CO_2$ then incubated at 37° C. Cultured mesh are harvested when they reach the desired size or contain the desire biological components.

During the incubation period, the stromal cells will grow linearly along and envelop the three-dimensional framework before beginning to grow into the openings of the framework. The growing cells produce a myriad of growth factors, regulatory factors and proteins, some of which are secreted in the surrounding media, and others that are deposited on the support to make up the ECM more fully discussed below. Growth and regulatory factors can be added to the culture, but are not necessary. Culture of the stromal cells produces both non-soluble and soluble fractions. The cells are grown to an appropriate degree to allow for adequate deposition of ECM proteins.

During culturing of the three-dimensional tissues, proliferating cells may be released from the framework and stick to the walls of the culture vessel where they may continue to proliferate and form a confluent monolayer. To minimize this occurrence, which may affect the growth of cells, released cells may be removed during feeding or by transferring the three-dimensional cell culture to a new culture vessel. Removal of the confluent monolayer or transfer of the cultured tissue to fresh media in a new vessel maintains or restores proliferative activity of the three-dimensional cultures. In some aspects, removal or transfers may be done in a culture vessel which has a monolayer of cultured cells exceeding 25% confluency. Alternatively, the culture in some embodiments is agitated to prevent the released cells from sticking; in others, fresh media is infused continuously through the system. In some aspects, two or more cell types can be cultured together either at the same time or one first followed by the second (e.g., fibroblasts and smooth muscle cells or endothelial cells).

After inoculation of the three dimensional scaffolds, the cell culture is incubated in an appropriate nutrient medium and incubation conditions that supports growth of cells into the three dimensional tissues. Many commercially available media such as Dulbecco's Modified Eagles Medium (DMEM), RPMI 1640, Fisher's, Iscove's, and McCoy's, may be suitable for supporting the growth of the cell cultures. The medium may be supplemented with additional salts, carbon sources, amino acids, serum and serum components, vitamins, minerals, reducing agents, buffering agents, lipids, nucleosides, antibiotics, attachment factors, and growth factors. Formulations for different types of culture media are described in various reference works available to the skilled artisan (e.g., Methods for Preparation of Media, Supplements and Substrates for Serum Free Animal Cell Cultures, Alan R. Liss, New York (1984); Tissue Culture: Laboratory Procedures, John Wiley & Sons, Chichester, England (1996); Culture of Animal Cells, A Manual of Basic Techniques, 4 th Ed., Wiley-Liss (2000)).

The growth or culture media used in any of the culturing steps of the present invention, whether under aerobic or hypoxic conditions, may include serum, or be serum free. In one aspect, the media is Dulbecco's Modified Eagle Medium with 4.5 g/L glucose, alanyl-L-glutamine, Eq 2 mM, and nominally supplemented with 10% fetal bovine serum. In another aspect, the media is a serum free media and is Dulbecco's Modified Eagle Medium with 4.5 g/L glucose base medium with Glutamax®, supplemented with 0.5% serum albumin, 2 µg/ml heparin, 1 µg/ml recombinant basic FGF, 1 µg/ml soybean trypsin inhibitor, 1×ITS supplement (insulin-transferrin-selenium, Sigma Cat. No. I 3146), 1:1000 diluted fatty acid supplement (Sigma Cat. No. 7050), and 1:1000 diluted cholesterol. Additionally, the same media can be used for both hypoxic and aerobic cultivation. In one aspect, the growth media is changed from serum based media to serum free media after seeding and the first week of growth.

Incubation conditions will be under appropriate conditions of pH, temperature, and gas (e.g., $O_2$, $CO_2$, etc) to maintain an hypoxic growth condition. In some embodiments, the three-dimensional cell culture can be suspended in the medium during the incubation period in order to maximize proliferative activity and generate factors that facilitate the desired biological activities of the fractions. In addition, the culture may be "fed" periodically to remove the spent media, depopulate released cells, and add new nutrient source. During the incubation period, the cultured cells grow linearly along and envelop the filaments of the three-dimensional scaffold before beginning to grow into the openings of the scaffold.

During incubation under hypoxic conditions, as compared to incubation under normal atmospheric oxygen concentrations of about 15-20%, thousands of genes are differentially expressed. Several genes have been found to be upregulated or downregulated in such compositions, most notably certain laminin species, collagen species and Wnt factors. In various aspects, the three dimensional ECM may be defined by the characteristic fingerprint or suite of cellular products produced by the cells due to growth in hypoxic condition as compared with growth under normal conditions. In the ECM compositions specifically exemplified herein, the three-dimensional tissues and surrounding media are characterized by expression and/or secretion of various factors.

The three dimensional tissues and compositions described herein have ECM that is present on the scaffold or framework. In some aspects, the ECM includes various laminin and collagen types due to growth under hypoxic conditions and selection of cells grown on the support. The proportions of ECM proteins deposited can be manipulated or enhanced by selecting fibroblasts which elaborate the appropriate collagen type as well as growing the cells under hypoxic conditions in which expression of specific laminin and collagen species are upregulated or down-regulated.

Selection of fibroblasts can be accomplished in some aspects using monoclonal antibodies of an appropriate isotype or subclass that define particular collagen types. In other aspects, solid substrates, such as magnetic beads, may be used to select or eliminate cells that have bound antibody. Combination of these antibodies can be used to select (positively or negatively) the fibroblasts which express the desired collagen type. Alternatively, the stroma used to inoculate the framework can be a mixture of cells which synthesize the desired collagen types. The distribution and origins of the exemplary type of collagen are shown in Table I.

TABLE 1

Distributions and Origins of Various Types of Collagen

| Collagen Type | Principle Tissue Distribution | Cells of Origin |
| --- | --- | --- |
| I | Loose and dense ordinary connective tissue; collagen fibers | Fibroblasts and reticular cells; smooth muscle cells |
| | Fibrocartilage | |
| | Bone | Osteoblasts |
| | Dentin | Odontoblasts |
| II | Hyaline and elastic cartilage | Chondrocytes |
| | Vitreous body of eye | Retinal cells |
| III | Loose connective tissue; reticular fibers | Fibroblasts and reticular cells |
| | Papillary layer of dermis | Smooth muscle cells; endothelial cells |
| | Blood vessels | |
| IV | Basement membranes | Epithelial and endothelial cells |
| | Lens capsule of eye | Lens fibers |
| V | Fetal membranes; placenta | Fibroblasts |
| | Basement membranes | |
| | Bone | |
| | Smooth muscle | Smooth muscle cells |
| IV | Basement membranes | Epithelial and endothelial cells |
| | Lens capsule of the eye | Lens fiber |
| V | Fetal membranes; placenta | Fibroblasts |
| | Basement membranes | |
| | Bone | |
| | Smooth muscle | Smooth muscle cells |
| VI | Connective tissue | Fibroblasts |
| VII | Epithelial basement membranes | Fibroblasts |
| | anchoring fibrils | keratinocytes |
| VIII | Cornea | Corneal fibroblasts |
| IX | Cartilage | |
| X | Hypertrophic cartilage | |
| XI | Cartilage | |
| XII | Papillary dermis | Fibroblasts |
| XIV (undulin) | Reticular dermis | Fibroblasts |
| XVII | P170 bullous pemphigoid antigen | Keratinocytes |

Additional types of collagen that may be present in ECM compositions are shown in Table 2.

TABLE 2

Types of Collagen and Corresponding Gene(s)

| Collagen Type | Gene(s) |
| --- | --- |
| I | COL1A1, COL1A2 |
| II | COL2A1 |
| III | COL3A1 |
| IV | COL4A1, COL4A2, COL4A3, COL4A4, COL4A5, COL4A6 |
| V | COL5A1, COL5A2, COL5A3 |
| VI | COL6A1, COL6A2, COL6A3 |
| VII | COL7A1 |
| VIII | COL8A1, COL8A2 |
| IX | COL9A1, COL9A2, COL9A3 |
| X | COL10A1 |
| XI | COL11A1, COL11A2 |
| XII | COL12A1 |
| XIII | COL13A1 |
| XIV | COL14A1 |
| XV | COL15A1 |
| XVI | COL16A1 |
| XVII | COL17A1 |
| XVIII | COL18A1 |
| XIX | COL19A1 |
| XX | COL20A1 |
| XXI | COL21A1 |
| XXII | COL22A1 |
| XXIII | COL23A1 |
| XXIV | COL24A1 |
| XXV | COL25A1 |
| XXVI | EMID2 |
| XXVII | COL27A1 |
| XXVIII | COL28A1 |

As discussed above the ECM compositions described herein include various collagens. As shown in Table 3 of Example 1, expression of several species of collagen are found to be upregulated in hypoxic cultured ECM compositions. Accordingly, in one aspect of the present invention, the ECM composition including one or more embryonic proteins, includes upregulation of collagen species as compared with that produced in oxygen conditions of about 15-20% oxygen. In another aspect, the upregulated collagen species are type V alpha 1; IX alpha 1; IX alpha 2; VI alpha 2; VIII alpha 1; IV, alpha 5; VII alpha 1; XVIII alpha 1; and XII alpha 1.

In addition to various collagens, the ECM composition described herein include various laminins. Laminins are a family of glycoprotein heterotrimers composed of an alpha, beta, and gamma chain subunit joined together through a coiled-coil domain. To date, 5 alpha, 4 beta, and 3 gamma laminin chains have been identified that can combine to form 15 different isoforms. Within this structure are identifiable domains that possess binding activity towards other laminin and basal lamina molecules, and membrane-bound receptors. Domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

Laminin chains possess shared and unique functions and are expressed with specific temporal (developmental) and spatial (tissue-site specific) patterns. The laminin alpha-chains are considered to be the functionally important portion of the heterotrimers, as they exhibit tissue-specific distribution patterns and contain the major cell interaction sites. Vascular endothelium is known to express two laminin isoforms, with varied expression depending on the developmental stage, vessel type, and the activation state of the endothelium.

Accordingly, in one aspect of the present invention, the ECM composition including one or more embryonic proteins, includes upregulation or downregulation of various laminin species as compared with that produced in oxygen conditions of about 15-20% oxygen.

Laminin 8, is composed of alpha-4, beta-1, and gamma-1 laminin chains. The laminin alpha-4 chain is widely distributed both in adults and during development. In adults it can be identified in the basement membrane surrounding cardiac, skeletal, and smooth muscle fibers, and in lung alveolar septa. It is also known to exist in the endothelial basement membrane both in capillaries and larger vessels, and in the perineurial basement membrane of peripheral nerves, as well as in intersinusoidal spaces, large arteries, and smaller arterioles of bone marrow. Laminin 8 is a major laminin isoform in the vascular endothelium that is expressed and adhered to by platelets and is synthesized in 3T3-L1 adipocytes, with its level of synthesis shown to increase upon adipose conversion of the cells. Laminin 8 is thought to be the laminin isoform generally expressed in mesenchymal cell lineages to induce microvessels in connective tissues. Laminin 8 has also been identified in mouse bone marrow primary cell cultures, arteriolar walls, and intersinusoidal spaces where it is the major laminin isoform in the developing bone marrow. Due to its localization in adult bone marrow adjacent to hematopoietic cells, laminin isoforms containing the alpha-4 chain are likely to have biologically relevant interactions with developing hematopoietic cells.

Accordingly, in another aspect of the present invention the ECM includes upregulation of laminin species, such as laminin 8. In another aspect, laminins produced by the three dimensional tissues of the present invention, includes at least laminin 8, which defines a characteristic or signature of the laminin proteins present in the composition.

The ECM compositions described herein can include various Wnt factors. Wnt family factors are signaling molecules having roles in a myriad of cellular pathways and cell-cell interaction processes. Wnt signaling has been implicated in tumorigenesis, early mesodermal patterning of the embryo, morphogenesis of the brain and kidneys, regulation of mammary gland proliferation, and Alzheimer's disease. As shown in Table 4 of Example 1, expression of several species of Wnt proteins are found to be upregulated in hypoxic cultured ECM compositions. Accordingly, in one aspect of the present invention, the ECM composition including one or more embryonic proteins, includes upregulation of Wnt species as compared with that produced in oxygen conditions of about 15-20% oxygen. In another aspect, the upregulated Wnt species are wnt 7a and wnt 11. In another aspect, Wnt factors produced by the three dimensional tissues of the present invention, include at least wnt7a, and wnt11, which defines a characteristic or signature of the Wnt proteins present in the composition.

The culturing methods described herein, including culture under hypoxic conditions, have also been shown to upregulate expression of various growth factors. Accordingly, the ECM compositions described herein can include various growth factors, such as a vascular endothelial growth factor (VEGF). As used herein, a VEGF in intended to include all known VEGF family members. VEGFs are a sub-family of growth factors, more specifically of platelet-derived growth factor family of cystine-knot growth factors. VEGFs have a well known role in both vasculogenesis and angiogenesis. Several VEGFs are known, including VEGF-A, which was formerly known as VEGF before the discovery of other VEGF species. Other VEGF species include placenta growth factor (PlGF), VEGF-B, VEGF-C and VEGF-D. Additionally, several isoforms of human VEGF are well known.

In accordance with the increased production of Wnt proteins as well as growth factors by culturing under hypoxic conditions as described herein, the present invention further provides a method of producing a Wnt protein and a vascular endothelial growth factor (VEGF). The method can include culturing cells under hypoxic conditions as described herein, on a three-dimensional surface in a suitable growth medium, to produce the Wnt protein and the VEGF. In an exemplary aspect, the Wnt species are wnt 7a and wnt 11 and the VEGF is VEGF-A. The proteins may be further processed or harvested as described further herein or by methods known in the art.

A discussed throughout, the ECM compositions of the present invention includes both soluble and non-soluble fractions or any portion thereof. It is to be understood that the compositions of the present invention may include either or both fractions, as well as any combination thereof. Additionally, individual components may be isolated from the fractions to be used individually or in combination with other isolates or known compositions.

Accordingly, in various aspects, ECM compositions produced using the methods of the present invention may be used directly or processed in various ways, the methods of which may be applicable to both the non-soluble and soluble fractions. The soluble fraction, including the cell-free supernatant and media, may be subject to lyophilization for preserving and/or concentrating the factors. Various biocompatible preservatives, cryoprotectives, and stabilizer agents may be used to preserve activity where required. Examples of biocompatible agents include, among others, glycerol, dimethyl sulfoxide, and trehalose. The lyophilizate may also have one or more excipients such as buffers, bulking agents, and tonicity modifiers. The freeze-dried media may be reconstituted by addition of a suitable solution or pharmaceutical diluent, as further described below.

In other aspects, the soluble fraction is dialyzed. Dialysis is one of the most commonly used techniques to separate sample components based on selective diffusion across a porous membrane. The pore size determines molecular-weight cutoff (MWCO) of the membrane that is characterized by the molecular-weight at which 90% of the solute is retained by the membrane. In certain aspects membranes with any pore size is contemplated depending on the desired cutoff. Typical cutoffs are 5,000 Daltons, 10,000 Daltons, 30,000 Daltons, and 100,000 Daltons, however all sizes are contemplated.

In some aspects, the soluble fraction may be processed by precipitating the active components (e.g., growth factors) in the media. Precipitation may use various procedures, such as salting out with ammonium sulfate or use of hydrophilic polymers, for example polyethylene glycol.

In other aspects, the soluble fraction is subject to filtration using various selective filters. Processing the soluble fraction by filtering is useful in concentrating the factors present in the fraction and also removing small molecules and solutes used in the soluble fraction. Filters with selectivity for specified molecular weights include <5000 Daltons, <10,000 Daltons, and <15,000 Daltons. Other filters may be used and the processed media assayed for therapeutic activity as described herein. Exemplary filters and concentrator system include those based on, among others, hollow fiber filters, filter disks, and filter probes (see, e.g., Amicon Stirred Ultrafiltration Cells).

In still other aspects, the soluble fraction is subject to chromatography to remove salts, impurities, or fractionate various components of the medium. Various chromatographic techniques may be employed, such as molecular sieving, ion exchange, reverse phase, and affinity chromatographic techniques. For processing conditioned medium without significant loss of bioactivity, mild chromatographic media may be used. Non-limiting examples include, among others, dextran, agarose, polyacrylamide based separation media (e.g., available under various tradenames, such as Sephadex, Sepharose, and Sephacryl).

In still other aspects, the conditioned media is formulated as liposomes. The growth factors may be introduced or encapsulated into the lumen of liposomes for delivery and for extending life time of the active factors. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see, e.g., U.S. Pat. No. 5,833,948).

The soluble fraction may be used directly without additional additives, or prepared as pharmaceutical compositions with various pharmaceutically acceptable excipients, vehicles or carriers. A "pharmaceutical composition" refers to a form of the soluble and/or non-soluble fractions and at least one pharmaceutically acceptable vehicle, carrier, or excipient. For intradermal, subcutaneous or intramuscular administration, the compositions may be prepared in sterile suspension, solutions or emulsions of the ECM compositions in aqueous or oily vehicles. The compositions may also contain formulating agents, such as suspending, stabilizing or dispersing agents. Formulations for injection may be presented in unit dosage form, ampules in multidose containers, with or without preservatives. Alternatively, the compositions may be presented in powder form for reconstitution with a suitable vehicle including, by way of example and not limitation, sterile pyrogen free water, saline, buffer, or dextrose solution.

In other aspects, the three dimensional tissues are cryopreserved preparations, which are thawed prior to use. Pharmaceutically acceptable cryopreservatives include, among others, glycerol, saccharides, polyols, methylcellulose, and dimethyl sulfoxide. Saccharide agents include monosaccharides, disaccharides, and other oligosaccharides with glass transition temperature of the maximally freeze-concentrated solution (Tg) that is at least −60, −50, −40, −30, −20, −10, or 0° C. An exemplary saccharide for use in cryopreservation is trehalose.

In some aspects, the three dimensional tissues are treated to kill the cells prior to use. In some aspects, the ECM deposited on the scaffolds may be collected and processed for administration (see U.S. Pat. Nos. 5,830,708 and 6,280,284, incorporated herein by reference).

In other embodiments, the three dimensional tissue may be concentrated and washed with a pharmaceutically acceptable medium for administration. Various techniques for concentrating the compositions are available in the art, such as centrifugation or filtering. Examples include, dextran sedimentation and differential centrifugation. Formulation of the three dimensional tissues may also involve adjusting the ionic strength of the suspension to isotonicity (i.e., about 0.1 to 0.2) and to physiological pH (i.e., pH 6.8 to 7.5). The formulation may also contain lubricants or other excipients to aid in administration or stability of the cell suspension. These include, among others, saccharides (e.g., maltose) and organic polymers, such as polyethylene glycol and hyaluronic acid. Additional details for preparation of various formulations are described in U.S. Patent Publication No. 2002/0038152, incorporated herein by reference.

As discussed above, the ECM compositions of the present invention may be processed in a number of ways depending on the anticipated application and appropriate delivery or administration of the ECM composition. For example, the compositions may be delivered as three-dimensional scaffolds or implants, or the compositions may be formulated for injection as described above. The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The ECM compositions of the present invention have a variety of applications including, but not limited to, promoting repair and/or regeneration of damaged cells or tissues, use in patches to promote tissue regeneration, use in tissue culture systems for culturing cells, such as stem cells, use in surface coatings used in association with implantable devices (e.g., pacemakers, stents, stent grafts, vascular prostheses, heart valves, shunts, drug delivery ports or catheters), promoting soft tissue repair, augmentation, and/or improvement of a skin surface, such as wrinkles, use as a biological anti-adhesion agent or as a biological vehicle for cell delivery or maintenance at a site of delivery.

Additionally, the ECM compositions derived from culturing cells as described in any method herein, may be used in any other application or method of the present invention. For example, the ECM compositions generated by culturing cells using the tissue culture system of the present invention may be used, for example, in the repair and/or regeneration of cells, use in patches to promote tissue regeneration, use in tissue culture systems for culturing cells, such as stem cells, use in surface coatings used in association with implantable devices (e.g., pacemakers, stents, stent grafts, vascular prostheses, heart valves, shunts, drug delivery ports or catheters), promoting soft tissue repair, augmentation, and/or improvement of a skin surface, such as wrinkles, use as a biological anti-adhesion agent or as a biological vehicle for cell delivery or maintenance at a site of delivery.

In various embodiments, the present invention includes methods for repair and/or regeneration of cells or tissue and promoting soft tissue repair. One embodiment includes a method of repair and/or regeneration of cells by contacting cells to be repaired or regenerated with the ECM compositions of the present invention. The method may be used for repair and/or regeneration of a variety of cells as discussed herein, including osteochondral cells.

In one aspect, the method contemplates repair of osteochondral defects. As used herein, "osteochondral cells" refers to cells which belong to either the chondrogenic or osteogenic lineage or which can undergo differentiation into either the chondrogenic or osteogenic lineage, depending on the environmental signals. This potential can be tested in vitro or in vivo by known techniques. Thus, in one aspect, the ECM compositions of the present invention are used to repair and/or regenerate, chondrogenic cells, for example, cells which are capable of producing cartilage or cells which themselves differentiate into cells producing cartilage, including chondrocytes and cells which themselves differentiate into chondrocytes (e.g., chondrocyte precursor cells). Thus, in another aspect, the compositions of the present invention are useful in repair and/or regeneration of connective tissue. As used herein, "connective tissue" refers to any of a number of structural tissues in the body of a mammal including but not limited to bone, cartilage, ligament, tendon, meniscus, dermis, hyperdermis, muscle, fatty tissue, joint capsule.

The ECM compositions of the present invention may be used for treating osteochondral defects of a diarthroidal joint, such as knee, an ankle, an elbow, a hip, a wrist, a knuckle of either a finger or toe, or a temperomandibular joint. Such osteochondral defects can be the result of traumatic injury (e.g., a sports injury or excessive wear) or a disease such as osteoarthritis. A particular aspect relates to the use of the matrix of the present invention in the treatment or prevention of superficial lesions of osteoarthritic cartilage. Additionally the present invention is of use in the treatment or prevention of osteochondral defects which result from ageing or from giving birth. Osteochondral defects in the context of the present invention should also be understood to comprise those conditions where repair of cartilage and/or bone is required in the context of surgery such as, but not limited to, cosmetic surgery (e.g., nose, ear). Thus such defects can occur anywhere in the body where cartilage or bone formation is disrupted or where cartilage or bone are damaged or non-existent due to a genetic defect.

As discussed above, growth factors or other biological agents which induce or stimulate growth of particular cells may be included in the ECM compositions of the present invention. The type of growth factors will be dependent on the cell-type and application for which the composition is intended. For example, in the case of osteochondral cells, additional bioactive agents may be present such as cellular growth factors (e.g., TGF-β), substances that stimulate chondrogenesis (e.g., BMPs that stimulate cartilage formation such as BMP-2, BMP-12 and BMP-13), factors that stimulate migration of stromal cells to the scaffold, factors that stimulate matrix deposition, anti-inflammatories (e.g., non-steroidal anti-inflammatories), immunosuppressants (e.g., cyclosporins). Other proteins may also be included, such as other growth factors such as platelet derived growth factors (PDGF), insulin-like growth factors (IGF), fibroblast growth factors (FGF), epidermal growth factor (EGF), human endothelial cell growth factor (ECGF), granulocyte macrophage colony stimulating factor (GM-CSF), vascular endothelial growth factor (VEGF), cartilage derived morphogenetic protein (CDMP), other bone morphogenetic proteins such as OP-1, OP-2, BMP3, BMP4, BMP9, BMP11, BMP14, DPP, Vg-1, 60A, and Vgr-1, collagens, elastic fibers, reticular fibers, glycoproteins or glycosaminoglycans, such as heparin sulfate, chondroitin-4-sulfate, chondroitin-6-sulfate, dermatan sulfate, keratin sulfate, etc. For example, growth factors such as TGF-β, with ascorbate, have been found to trigger chondrocyte differentiation and cartilage formation by chondrocytes. In addition, hyaluronic acid is a good substrate for the attachment of chondrocytes and other stromal cells and can be incorporated as part of the scaffold or coated onto the scaffold.

Additionally, other factors which influence the growth and/or activity of particular cells may also be used. For example, in the case of chondrocytes, a factor such as a chondroitinase which stimulates cartilage production by chondrocytes can be added to the matrix in order to maintain chondrocytes in a hypertrophic state as described in U.S. Patent Application No. 2002/0122790 incorporated herein by reference. In another aspect, the methods of the present invention include the presence of polysulphated alginates or other polysulphated polysaccharides such as polysulphated cyclodextrin and/or polysulphated inulin, or other components capable of stimulating production of ECM of connective tissue cells as described in International Patent Publication No. WO 2005/054446 incorporated herein by reference.

The cell or tissue to be repaired and/or regenerated may be contacted in vivo or in vitro by any of the methods described herein. For example, the ECM compositions may be injected or implanted (e.g., via ECM tissue, a patch or coated device of the present invention) into the subject. In another aspect, the tissue or cells to be repaired and/or regenerated may be harvested from the subject and cultured in vitro and subsequently implanted or administered to the subject using known surgical techniques.

As discussed above, the ECM compositions of the present invention may be processed in a variety of ways. Accordingly, in one embodiment, the present invention includes a tissue culture system. In various aspects, the culture system is composed of the ECM compositions described herein. The ECM compositions of the present invention may be incorporated into the tissue culture system in a variety of ways. For example, compositions may be incorporated as coatings, by impregnating three-dimensional scaffold materials as described herein, or as additives to media for culturing cells. Accordingly, in one aspect, the culture system can include three-dimensional support materials impregnated with any of the ECM compositions described herein, such as growth factors or embryonic proteins.

The ECM compositions described herein may serve as a support or three-dimensional support for the growth of various cell types. Any cell type capable of cell culture is contemplated. In one aspect, the culture system can be used to support the growth of stem cells. In another aspect, the stem cells are embryonic stem cells, mesenchymal stem cells or neuronal stem cells.

The tissue culture system may be used for generating additional ECM compositions, such as implantable tissue. Accordingly, culturing of cells using the tissue culture system of the present invention may be performed in vivo or in vitro. For example, the tissue culture system of the present invention may be used to generate ECM compositions for injection or implantation into a subject. The ECM compositions generated by the tissue culture system may be processed and used in any method described herein.

The ECM compositions of the present invention may be used as a biological vehicle for cell delivery. As described herein, the ECM compositions may include both soluble and/or non-soluble fractions. As such, in another embodiment of the present invention, a biological vehicle for cell delivery or maintenance at a site of delivery including the ECM compositions of the present invention, is described. The ECM compositions of the present invention, including cells and three-dimensional tissue compositions, may be used to promote and/or support growth of cells in vivo. The vehicle can be used in any appropriate application, for example to support injections of cells, such as stem cells, into damaged heart muscle or for tendon and ligament repair as described above.

Appropriate cell compositions (e.g., isolated ECM cells of the present invention and/or additional biological agents) can be administered before, after or during the ECM compositions are implanted or administered. For example, the cells can be seeded into the site of administration, defect, and/or implantation before the culture system or biological delivery vehicle is implanted into the subject. Alternatively, the appropriate cell compositions can be administered after (e.g., by injection into the site). The cells act therein to induce tissue regeneration and/or cell repair. The cells can be seeded by any means that allows administration of the cells to the defect site, for example, by injection. Injection of the cells can be by any means that maintains the viability of the cells, such as, by syringe or arthroscope.

ECM compositions have been described for promoting angiogenesis in organs and tissues by administering such compositions to promote endothelialization and vascularization in the heart and related tissues. Accordingly, in yet another embodiment, the present invention includes a surface coating used in association with implantation of a device in a subject including the ECM compositions described herein. The coating may be applied to any device used in implantation or penetration of a subject, such as a pacemaker, a stent, a stent graft, a vascular prosthesis, a heart valve, a shunt, a drug delivery port or a catheter. In certain aspects, the coating can be used for modifying wound healing, modifying inflammation, modifying a fibrous capsule formation, modifying tissue ingrowth, or modifying cell ingrowth. In another embodiment, the present invention includes a for treatment of damaged tissue, such as heart, intestinal, infarcted or ischemic tissue. Presented below are examples discussing generation of ECM compositions contemplated for such applications. The preparation and use of ECM compositions grown under normal oxygen conditions is described in U.S. Patent Application No. 2004/0219134 incorporated herein by reference.

In another embodiment, the present invention includes various implantable devices and tissue regeneration patches including the ECM compositions described herein which allow for benefits, such as tissue ingrowth. As discussed herein, the ECM compositions may serve as coatings on medical devices, such as patches or other implantable devices. In various aspects, such devices are useful for wound repair, hernia repair, pelvic floor repair (e.g., pelvic organ prolapse), rotator cuff repair and the like. In related aspects, coatings are useful for orthopedic implants, cardiovascular implants, urinary slings and pacemaker slings.

For example, the basic manifestation of a hernia is a protrusion of the abdominal contents into a defect within the fascia. Surgical approaches toward hernia repair is focused on reducing the hernial contents into the peritoneal cavity and producing a firm closure of the fascial defect either by using prosthetic, allogeneic or autogenous materials. A number of techniques have been used to produce this closure, however, drawbacks to current products and procedures include hernia recurrence, where the closure weakens again, allowing the abdominal contents back into the defect. In herniorrhaphy, a corrective tissue regeneration patch, such as a bioresorbable or synthetic mesh coated with ECM compositions could be used.

A variety of techniques are known in the art for applying biological coatings to medical device surfaces that may be utilized with the present invention. For example, ECM compositions may be coated using photoactive crosslinkers allowing for permanent covalent bonding to device surfaces upon activation of the crosslinker by applying ultraviolet radiation. An exemplary crosslinker is TriLite™ crosslinker, which has been shown to be non-cytotoxic, non-irritating to biological tissue and non-sensitizing. ECM materials may be unseparated or separated into individual components, such as human collagens, hyaluronic acid (HA), fibronectin, and the like before coating or incorporation into various implantable devices. Further, additional growth factors and such may be incorporated to allow for beneficial implantation characteristics, such as improved cell infiltration.

In various related embodiments, the present invention provides methods and devices applicable in cosmetic/cosmeceutical applications, such as, but not limited to anti-aging, anti-wrinkle, skin fillers, moisturizers, pigmentation augmentation, skin firming, and the like. Accordingly, in one embodiment the present invention includes a method for improvement of a skin surface in a subject including administering to the subject at the site of a wrinkle, the ECM compositions described herein. In a related embodiment, the present invention includes a method for soft tissue repair or augmentation in a subject including administering to the subject at the site of a wrinkle, the ECM compositions described herein. In various cosmetic applications, the compositions may be formulated as appropriate, such as injectable and topical formulations. As discussed further in the Examples included herein, ECM compositions formulated as topicals have been shown to be effective in various skin aesthetics applications, such as anti-wrinkle, anti-aging applications as well as an adjunct to ablative laser surgery. Several beneficial characteristics of ECM containing topicals have been shown. Such benefits include 1) facilitating re-epithelization following resurfacing; 2) reduction of non-ablative and ablative fractional laser resurfacing symptoms (e.g., erythema, edema, crusting, and sensorial discomfort); 3) generating smooth, even textured skin; 4) generating skin moisturization; 5) reducing appearance of fine lines/wrinkles; 6) increasing skin firmness and suppleness; 7) reducing skin dyspigmentation; and 8) reducing red, blotchy skin.

The compositions of the present invention may be prepared as known in the art, however employing the innovative culture methods described herein (e.g., culture under hypoxic conditions). The preparation and use of ECM compositions created under normal oxygen culture conditions for the repair and/or regeneration of cells, improvement of skin surfaces, and soft tissue repair are described in U.S. Pat. Nos. 5,830,708, 6,284, 284, U.S. Patent Application No. 2002/0019339 and U.S. Patent Application No. 2002/0038152 incorporated herein by reference.

In another embodiment, the present invention includes a biological anti-adhesion agent including the ECM compositions described herein. The agent can be used in such applications as anti-adhesion patches used after the creation of intestinal or blood vessel anastomises.

The compositions or active components used herein, will generally be used in an amount effective to treat or prevent the particular disease being treated. The compositions may be administered therapeutically to achieve therapeutic benefit or prophylactically to achieve prophylactic benefit. By therapeutic benefit is meant eradication or amelioration of the underlying condition or disorder being treated. Therapeutic benefit also includes halting or slowing the progression of the disease, regardless of whether improvement is realized.

The amount of the composition administered will depend upon a variety of factors, including, for example, the type of composition, the particular indication being treated, the mode of administration, whether the desired benefit is prophylactic or therapeutic, the severity of the indication being treated and the age and weight of the patient, and effectiveness of the dosage form. Determination of an effective dosage is well within the capabilities of those skilled in the art.

Initial dosages may be estimated initially from in vitro assays. Initial dosages can also be estimated from in vivo data, such as animal models. Animals models useful for testing the efficacy of compositions for enhancing hair growth include, among others, rodents, primates, and other mammals. The skilled artisans can determine dosages suitable for human administration by extrapolation from the in vitro and animal data.

Dosage amounts will depend upon, among other factors, the activity of the conditioned media, the mode of administration, the condition being treated, and various factors discussed above. Dosage amount and interval may be adjusted individually to provide levels sufficient to the maintain the therapeutic or prophylactic effect.

Presented below are examples discussing generation of ECM compositions contemplated for the discussed applications. The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Differential Gene Expression in ECM Compositions Grown under Hypoxic Conditions

Primary human neonatal foreskin fibroblasts were cultured as standard monolayers in tissue culture flasks and compared to three-dimensional fibroblast cultures, within a naturally deposited, fetal-like ECM. The cultures were grown as disclosed herein. To assess differential expression of genes, samples of total RNA were completed using Agilent Whole Human Genome Oligo Microarrays® for global gene expression (including less than 40,000 genes) following the manufacturer's protocol.

Upon comparison, fibroblasts were found to regulate collagen and ECM gene expression in three-dimensional cultures within a hypoxic cultured naturally secreted ECM. Upregulation and downregulation of expression of various collagen and ECM genes are evident in Table 3.

TABLE 3

Differential Collagen and ECM Expression in Hypoxic Three-dimensional Fibroblast Cultures

| GENE | FOLD INCREASE | FOLD DECREASE |
| --- | --- | --- |
| COL4A1 | 17.2 | |
| COL20A1 | 6.88 | |
| COL19A1 | 5.22 | |
| COL9A1 | 4.81 | |
| COL10A1 | 4.45 | |
| COL6A3 | 3.48 | |
| COL9A2 | 2.48 | |

TABLE 3-continued

Differential Collagen and ECM Expression in Hypoxic Three-dimensional Fibroblast Cultures

| GENE | FOLD INCREASE | FOLD DECREASE |
|---|---|---|
| COL14A1 | 2 | |
| SPARC | 2.74 | |
| COL1A2 | | 3.45 |
| COL13A1 | | 4 |
| COL18A1 | | 4.76 |
| COL1A2 | | 7.14 |

Upon comparison, fibroblasts were found to regulate gene expression of Wnt pathway genes in three-dimensional cultures within a hypoxic cultured naturally secreted ECM. Upregulation and downregulation of expression of various Wnt pathway genes are evident in Table 4.

TABLE 4

Differential Wnt Expression in Hypoxic Three-dimensional Fibroblast Cultures

| GENE | FOLD INCREASE | FOLD DECREASE |
|---|---|---|
| WNT4 | 5.94 | |
| WNT7a | 5.43 | |
| WNT 7b | 4.05 | |
| WNT 2b | 3.95 | |
| WNT 10a | 3.86 | |
| WNT 8b | 3.48 | |
| WNT 6 | 3.36 | |
| WNT 3a | 3.19 | |
| WNT 9b | 3.06 | |
| WNT 9a | 3.02 | |
| WNT 11 | 2.89 | |
| WNT 5a | | 8.33 |
| WNT 2 | | 7.14 |
| WNT 5b | | 5.26 |
| LRP6 | 3.43 | |
| LRP3 | 2.27 | |
| LRP11 | | 10 |
| LRP12 | | 7.69 |
| DKK1 | | 50 |
| DKK3 | | 5.88 |
| FSZD5 | 4.48 | |
| FRZ9 | 3.85 | |
| FRZB | 3.36 | |
| FRZD1 | 2.94 | |
| SFRP2 | 2.95 | |
| FRZD1 | 2.92 | |
| FRZD3 | 2.84 | |
| AXIN2 | 4.4 | |
| KREMEN2 | 4.24 | |
| KREMEN1 | 3.45 | |
| b-CATENIN | | 4.76 |
| GSK3b | | 11.1 |
| GSK3a | | 6.67 |
| bFGF | | 50 |

Upon comparison, fibroblasts were found to regulate gene expression of bone morphogenetic protein (BMP) pathway genes in three-dimensional cultures within a hypoxic cultured naturally secreted ECM. Upregulation and downregulation of expression of various BMP pathway genes are evident in Table 5.

TABLE 5

Differential BMP Expression in Hypoxic Three-dimensional Fibroblast Cultures

| GENE | FOLD INCREASE | FOLD DECREASE |
|---|---|---|
| BMP7/OP1 | 4.88 | |
| BMP2 | 4.19 | |
| BMP5 | 3.49 | |
| BMP3 | 3.44 | |
| BMPrecIb | 3.37 | |
| BMP8b | 3.36 | |
| BMP 8a | 3.15 | |
| BMP 10 | 2.86 | |
| BMP1 | 2.12 | |
| BMPrecIa | | 2.5 |
| Osteocalcin | | 2.5 |
| Osteopontin | | 6.25 |
| BMPrecII | | 6.25 |

Upon comparison, fibroblasts were found to regulate expression of additional genes in three-dimensional cultures within a the hypoxic cultured naturally secreted ECM. Upregulation and downregulation of expression of additional genes are evident in Table 6. Results indicate that hypoxic culture conditions result in a 14.78-fold increase in mRNA expression for hypoxia-inducible factor (HIF 1A) and a 4.9 decrease in its respective inhibitor. This suggests that the hypoxic cultured conditioned medium is experiencing a low oxygen tension environment (hypoxia) because the messenger RNA for HIF 1A that codes for the translation of the protein is up-regulated and its inhibitor is down-regulated. Further, VEGFB (4.33-fold increase), KGF (11.51-fold increase), and IL-8 (5.81-fold increase) levels were also up-regulated under hypoxic culture conditions.

TABLE 6

Additional Gene Expression Changes Resulting from Low Oxygen Culture of Fibroblast ECM In Vivo.

| GENES | FOLD INCREASE | FOLD DECREASE |
|---|---|---|
| Collagens | | |
| COL5A1 | 6.21 | |
| COL9A2 | 3.96 | |
| COL6A2 | 3.78 | |
| COL6A2 | 3.21 | |
| COL11A1 | 3.07 | |
| COL8A1 | 2.78 | |
| COL4A5 | 2.45 | |
| COL7A1 | 2.45 | |
| COL18A1 | 2.41 | |
| COL12A1 | 2.04 | |
| COL1A2 | | 0.5 |
| COL14A1 | | 0.45 |
| COL4A1 | | 0.45 |
| COL5A2 | | 0.23 |
| COL6A1 | | 0.16 |
| Matrix Metalloproteinases (MMPs) | | |
| MMP23B | 2.75 | |
| MMP27 | | 0.24 |
| MMP28 | | 0.17 |
| MMP10 | | 0.16 |
| MMP1 | | 0.16 |
| MMP7 | | 0.1 |
| MMP14 | | 0.08 |
| MMP3 | | 0.06 |
| MMP12 | | 0.05 |
| Other ECM | | |
| HAPLN3 | 8.11 | |
| ACAN L12234 | 6.48 | |
| AGC1 | 3.32 | |

TABLE 6-continued

Additional Gene Expression Changes Resulting from Low
Oxygen Culture of Fibroblast ECM In Vivo.

| GENES | FOLD INCREASE | FOLD DECREASE |
|---|---|---|
| LAMA3 | 2.92 | |
| LAMA1 | 2.14 | |
| LAMA5 | 2.14 | |
| Additional Genes | | |
| HIF 1A | 14.18 | |
| HIF 1AN | | 4.9 |
| VEGFB | 4.33 | |
| VEGFC | 3.84 | |
| KGF | 11.51 | |
| IL-8 | 5.81 | |

EXAMPLE 2

Production of Hypoxic ECM using Primary Human Neonatal Foreskin Fibroblasts

Two examples are provided for hypoxic culture of ECM using primary human neonatal foreskin fibroblasts.

Primary human neonatal foreskin fibroblasts were expanded in tissue culture flasks in the presence of 10% fetal bovine serum, 90% High Glucose DMEM with 2 mM L-glutamine (10% FBS/DMEM). Cells were subcultured using 0.05% trypsin/EDTA solution until the $3^{rd}$ passage at which time they were seeded to either Cytodex-1 dextran beads at 0.04 mgs dry beads/ml of medium ($5e^6$ cells/10 mgs beads in a 125 ml spinner flask filled with 100-120 mls), or to nylon mesh ($25e^6$ cells/6×100 $cm^2$ nylon). All cultures were kept in normal atmosphere and 5% $CO_2$ for expansion and seeding, at which point low oxygen cultures were split to an airtight chamber which was flooded with 95% nitrogen/5% $CO_2$ so that a hypoxic environment could be created within the culture medium. This system is maintains about 1-5% oxygen within the culture vessel. Cells were mixed well into the minimum volume needed to cover nylon or beads for seeding, and were subsequently mixed once after 30 minutes, then allowed to sit overnight in a humidified 37° C. incubator. Cultures were fed 10% FBS/DMEM for 2-4 weeks with a 50-70% media exchange, every 2-3 days while cells proliferated and then began depositing ECM. Cultures were fed for another 4-6 weeks using 10% bovine calf serum with iron supplement, and 20 ug/ml ascorbic acid in place of FBS. Spinner flasks were mixed at 15-25 rpm initially and for about 2-4 weeks, at which time they were increased to 45 rpm and maintained at this rate thereafter. Bead cultures formed large amorphous structures containing ECM of as much as 0.5 to 1.0 cm in width and diameter after 4 weeks, and these cultures were therefore hypoxic due to gas diffusion and high metabolic requirements.

In an additional example, primary human neonatal foreskin fibroblasts were expanded in monolayer flasks, and then cultured on nylon mesh scaffolds to support development of an ECM in vitro. Fibroblasts were expanded in DMEM with high glucose, 2 mM L-glutamine, and 10% (v/v) fetal bovine serum. Cultures were also supplemented with 20 µg/ml ascorbic acid. After 3 weeks in ambient oxygen (approximately 16%-20% oxygen) duplicate ECM-containing cultures were switched to hypoxic culture conditions (1%-5% oxygen) in a sealed chamber flushed extensively with 95% nitrogen/5% carbon dioxide (Cat.#MC-101, Billups-Rothenberg, Inc., Del Mar, Calif.). To ensure depletion of atmospheric oxygen from the culture medium, 2-3 hours later the atmosphere was replaced to ensure that the medium contained approximately 1-3% oxygen. Both sets of ECM-containing cultures were grown with twice weekly feedings for another 4 weeks, and then cultures were prepared for RNA isolation. Total cellular RNA was isolated using a commercially available kit according to the manufacturers instructions (Cat.# Z3100, Promega, Inc.). Purified RNA samples were stored at −80° C., prior to processing for microarray analysis of gene expression using Agilent Whole Human Genome Oligo Microarrays®.

In analyzing the results, there were approximately 5,500 differentially expressed transcripts detected from probes prepared from ambient oxygen in comparison to probes from low oxygen cultures, using Agilent Whole Human Genome Oligo Microarrays®. Of these, about half (2,500) were greater than 2.0 fold increased by low oxygen, and about half (2,500) were decreased greater than 2.0 fold in low oxygen. This indicates that low oxygen led to significant changes in gene expression in vitro. Of particular interest, transcripts for ECM proteins, particularly a number of collagen genes were up-regulated, while a number of genes for matrix-degrading enzymes were down-regulated.

EXAMPLE 3

Tissue-Engineered Human Embryonic Extracellular Matrix for Therapeutic Applications The embryonic ECM creates an environment conducive to rapid cell proliferation and healing without the formation of scars or adhesions. It was hypothesized that the growth of human neonatal fibroblasts in 3 dimensions under conditions that simulate the early embryonic environment prior to angiogenesis (hypoxia and reduced gravitational forces) would generate an ECM with fetal properties. Gene chip array analysis showed the differential expression of over 5000 genes under the hypoxic versus traditional tissue culture conditions. The ECM produced was similar to fetal mesenchymal tissue in that it is relatively rich in collagens type III, IV, and V, and glycoproteins such as fibronectin, SPARC, thrombospondin, and hyaluronic acid. Since the ECM also plays an important regulatory role in binding and presenting growth factors in putative niches which support regenerative stem cell populations with key growth factors, we evaluated the effects of hypoxia on growth factor expression during the development of the fetal-like ECM in culture. Hypoxia can also enhance expression of factors which regulate wound healing and organogenesis, such as VEGF, FGF-7, and TGF-β, as well as multiple wnts including wnts 2b, 4, 7a, 10a, and 11. The embryonic human ECM also stimulated an increase of metabolic activity in human fibroblasts in vitro, as measured by increased enzymatic activity using the MTT assay. Additionally, we detected an increase in cell number in response to human ECM. This human ECM can be used as a biological surface coating, and tissue filler treatment in various therapeutic applications where new tissue growth and healing without scarring or adhesions.

EXAMPLE 4

Production of Naturally-Soluble Wnt Activity for Regenerative Medicine Applications Stem or progenitor cells that can regenerate adult tissues, such as skin or blood, recapitulate embryonic development to some extent to accomplish this regeneration. A growing number of studies have shown that key regulators of stem cell pluripotency and lineage-specific differentiation active during embryogenesis are re-expressed in the adult under certain circumstances. The WNT family of secreted morphogenetic growth and development factors is among the growth factors which can potentially provide valuable research tools and eventually therapeutic treatments in the clinic. However, Wnt's have proven refractory to standard recombinant expression and purification techniques to date on a commercial scale, and there are no reports of large-scale WNT protein production to enable clinical development of WNT-based products. Techniques have been developed for growing fetal-like ECM in culture using neonatal human dermal fibroblasts on various scaffolds in culture to generate three-dimensional tissue-equivalents. In this process, it was discovered that these cultures can provide a commercial-scale source of bioactive WNT's contained in the serum-free conditioned medium used for ECM production. Here we present data on this WNT product candidate.

Gene expression analysis of the cells demonstrated that at least 3 WNT genes were expressed (wnt 5a, wnt 7a, and wnt 11), and a small number of genes related to wnt signaling were expressed as well; however, their function is not completely understood. The gene expression data was extended to an in vitro bioassay for wnt-signaling (nuclear translocation of β-catenin in primary human epidermal keratinocytes) and writ activity on blood stem cells was evaluated. Both assays demonstrated activity consistent with canonical writ activity. Furthermore, conditioned media from these cultures showed wnt activity when injected into the skin of mice, inducing hair follicle stem cells to enter anagen, thus causing hair growth. This indicates that the stabilized WNT activity within the defined and serum-free condition medium did not require purification. This product can be used for hair follicle regeneration and as a valuable research tool for the culture of various human stem cells.

EXAMPLE 5

Hypoxic Fibroblasts Demonstrate Unique ECM Production and Growth Factor Expression Human neonatal dermal fibroblasts produce an ECM when cultured in vitro, which closely mimics the dermis and which can replace the damaged dermis in regenerative medicine applications such as wound healing. Since the process of wound healing also recapitulates embryonic development, by simulating the embryonic environment we hypothesize that the ECM produced will provide an enhanced ECM for tissue regeneration applications. Therefore, human neonatal fibroblast-derived ECM were grown under hypoxic conditions in culture, to simulate the hypoxia which exists in the early embryo prior to angiogenesis. The goal was to generate an ECM with fetal properties using hypoxic conditions during tissue development in culture.

The ECM produced in these hypoxic cultures was similar to fetal mesenchymal tissue in that it is relatively rich in collagens type III and V, and glycoproteins such as fibronectin, SPARC, thrombospondin, and hyaluronic acid. Since the ECM also plays an important regulatory role in binding and presenting growth factors in putative niches which support regenerative stem cell populations with key growth factors, we evaluated the effects of hypoxia on growth factor expression during the development of the fetal-like ECM in culture. It was shown that hypoxia can also enhance expression of factors which regulate wound healing and organogenesis, such as VEGF, FGF-7, and TGF-β.

The human ECM also stimulated an increase of metabolic activity in human fibroblasts in vitro, as measured by increased enzymatic activity using the MTT assay. Additionally, an increase in cell number in response to human ECM was detected. These results support the use of this human ECM as a coating/scaffold in embryonic cell cultures and as a biological surface coating/filler in various therapeutic applications or medical devices.

EXAMPLE 6

Human Extracellular Matrix (hECM) Coated Biomedical MATERIALS

ECM has been reported to create an environment conducive to rapid cell proliferation and healing without the formation of scars or adhesions. Using methods described herein, unique, embryonic like, human ECM (hECM) was generated by culturing neonatal fibroblasts in low oxygen and specific gravity. Results included: angiogenesis when hECM is placed on the chorioallantoic membrane, and reduced inflammatory cell migration when hECM is coated on nylon mesh and implanted on the flank position in the subcutaneous region of SCID mice. Based upon these results, it was hypothesized that coating our hECM on polypropylene mesh would illicit reduced inflammatory cell migration and fibrous encapsulation at the material-biological interface in the subcutaneous region of SCID mice.

ECM compositions generated using human derived materials (hECM) were coated onto propylene mesh using a photoactive crosslinker. hECM was coated on 6 mm biopsy punched polypropylene by UV covalent bonding mechanism (Innovative Surface Technologies (ISurTec) TriLite™ Crosslinker). Coated and uncoated hECM 6 mm biopsy punches of polypropylene were sterilized utilizing E-Beam™ (BeamOne LLC E-BEAM™) or ethylene oxide (ETO) (described by ETO Flagstaff Medical Center). Next, each 6 mm polypropylene disc was split into two symmetrical semi circular inserts. Finally, polypropylene implants were placed bilaterally utilizing aseptic technique on the flank position in the subcutaneous region. Samples were explanted at the two and five week endpoint for histology.

Anti-fibronectin immunofluorescent stains of hECM-coated polypropylene mesh showed that the ECM materials bound to and formed a uniform coating on the fibers of the mesh as compared to uncoated mesh. HECM coated mesh is suitable for implantable patches for medical applications, such as hernia repair and pelvic floor repair. The ECM materials were shown to coat the individual fibers of the mesh as shown through immunofluorescent staining with fibronectin antibodies which allows for improved cellular ingrowth.

hECM was implanted onto the chick chorioallantoic membrane (CAM) and stimulated a microvascular response as evidenced by new microvasculature growth. Additionally, hECM-coated nylon mesh subcutaneously implanted into mice for four weeks demonstrated improved biocompatibility versus uncoated nylon mesh. Specifically, fewer inflammatory cells and a thinner fibrous capsule were observed with the hECM-coated nylon fibers.

Figure 1B:
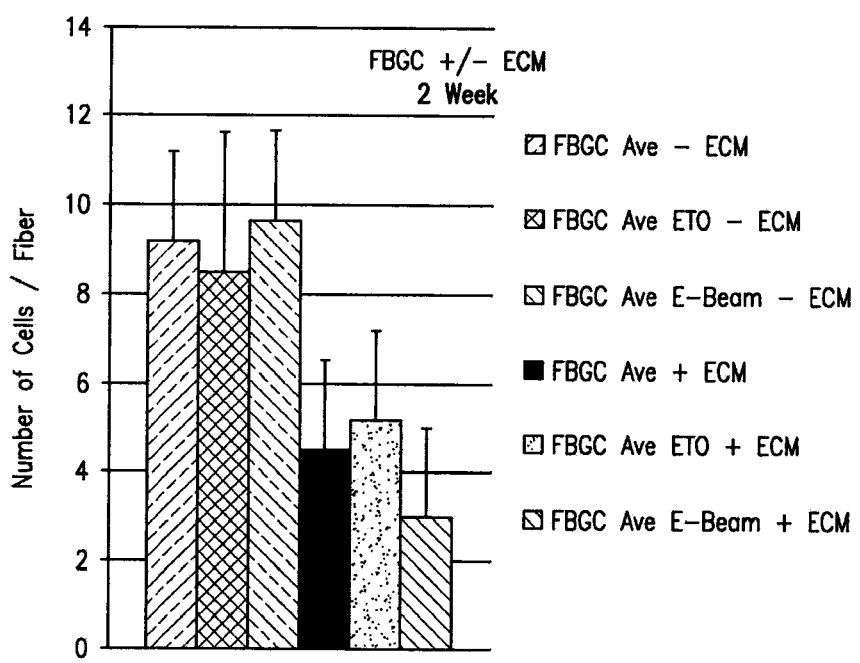
FIG. 1B shows the number of FBGCs per fiber 2 weeks after implantation for uncoated (columns 1-3) and ECM coated fibers (columns 4-6). * indicates p<0.05.
Figure 2A:
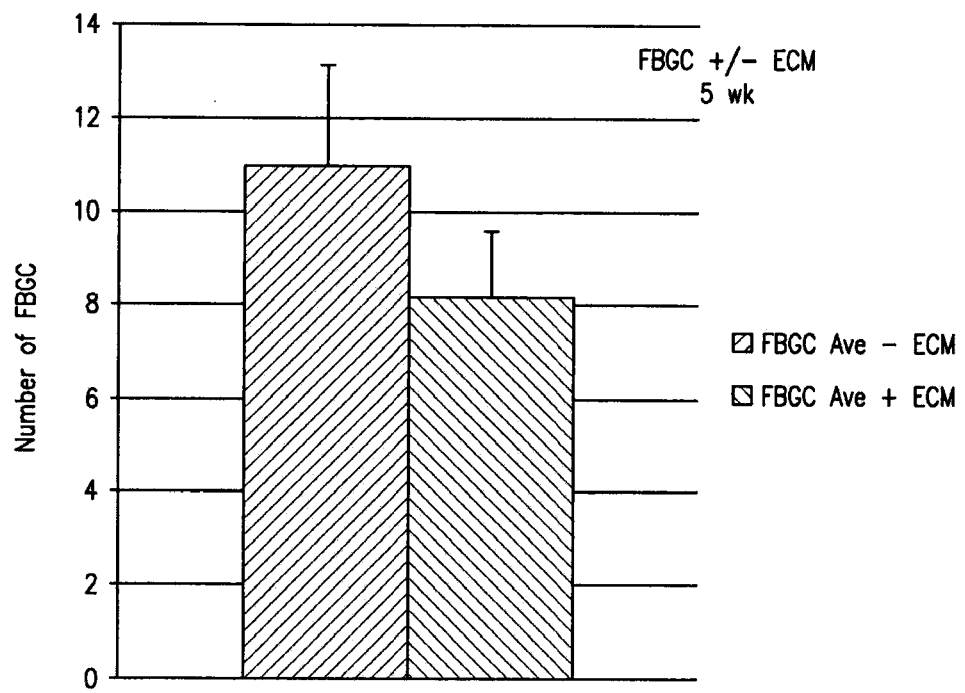
FIG. 2A shows the number of FBGCs per fiber 5 weeks after implantation for uncoated (first column) and hECM coated fibers (second column).
Figure 2B:
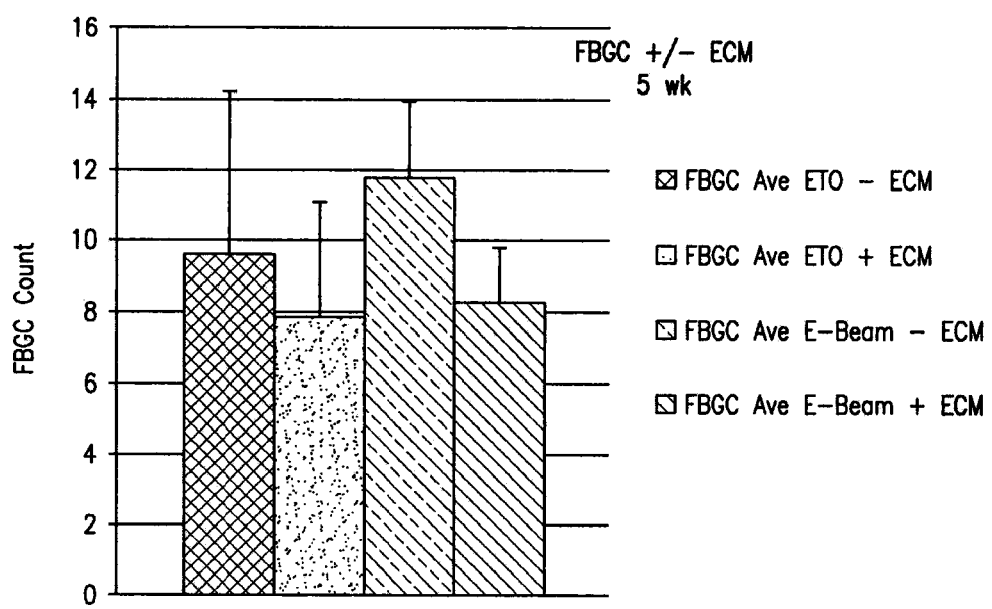
FIG. 2B shows the number of FBGCs per fiber 5 weeks after implantation for uncoated (columns 1 and 3) and hECM coated fibers (columns 2 and 4).
Figure 14A:
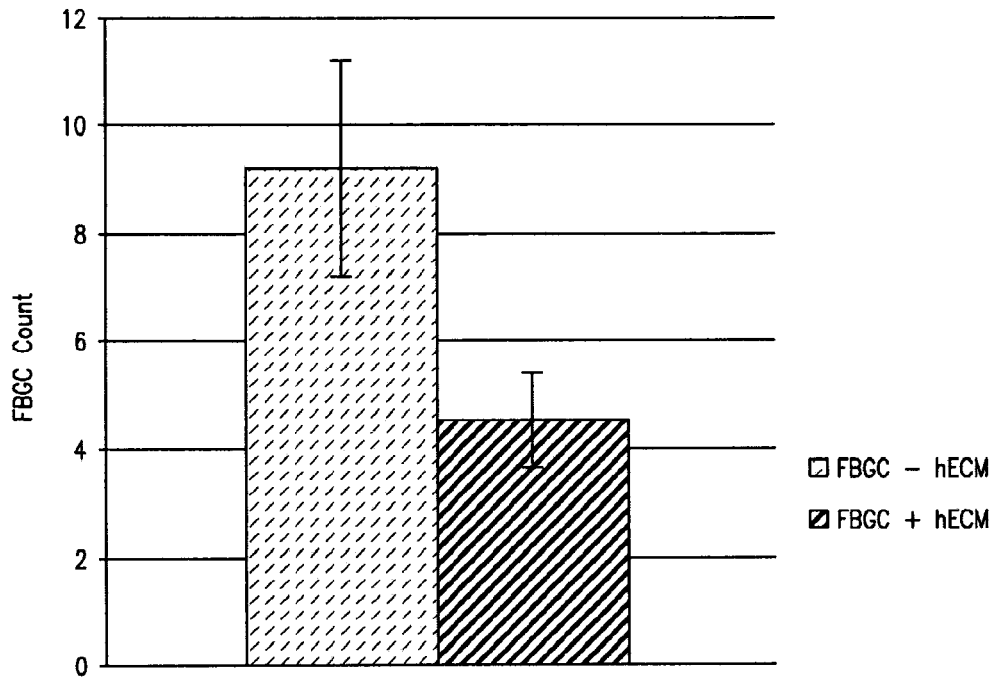
FIG. 14A shows the number of FBGCs per fiber 2 weeks after implantation for uncoated (first column) and hECM coated fibers (second column).
Figure 14B:
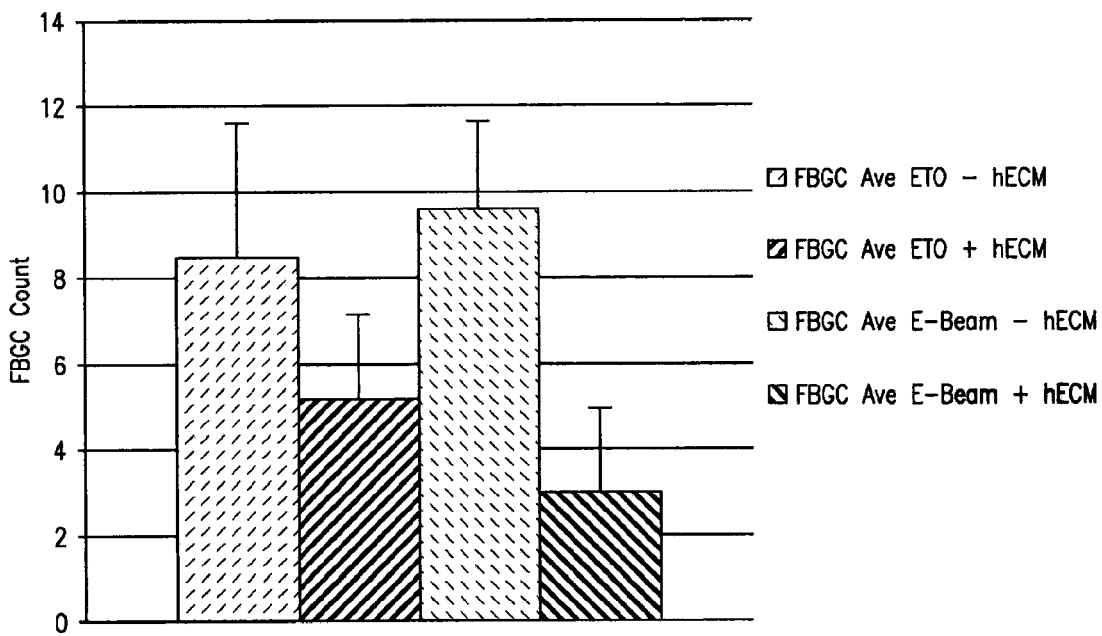
FIG. 14B shows the number of FBGCs per fiber 2 weeks after implantation for uncoated and ECM coated fibers.
Figure 15A:
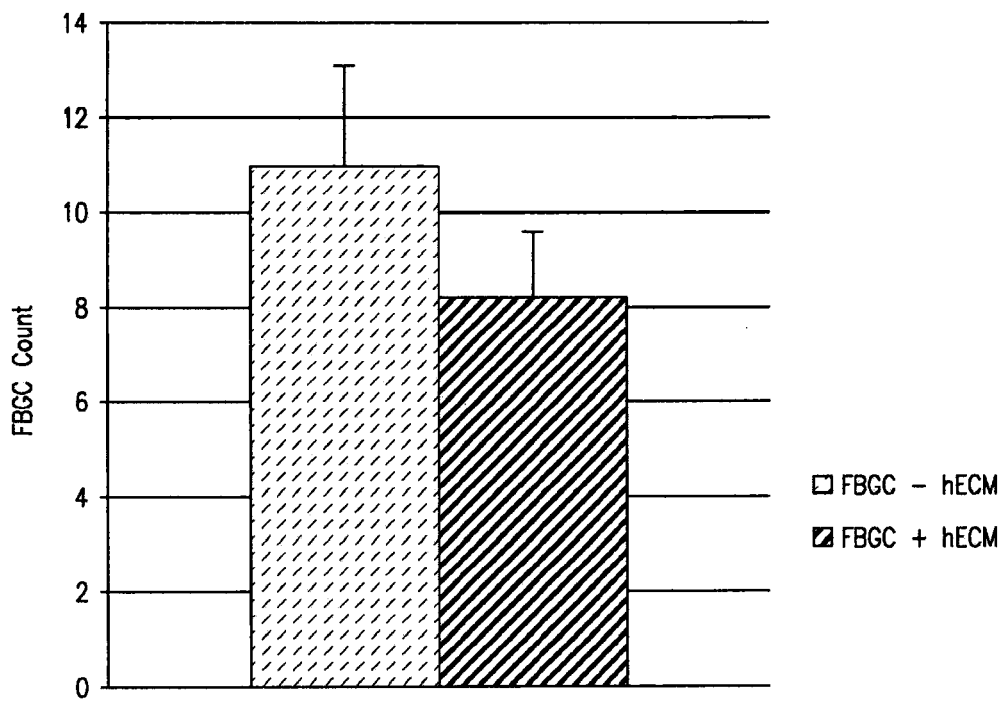
FIG. 15A shows the number of FBGCs per fiber 5 weeks after implantation for uncoated (first column) and hECM coated fibers (second column).
Figure 15B:
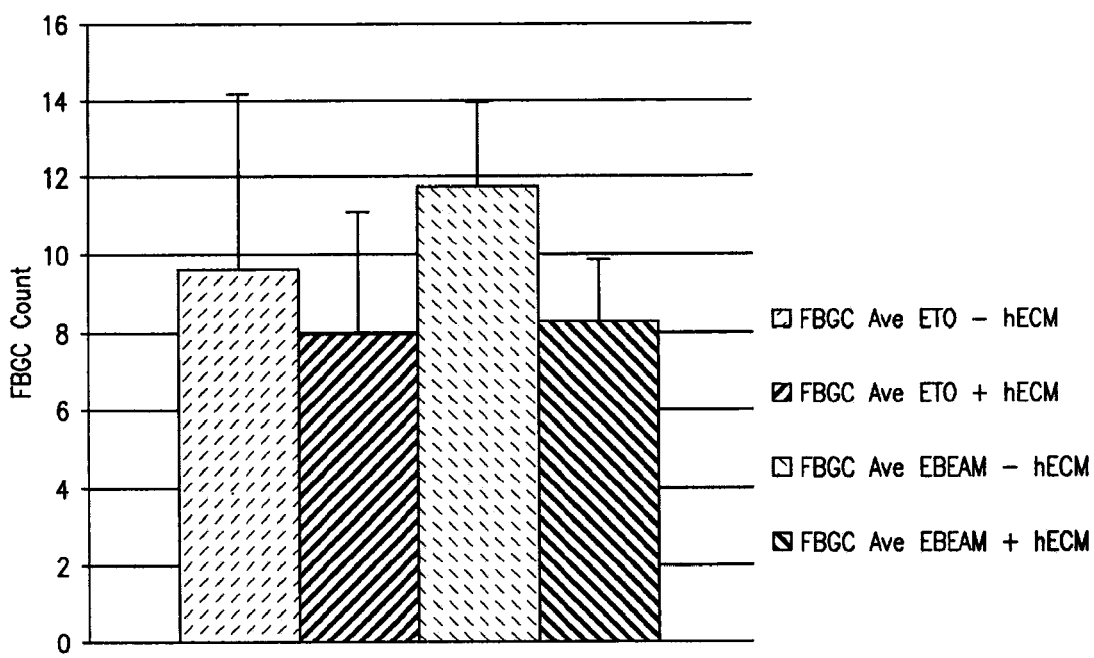
FIG. 15B shows the number of FBGCs per fiber 5 weeks after implantation for uncoated and ECM coated fibers.

Biocompatibility evaluations were performed at two weeks and five weeks after implantation of hECM coated polypropylene mesh using hematoxylin and eosin stained samples. For FBGC analysis samples were blind-coded, evaluated using morphometry, separated into groups, statistically evaluated, then decoded. The number of foreign-body giant cells (FBGCs) were examined. The number of FBGCs per fiber two weeks after implantation is shown in FIGS. 1A-B as well as additional samples in FIGS. 14A-B. The number of foreign-body giant cells per fiber five weeks after implantation is shown in FIGS. 2A-B as well as additional samples in FIGS. 15A-B. A reduction in FBGCs for hECM coated polypropylene mesh as compared with non-coated mesh is evident. At the two week time point the mean FBGC count per sample was determine to be statistically higher (ANOVA bonferroni post-hoc analysis $p<0.05$) for uncoated polypropylene (9.20+/−2.03) versus hECM coated polypropylene (4.53+/−0.89). At the five week time point the mean FBGC count per sample was determined to be higher, although not statistically significant, for uncoated polypropylene (10.95+/−2.15) versus hECM coated polypropylene (8.17+/−1.41).

Figure 16A:
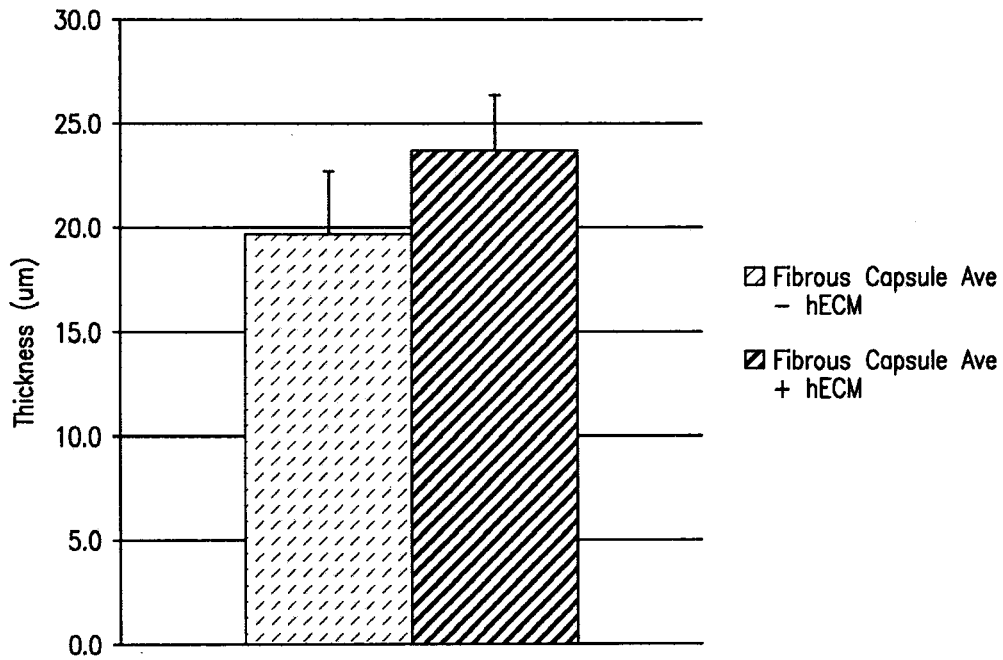
FIG. 16A shows the mean fibrous capsule thicknesses 2 weeks after implantation for uncoated (first column) and hECM coated fibers (second column).
Figure 16B:
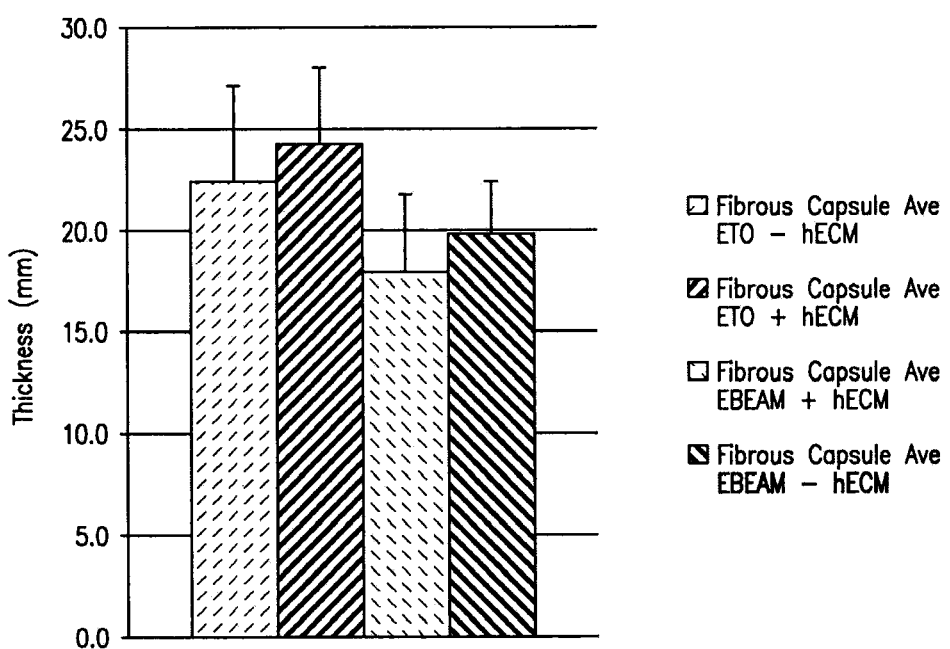
FIG. 16B shows the mean fibrous capsule thicknesses 2 weeks after implantation for uncoated and ECM coated fibers.
Figure 17A:
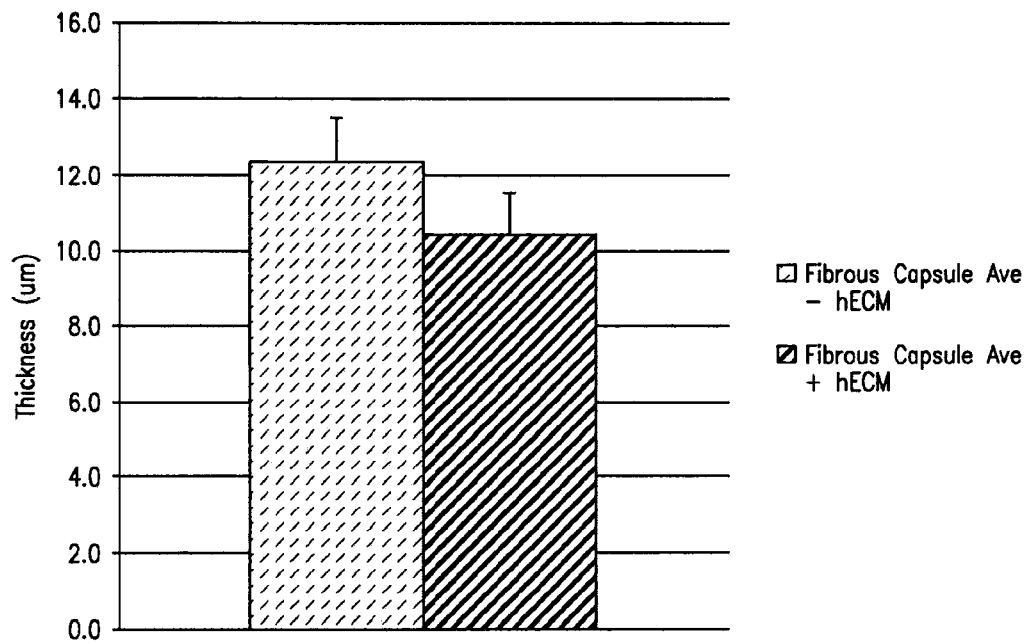
FIG. 17A shows the mean fibrous capsule thicknesses 5 weeks after implantation for uncoated (first column) and hECM coated fibers (second column).
Figure 17B:
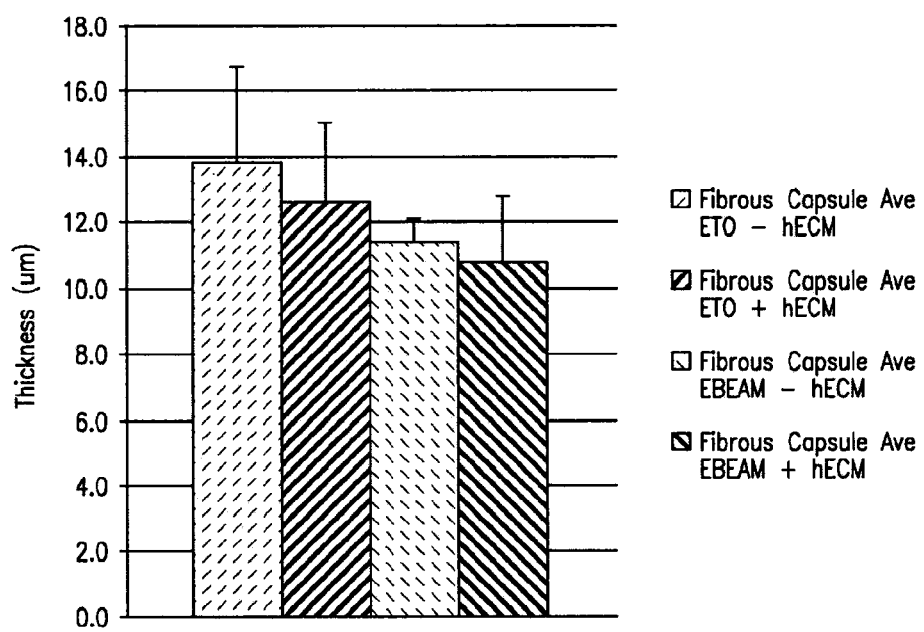
FIG. 17B shows the mean fibrous capsule thicknesses 5 weeks after implantation for uncoated and ECM coated fibers.

The results indicated hECM coated polypropylene may reduce fibrous capsules. Fibrous encapsulation was evaluated at the two and five week time point using Trichrome stained samples. For capsule analysis samples were blind-coded, evaluated using morphometry, separated into groups, statistically evaluated, then decoded. At the two week time point the mean fibrous capsule thickness was not determined to be statistically higher (ANOVA bonferroni post-hoc analysis $p<0.05$) for hECM coated polypropylene (23.70+/−2.70 uM), versus uncoated polypropylene (19.70+/−3.00 uM) (FIGS. 16A-B). At the five week time point, the mean fibrous capsule thickness was determined to be (10.40+/−1.10 uM) for hECM coated polypropylene, versus uncoated polypropylene (12.30+/−1.20 uM) (FIGS. 17A-B). Again, the differences in the hECM coated, versus uncoated polypropylene, were not determined to be statistically significant. Although, an important observation was found when evaluating the average percentage difference in fibrous encapsulation from the two to five week time points. The average percentage decrease in fibrous encapsulation from the two week to five week time points was 37.6% for hECM uncoated polypropylene, versus 56.1% for hECM coated polypropylene.

A mechanism of FBGC formation is the result of macrophage fusion in an immune response to implantable biomaterials such as polypropylene. These large multinucleated cells provide an effective means to quantitatively assess the inflammatory response to implantable biomaterials. A significant reduction in FBGC count per sample with human ECM coated versus uncoated polypropylene was observed at the two week time point. This data suggests that the human ECM surface coating may serve as an application for a variety of implantable devices.

Historically, the effectiveness and longevity of implantable devices have been challenged by specific immune responses including FBGC and fibrous capsule formation. Specifically FBGCs can excrete degradative agents such as superoxides and free radicals, as well as other degradative agents challenge device effectiveness, and longevity. These negative effects are especially significant since FBGCs are known to remain localized immediately around the implant for the duration of the presence of the implant. Fibrous capsule formation, which arises as a firm vascular collagen encapsulation around an implant, is designed to isolate foreign implantables from the host or host tissue. This response not only may cause discomfort for the patient in certain cases, but may shorten length of device viability and even diminish device effectiveness. Thus a coating that reduces FBGC and fibrous encapsulation is a highly desirable outcome for the longevity and function of implantable devices.

Findings that coating hECM on polypropylene will reduce FBGC presence, and potential reduction in fibrous encapsulation at the material-biological interface supports the need for further experimentation. Future evaluation may include time points of a longer duration to observe the changes in thickness of fibrous encapsulation with hECM coated and uncoated biomaterials. Additionally, evaluation with a continuum of biomaterials including dacron, nylon, stainless steel, and titanium in various in vivo environments, may elucidate further desirable hECM coated biomaterial outcomes.

EXAMPLE 7

Use of Extracellular Matrix Compositions for Stimulation of HAIR GROWTH

This example illustrates the stimulation of hair growth by administration of ECM compositions.

Figure 3A:
Figure 3B:
FIG. 3B is an image of control follicle cells.

Human hair follicle cells and cells taken from hair follicles were obtained to determine the ability of the ECM compositions described herein to stimulate and maintain hair forming ability. Hair follicle cells were obtained from Alderans Research International. Cells were cultivated in the presence of ECM. Analysis of the cells at four weeks and eight weeks of culture showed structures that resembled hair follicles as well as structures that resembled hair shafts as shown in FIGS. 3A and B. After two months of continuous culture, the cells remained alive and growing.

Cells cultured for four weeks in the presence of ECM composition were transplanted into mice. Four weeks after transplantation the cultured human hair follicles formed many large follicles as compared to control cells which showed only normal numbers of small resting hair follicles as observed using microscopic image analysis.

Based on these findings an in vivo hair growth trial was performed using human subject to determine de novo follicular hair regeneration. The study enrolled 24 men from the ages of 18 to 45 years having male pattern hair loss (MPHL). All members of the study group were without prior invasive or minimally invasive topical scalp surgery or topical treatment with Minoxidil™ or Finasteride™. A Palomar Starluz 550p laser was used (1540-non-ablative and 2940 ablative). Study duration was designed upwards to 12 months for follow-up, baseline, and 5 months (following single sc injection). Following injection a three day wash-out period was observed and subjects only used Cetaphil™ shampoo throughout study. A combination of lasing and microdermabrasion was performed prior to injection.

Subjects were administered vehicle admixed with hECM determined to have wnt protein activity and to include wnt 7a transdermally along with control vehicle and saline. End points of the study included a 7 point clinical grading system (3 blinded hair transplant surgeons), clinical macrophotography (follicle counts), 2 mm punch biopsies and subject self assessment questionnaires.

Figure 18:
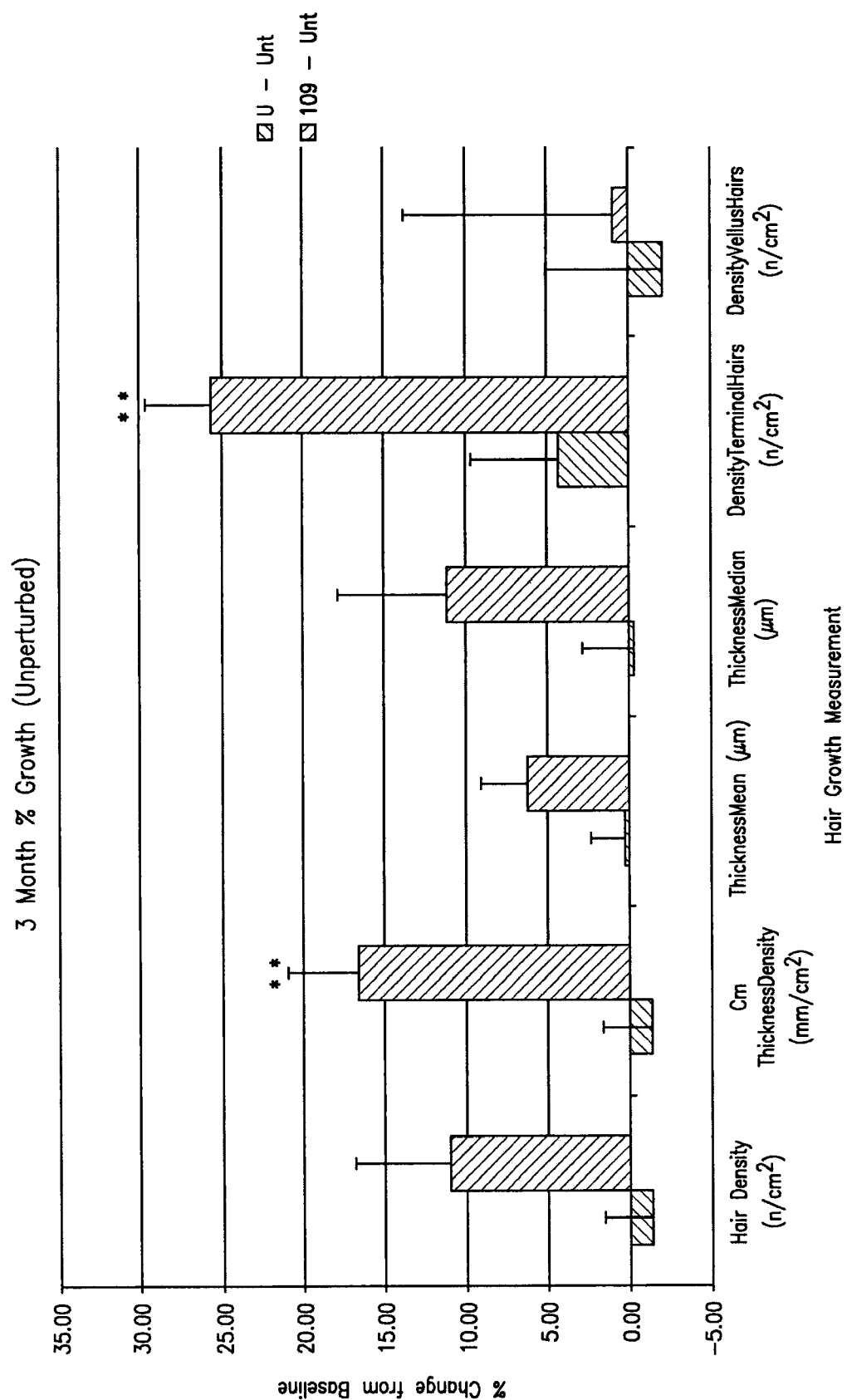

Individual follicular units were analyzed for subjects. The follicles were counted at 12 weeks and compared to the baseline observed for the same individual at the start of the study. Increases in follicular units were observed in subjects administered hECM without perturbation. For example, in one subject, treatment increased the number of apparent hair follicles from a baseline of 217 to 265 at 12 weeks. Total hair counts for the subject showed an increase from 307 to 360, an approximately 20% increase overall. The following increases in follicular counts were observed in other subjects as follows: subject 009 (baseline hair count 179, 12 weeks hair count 193, 5 month hair count 201); subject 013 (baseline hair count 266.5, 12 weeks hair count 267, 5 month hair count 294); subject 024 (baseline hair count 335.5, 12 weeks hair count 415, 5 month hair count 433). Further, 12 out of 13 patients (92.3%) administered hECM in the study showed efficacy at 12 weeks. FIG. 18 shows additional hair growth measurements at 3 months.

Additional results are shown in FIGS. 19 and 20 showing hair growth characteristics for 2 test subjects at 12 and 22 weeks respectively.

Additional hair parameters were analyzed throughout the study. At 12 weeks and 20 weeks relative hair count was analyzed as compared to baseline (0 weeks), terminal hair was analyzed as compared with baseline, and hair thickness was analyzed as compared with baseline. For example, in one subject, treatment increased hair count, terminal hair and follicle thickness, at 12 weeks, 22.4%, 27.8% and 23.9% respectively as compared to baseline. In another subject, treatment increased hair count, terminal hair and follicle thickness, at 12 weeks, 23.7%, 24.2% and 22.2% respectively as compared to baseline. In subject 009 (having baseline hair count 179, 12 weeks hair count 193, 5 month hair count 201, as above) treatment increased hair count, terminal hair and follicle thickness, at 12 weeks, 7.8%, 48.5% and 19.2% respectively; and, at 20 weeks, 12.9%, 33.0% and 21.1% respectively, as compared to baseline. In subject 013 (having baseline hair count 266.5, 12 weeks hair count 267, 5 month hair count 294, as above) treatment increased hair count, terminal hair and follicle thickness, at 12 weeks, 0.2%, 25.0% and 8.3% respectively; and, at 20 weeks, 10.3%, 41.4% and 23.0% respectively as compared to baseline. In subject 024 (baseline hair count 335.5, 12 weeks hair count 415, 5 month hair count 433 as above) treatment increased hair count, terminal hair and follicle thickness, at 12 weeks, 23.7%, 24.2% and 22.2% respectively; and, at 20 weeks, 29.1%, 5.9% and 17.3% respectively as compared to baseline respectively.

Figure 21A:
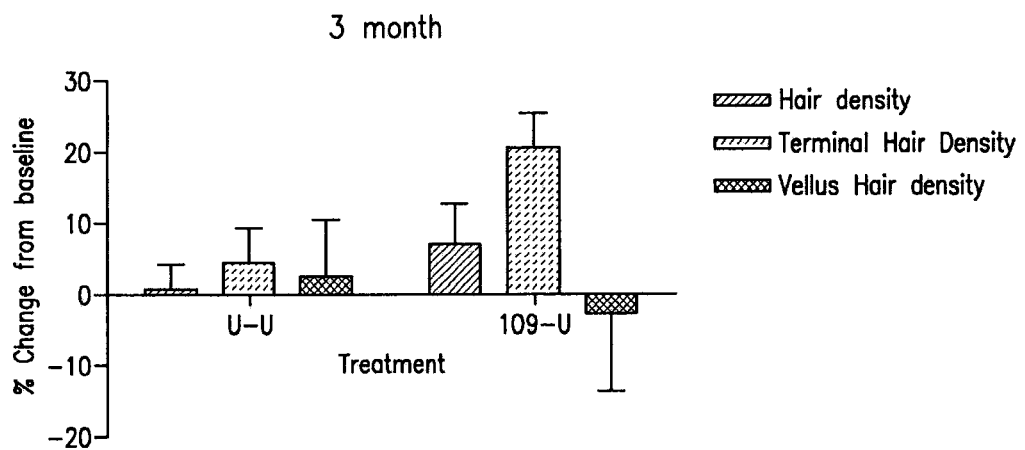
FIG. 21A shows the results at 3 months.
Figure 21B:
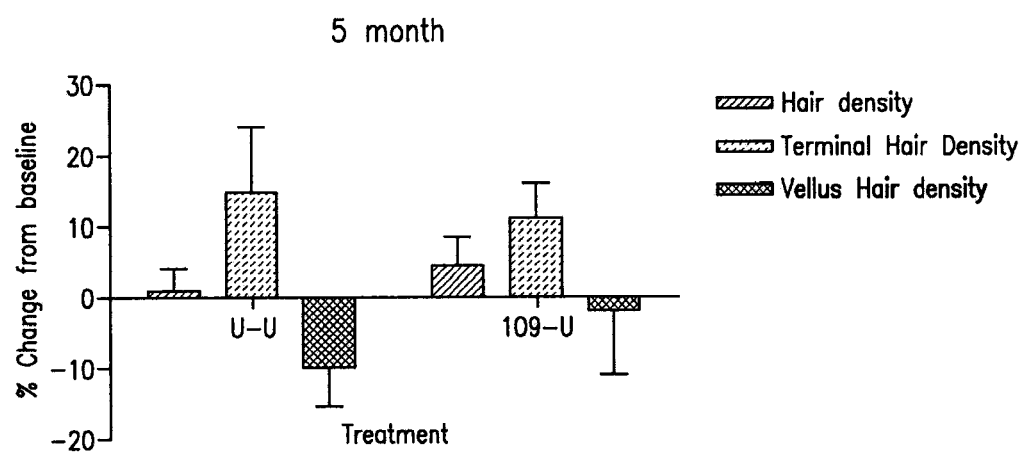
FIG. 21B shows the results at 5 months.
Figure 22A:
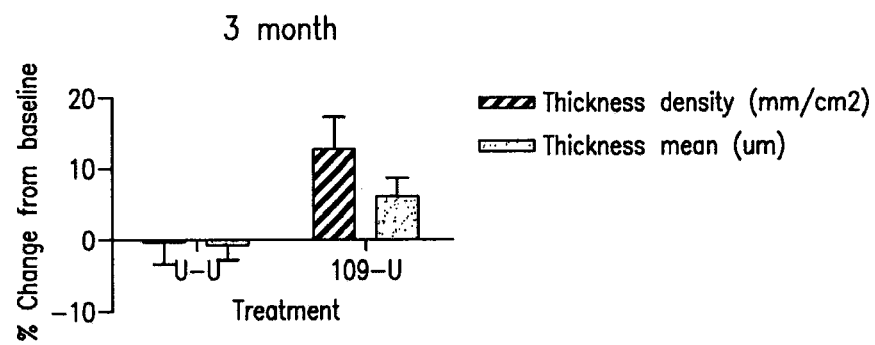
FIG. 22A shows the results at 3 months.
Figure 22B:
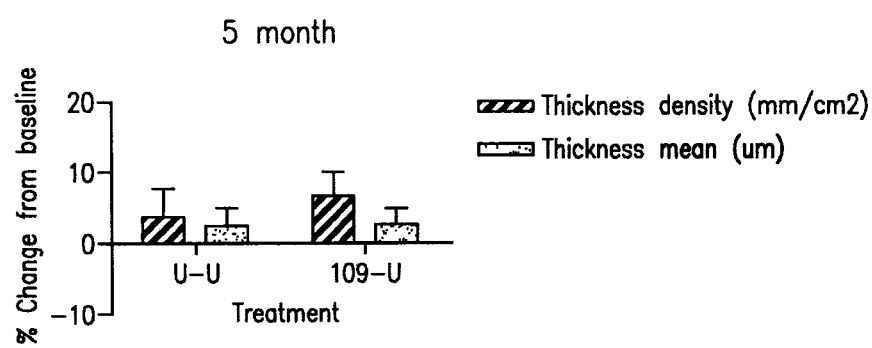
FIG. 22B shows the results at 5 months.
Figure 23:
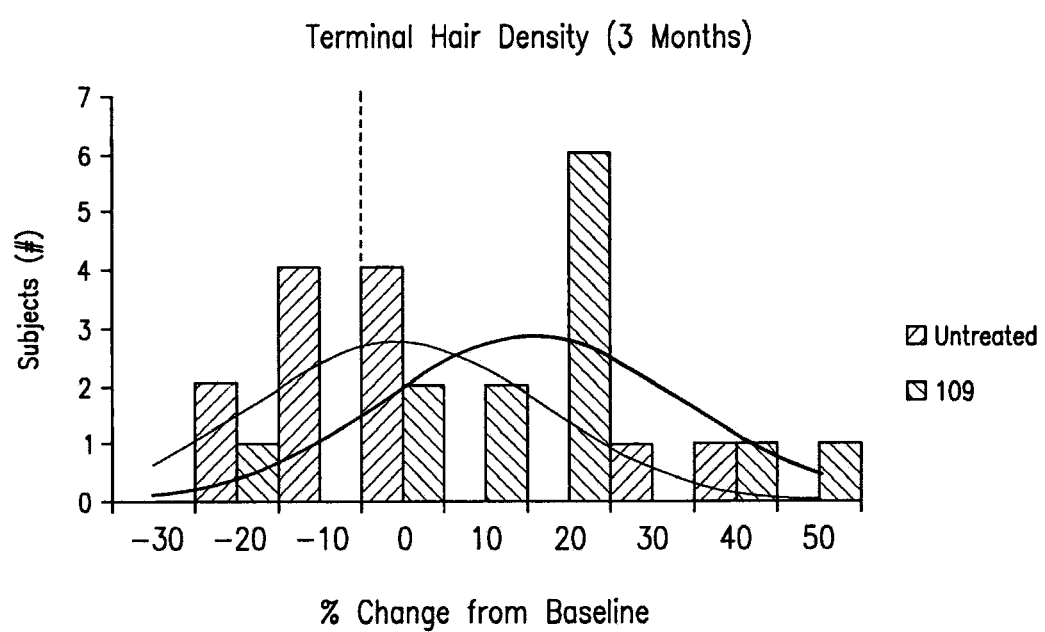
FIG. 23 shows a graphical representation of the distribution of subject responses as measured by terminal hair density to hECM treatment at 3 months.
Figure 24:
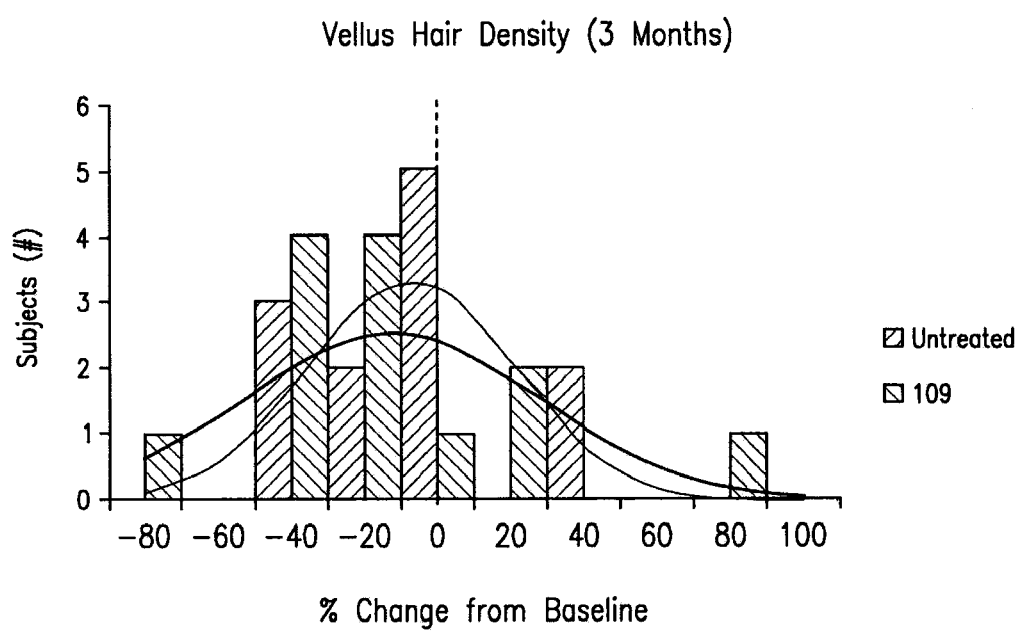
FIG. 24 shows a graphical representation of the distribution of subject responses as measured by vellus hair density to hECM treatment at 3 months.
Figure 25:
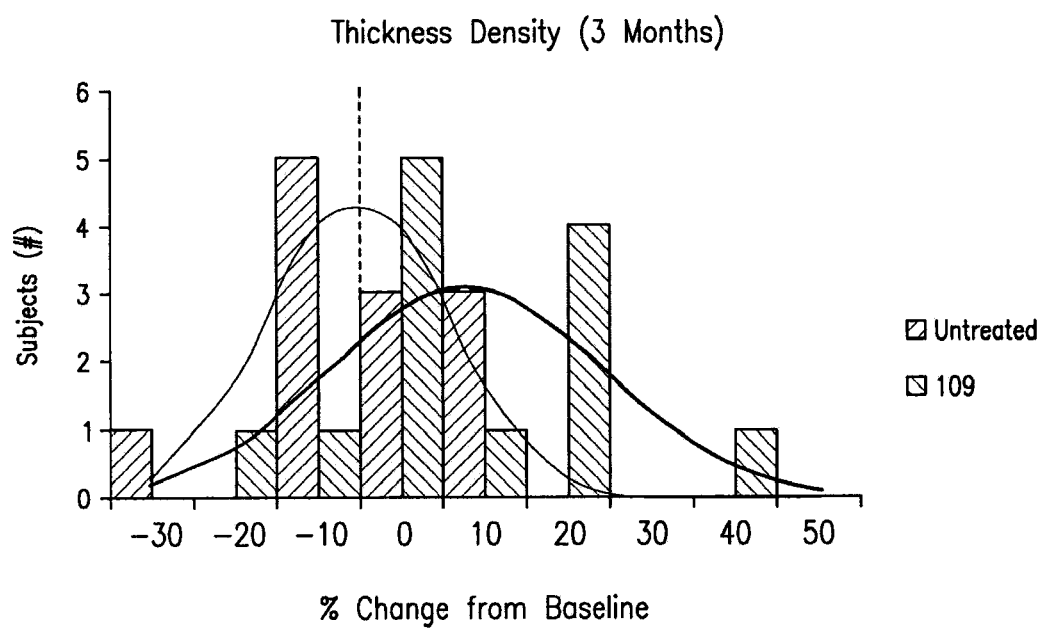
FIG. 25 shows a graphical representation of the distribution of subject responses as measured by thickness hair density to hECM treatment at 3 months.
Figure 26:
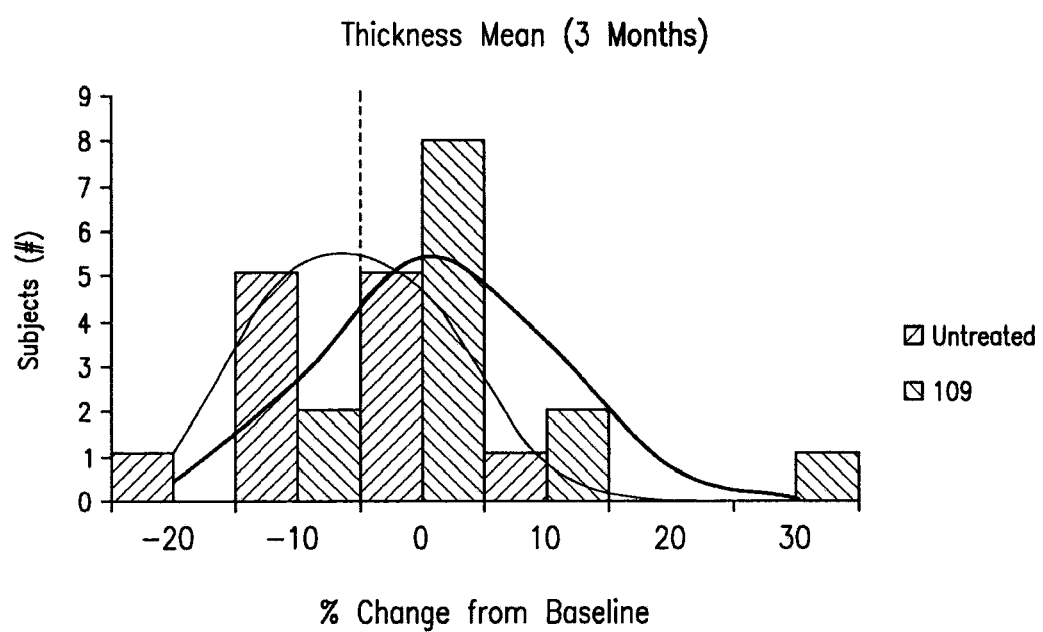
FIG. 26 shows a graphical representation of the distribution of subject responses as measured by thickness hair mean to hECM treatment at 3 months.

The aggregate results for 13 study members are shown in FIGS. 21 and 22. The distribution of study member responses at 3 months is shown in FIGS. 23-26.

Of note, treated study members showed a significant increase in the number of terminal hairs and increase in thickness density at 3 months (84.6% of pts). Additionally, no adverse reactions observed, normal histology was observed and no hamartomas were observed.

The results point to use of hECM in additional applications, such as to prevent hair loss in patients post transplant and for eyebrow and eyelash growth. In hair transplant patients, hair is known to fall out and generally take 4 to 5 months to return, thus, treatment with hECM would prevent hair loss in such individuals post transplant.

EXAMPLE 8

Generation of Human Extracellular Matrix Compositions (hECM)

Human ECM composition was generated using newborn human fibroblasts. Fibroblasts were seeded onto beadlike structures conditioned with liquid media. Culture conditions were optimized without the need for fetal bovine serum. Within a few days, under embryonic culture conditions described herein, cells produced a dense embryonic-like ECM. Secretion of Wnt family proteins, as well as several growth factors was observed.

Cultures were grown to confluency. The cultures were subsequently exposed to sterile water to induce uniform lysing of the cells. The acellular hECM was then washed to ensure removal of all living cells and cellular debris and examined microscopically to confirm removal of cellular debris. Next, human fibroblasts were exposed to culture flasks coated with the hECM or plated onto a non-treated flask and then covered with a thick layer of matrix. The ECM proteins identified in the hECM are shown in Table 7.

TABLE 7

Extracellular Matrix Proteins Observed in hECM

| Matrix Protein | Function |
|---|---|
| Versican | structural, binds hyaluronic acid (HA) and collagen |
| Decorin | binds growth factors, influences collagen structure |
| Betaglycan | TGF-$\beta$ Type III receptor |
| Syndecan | binds growth factors, enhances activity |
| Collagen Type I, II, III, V | major structural proteins of dermis |
| Fibronectin | cell adhesion, spreading, migration, motogenesis |
| Tenascin | induced in wound healing, control of cell adhesion |

Figure 4:
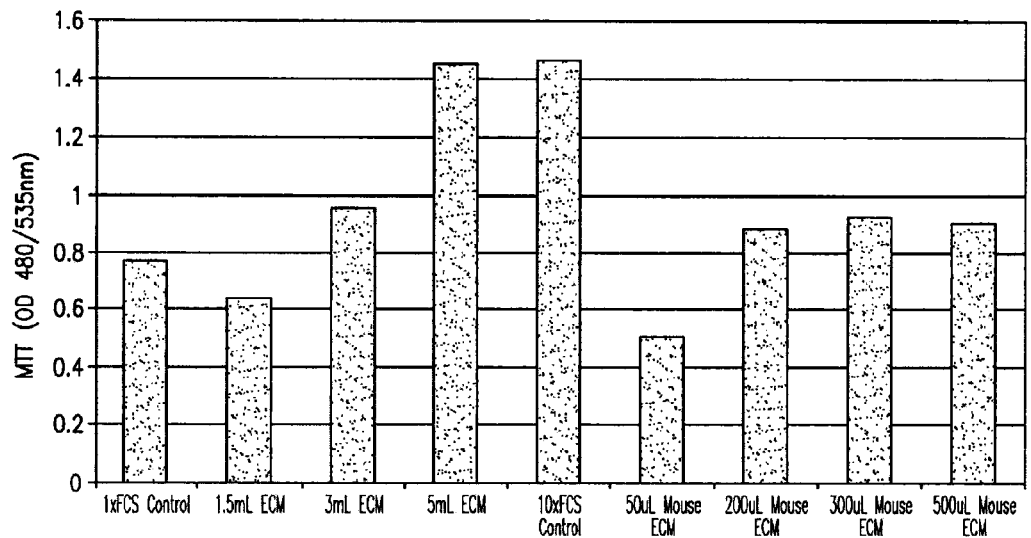
FIG. 4 shows a graphical representation of fibroblastic metabolic response to extracellular matrix compositions (both mouse ECM and human ECM) as shown by MTT assay.
Figure 5:
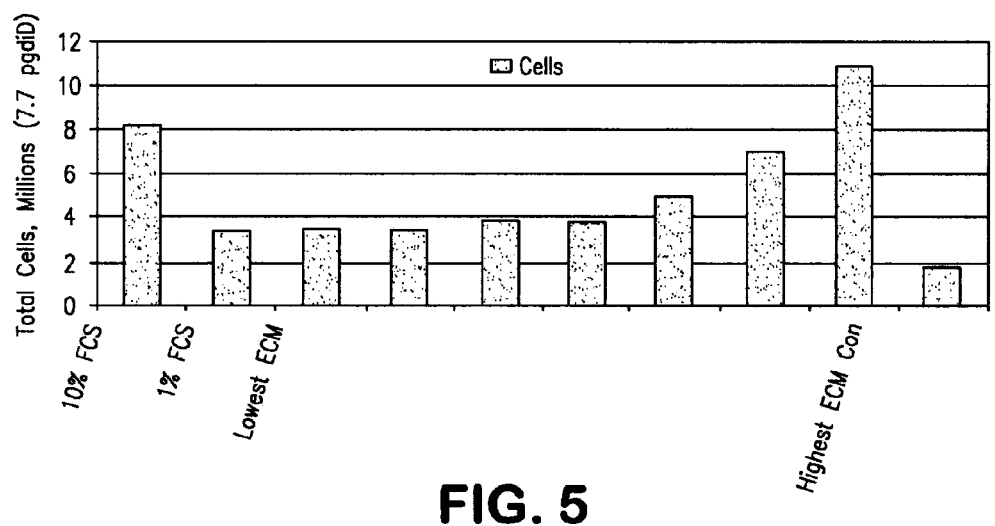
FIG. 5 is a graphical representation of cell number in response to human fibroblast exposure to hECM as measured by the Pico Green Assay.

The hECM was observed to induce an increase of metabolic activity of the cells, as measured by increased enzymatic activity using the MTT assay as shown in FIG. 4. Human ECM, unlike mouse ECM, induced a dose-dependant increase in cellular metabolic activity as measured by MTT assay. Cells were observed to rapidly and uniformly infiltrate the hECM overlay material. In addition, there was a dose-dependant increase in cell number in response to hECM, as measured by the Pico Green assay as shown in FIG. 5.

Known coatings, injectables, and implantable matrix products are typically either bovine collagens, porcine matrix proteins derived from the intestines or urinary bladder, hyaluronic acid, or human ECM derived from cadaver skin. While these products may offer benefits by creating a more physiologically equivalent environment, none are completely human and contain the entire range of matrix proteins found in young, developing tissue. The hECM produced contains the same ECM materials found in young, healthy tissue. It also was observed to support the active proliferation of human cells as well as rapid in-growth of cells. There are several advantages evident in using hECM in applications involving a human subject. For example, hECM promotes rapid host cell integration and improved healing (acts as normal scaffold for host cells and subsequent remodeling). Additionally, hECM eliminates the concern regarding viral transmission from non-human animal and human tissues (particularly BSE from bovine tissue and TSE from human tissue). Further, consistent product composition and performance is observed for hECM as compared to biologic products, particularly human dermis and fascia lata. Additionally, hECM reduces erosion of host tissues as compared to synthetic implants.

EXAMPLE 9

Human Fibroblast Derived Hypoxic Conditioned Extracellular Matrix for Medical Aesthetic Applications A double blind, randomized study of topical hECM administration post facial ablative laser surgery was conducted. The study enrolled 41 subjects between the ages of 40 and 60 years of age. All members of the study group were without prior invasive or minimally invasive surgery, or topical anti-aging treatments within the prior 12 months. The laser procedure included full fractional ablative laser procedure, peri-ocular, peri-oral and full face. A Palomar Starluz 550p laser was used (1540-non-ablative and 2940 ablative). Subjects were administered topical hECM compositions once a day (at different concentrations) or placebo vehicle for 14 days. End points of the study included clinical photography (3 blinded evaluations—dermatologists), transepidermal water loss (TEWL), punch biopsy, and evaluation of erythema, edema, and crusting.

Figure 6:
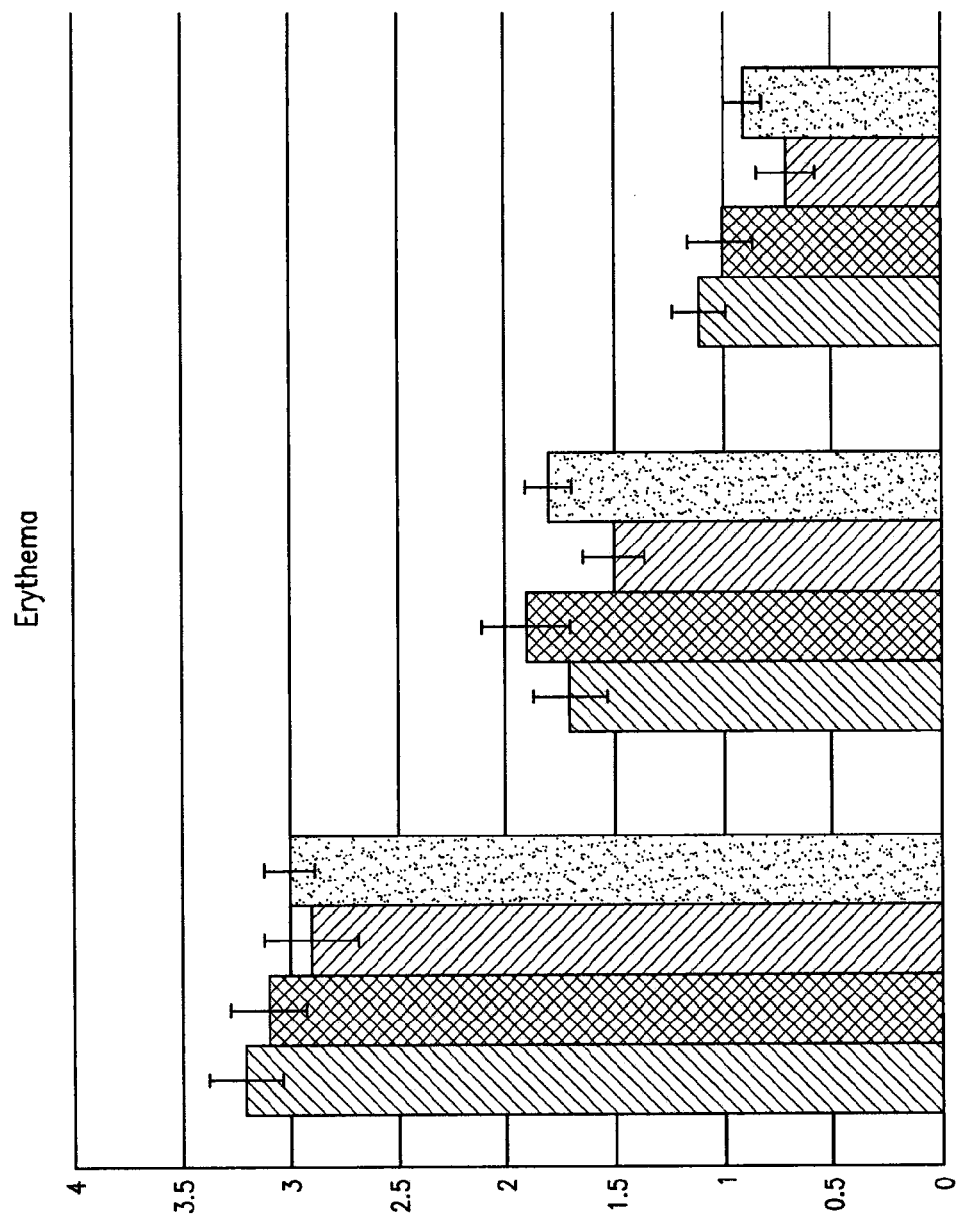
FIG. 6 is a graphical representation of erythema evaluations for 41 human subjects taken at 3, 7 and 14 days post laser treatment. The severity of erythema was evaluated on a scale of 0 (none) to 4 (severe). Each group of 4 data sets (0.1× hECM, 1×hECM, 10×hECM, and control from left to right) represents evaluations at day 3 (left), 7 (middle) and 14 (right).
Figure 7:
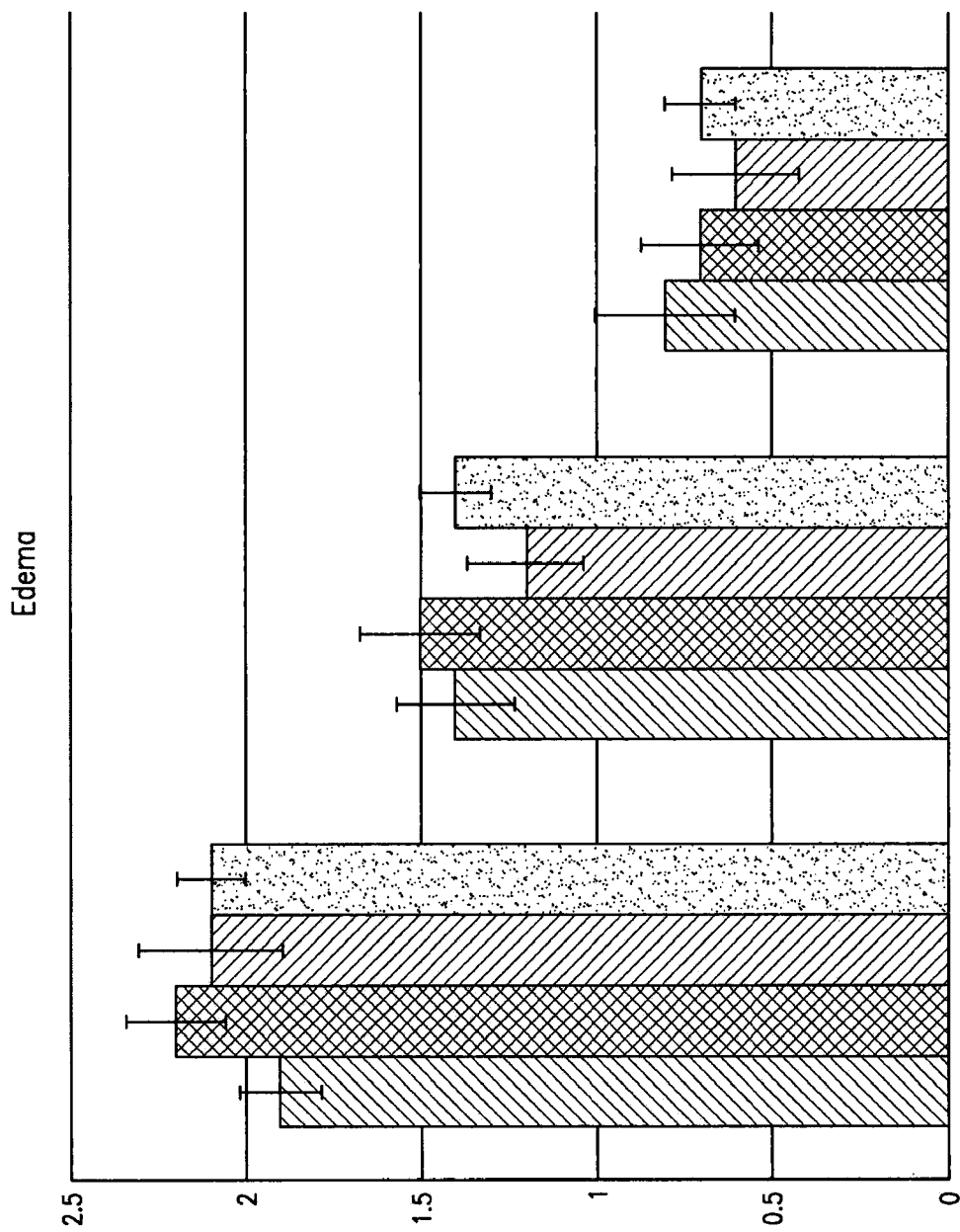
FIG. 7 is a graphical representation of edema evaluations for 41 human subjects taken at 3, 7 and 14 days post laser treatment. The severity of erythema was evaluated on a scale of 0 (none) to 2.5 (severe). Each group of 4 data sets (0.1× hECM, 1×hECM, 10×hECM, and control from left to right) represents evaluations at day 3 (left), 7 (middle) and 14 (right).
Figure 8:
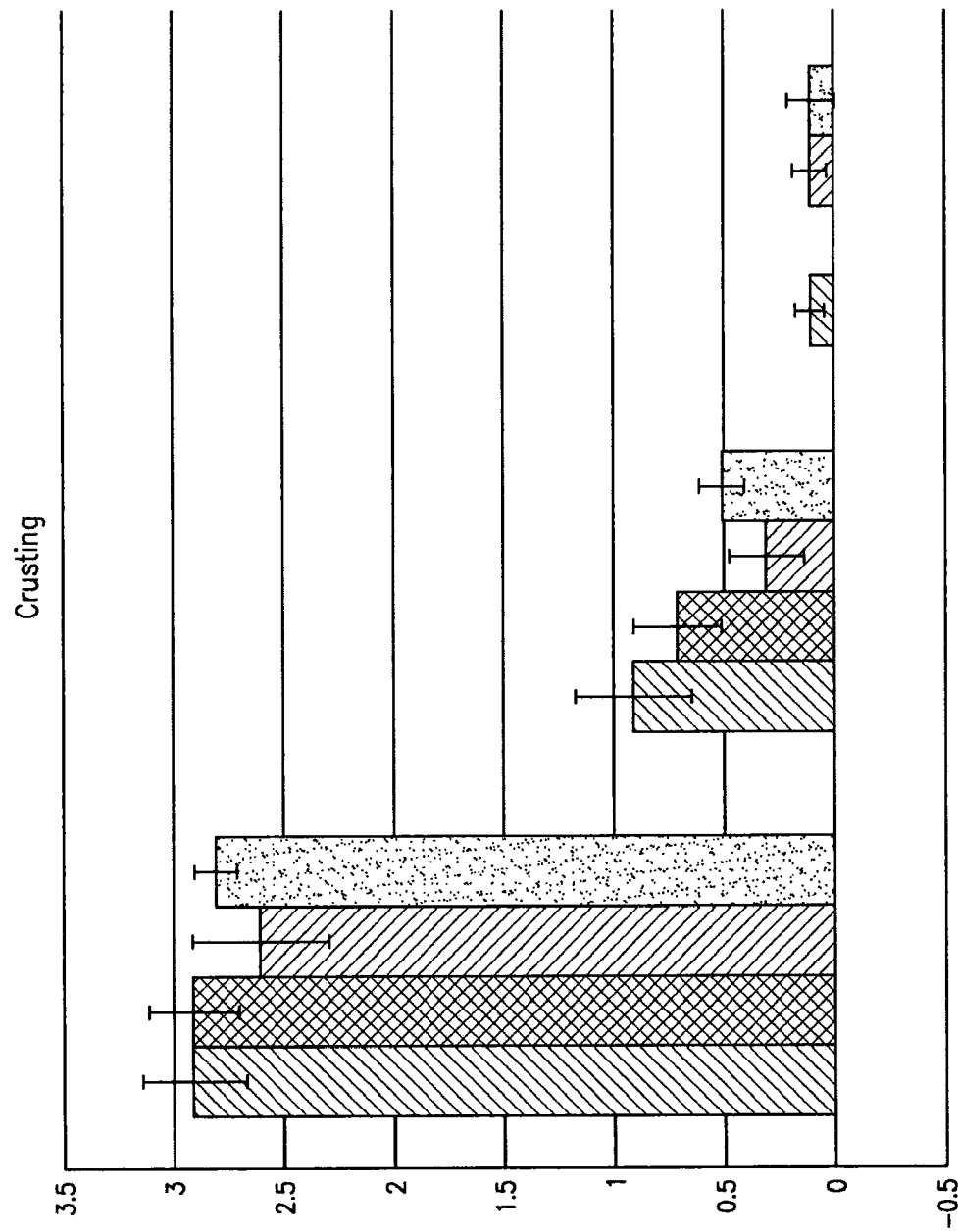
FIG. 8 is a graphical representation of crusting evaluations for 41 human subjects taken at 3, 7 and 14 days post laser treatment. The severity of erythema was evaluated on a scale of 0 (none) to 3.5 (severe). Each group of 4 data sets (0.1× hECM, 1×hECM, 10×hECM, and control from left to right) represents evaluations at day 3 (left), 7 (middle) and 14 (right).

The 10× strength hECM composition provided the most clinical improvement in symptoms as compared to the vehicle control (evaluations were conducted "blindly" by two cosmetic dermatologists, unrelated to any conduct of the clinical study). The results are shown in FIGS. 6 (erythema), 7 (edema), and 8 (crusting). Photographic evaluation also indicated a reduction of erythema severity in several patients at days 3, 7 and 14.

Figure 9:
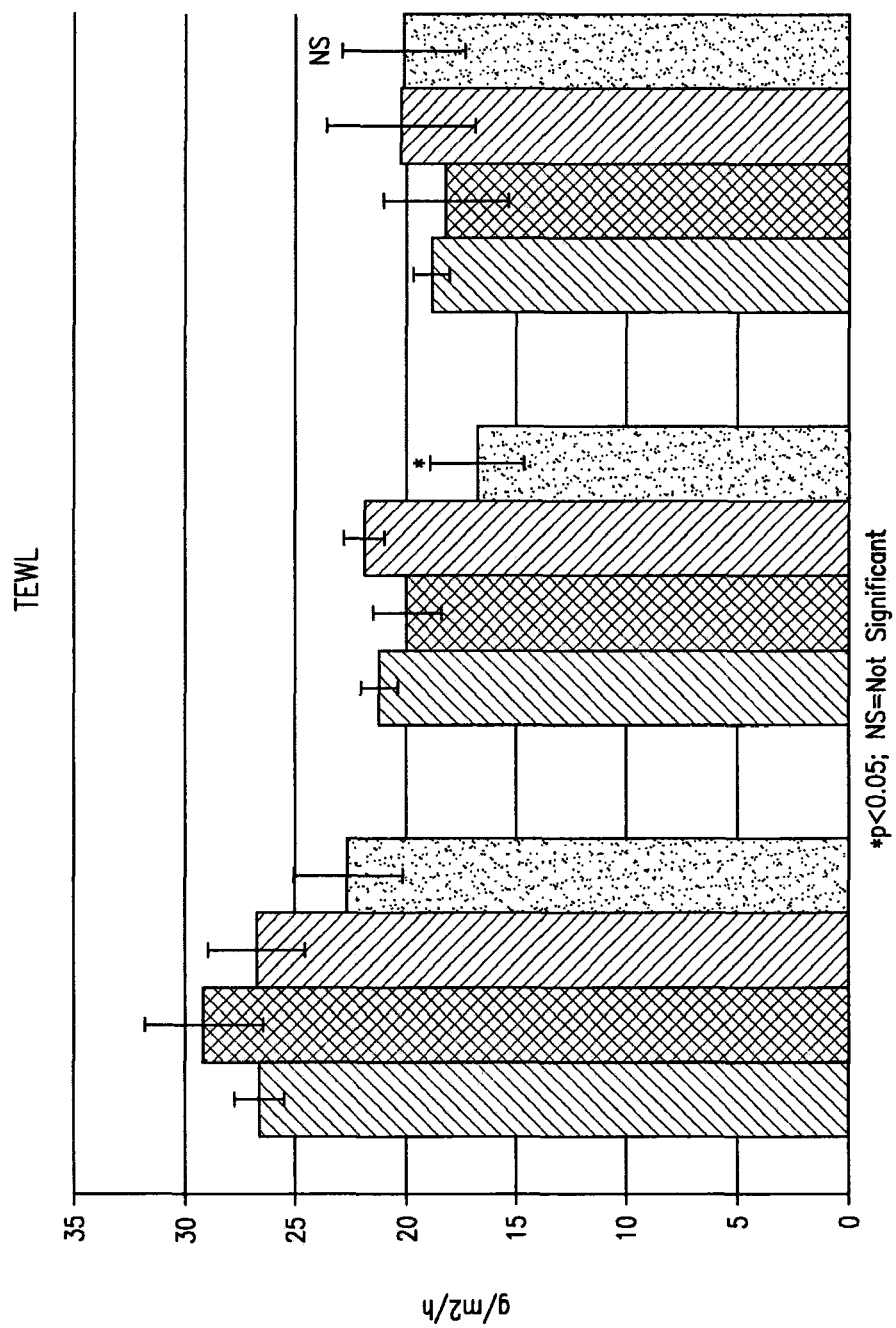
FIG. 9 is a graphical representation of transepidermal water loss (TWEL) values for 41 human subjects taken at 3, 7 and 14 days post laser treatment. The severity of TWEL was evaluated on a scale of 0 (none) to 4 (severe). Each group of 4 data sets (0.1×hECM, 1×hECM, 10×hECM, and control from left to right) represents evaluations at day 3 (left), 7 (middle) and 14 (right).

Transepidermal water loss (TEWL) values were also evaluated 3, 7, and 14 days post laser treatment for all 41 subjects. The results are shown in FIG. 9. The 10× strength hECM composition provided improvement in stratum corneum barrier function as noted at day 3, and day 7 as compared to the vehicle control. At day 7, the hECM composition is statistically significant at (p<0.05) as compared to the vehicle control. This observation is consistent with the fact that there were subjects at day 7 post ablative fractional laser treatment that were demonstrating reepithelialization.

A double blind, randomized study of topical hECM administration for anti-aging (e.g., wrinkle reduction) was also conducted. The study enrolled 26 subjects between the ages of 40 and 65 years of age. All members of the study group were without prior invasive or minimally invasive surgery, or topical anti-aging treatments within the prior 12 months. Subjects were administered topical hECM compositions twice a day or placebo vehicle for 10 weeks. Endpoints of the study included clinical photography (2 blinded cosmetic dermatologists), corneometer-surface hydration, cutometer-elasticity, punch biopsy, molecular evaluation (Epidermal Genetic Information Retrieval (EGIR)).

Photographic evaluation of the facial area indicated a generation of lighter pigmentation, smoother skin texture, more evenly toned skin, and a reduction in the appearance of fine wrinkles and lines after 10 weeks of hECM administration.

Figure 10:
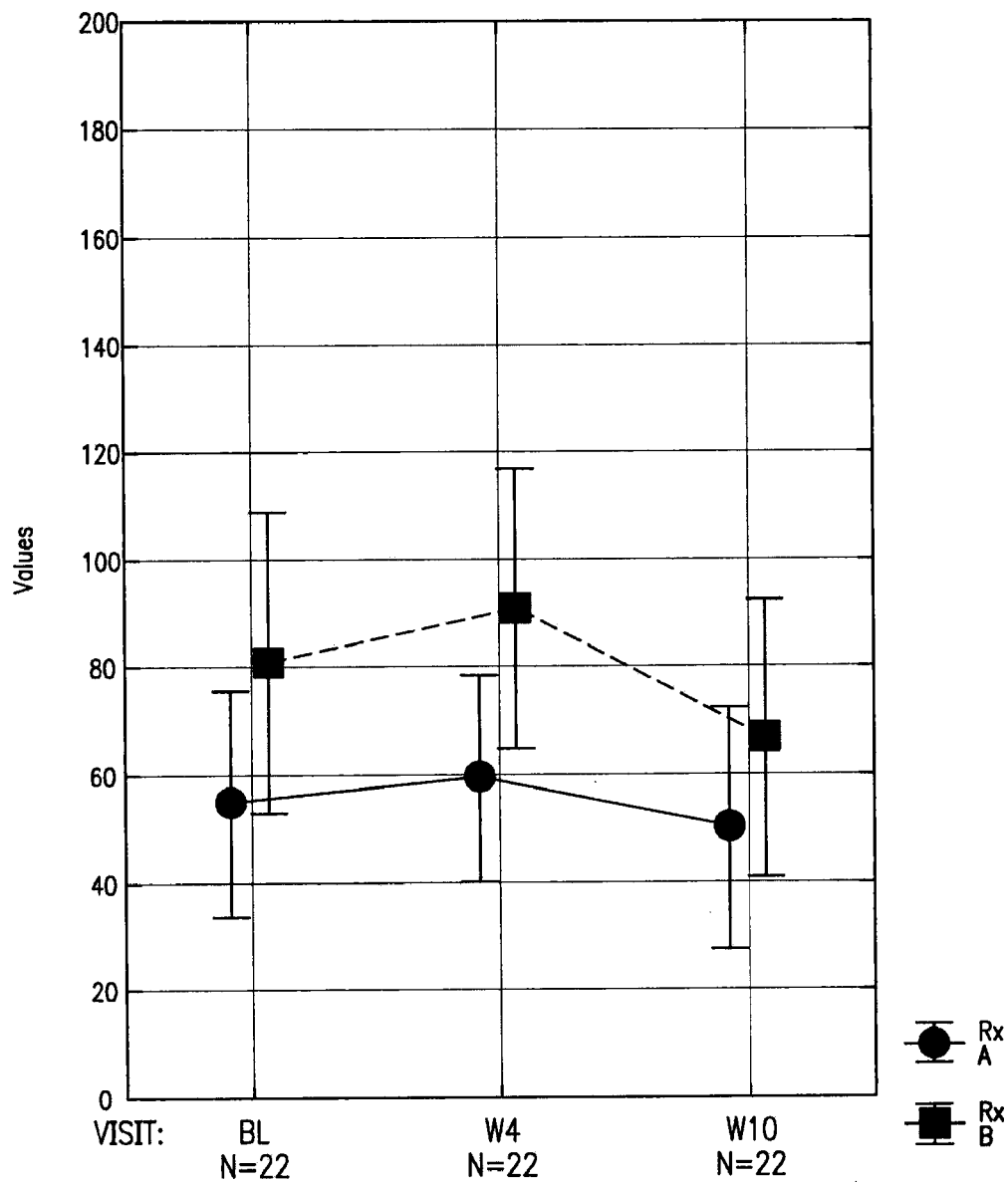
FIG. 10 is a graphical representation of three dimensional profilometry image analysis of silicon replicas from the periocular area. Data points were taken for 22 subjects before laser treatment, 4 weeks post treatment, and 10 weeks post treatment. Data series A represents values for hECM administration; data series B represents the control.

Three dimensional profilometry image analysis of silicon replicas of the peri-ocular area was also performed for 22 of the 26 subjects. To perform the analysis a collimated light source was directed at a 25° angle from the plane of the replica. The replica was placed in a holder that fixed the direction of the tab position of the replica so that the replica could be rotated to align the tab direction normal or parallel to the incident light direction. The replicas were taken from the crow's feet area adjacent to each eye with the tab direction pointing toward the ear. The normal sampling orientation provided texture measurements sensitive to the major, expression-induced lines (crow's feet). The parallel sampling orientation provided texture measurements sensitive to the minor, fine lines. The results are shown in FIG. 10.

A double blind, randomized study of topical hECM administration post facial ablative laser surgery was conducted. The study enrolled 49 subjects between the ages of 40 and 60 years of age. All members of the study group were without prior invasive or minimally invasive surgery, or topical anti-aging treatments within the prior 12 months. The laser procedure included full fractional ablative laser procedure, peri-ocular, peri-oral and full face. A Palomar Starluz 550p laser was used (1540-non-ablative and 2940 ablative). Subjects were administered topical hECM compositions twice a day or placebo vehicle for 14 days. End points of the study included clinical photography (3 blinded evaluations—dermatologists), mexameter and subject assessment.

Photographic evaluation of the facial area at days 1, 3, 5, 7 and 14 post surgery showed a clear reduction in erythema at every time point as compared to placebo.

Figure 11:
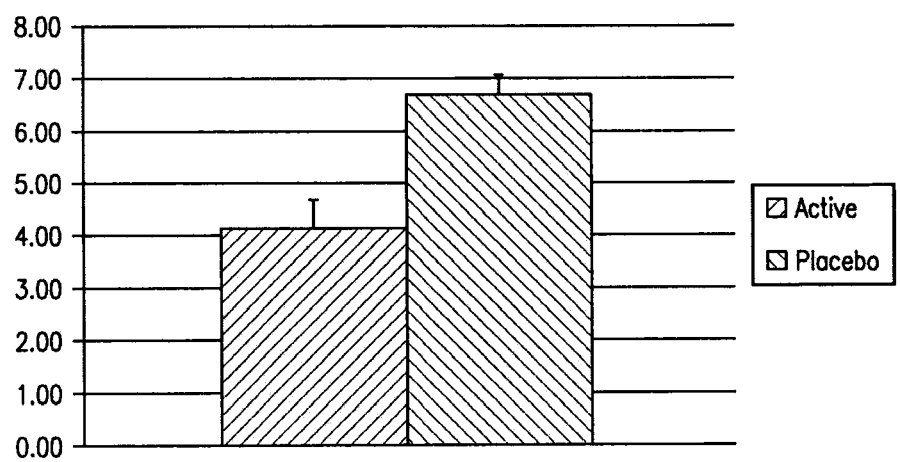
FIG. 11 is a graphical representation of analysis of petrolatum use post laser surgery.
Figure 12:
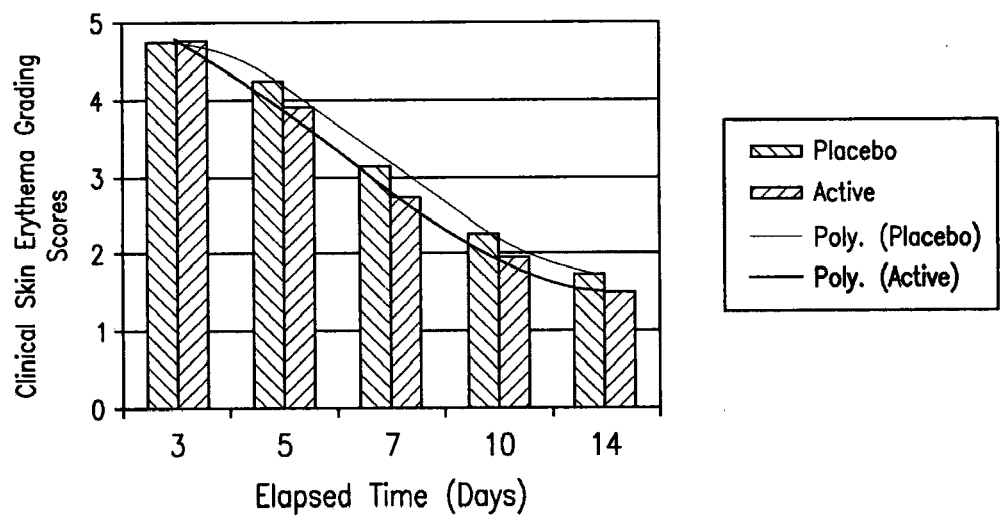
FIG. 12 is a graphical representation of analysis of skin erythema with data points taken at days 0, 3, 5, 7, 10 and 14 post laser surgery.
Figure 13:
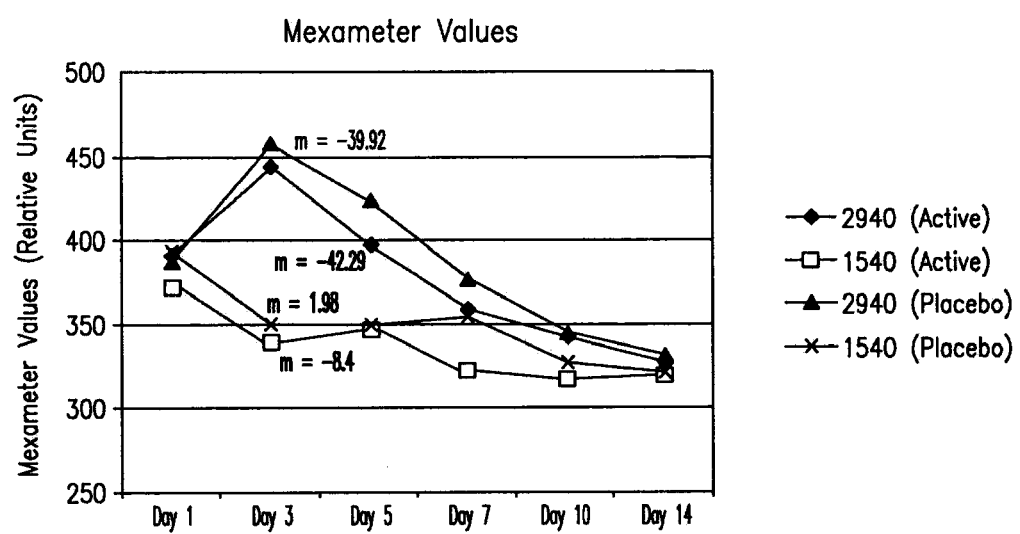
FIG. 13 is a graphical representation of mexameter analysis with data points taken at days 0, 3, 5, 7, 10 and 14 post laser surgery.

Days of petrolatum use was assessed post surgery as shown in FIG. 11. Erythema grading was conducted as shown in FIG. 12. Mexameter results are shown in FIG. 13 for both ablative (2940) and non-ablative (1540) laser settings.

The results of the studies indicated several beneficial characteristics of hECM containing topicals. Such benefits included 1) facilitating re-epithelization following resurfacing; 2) reduction of non-ablative and ablative fractional laser resurfacing symptoms (e.g., erythema, edema, crusting, and sensorial discomfort); 3) generating smooth, even textured skin; 4) generating skin moisturization; 5) reducing appearance of fine lines/wrinkles; 6) increasing skin firmness and suppleness; 7) reducing skin dyspigmentation; and 8) reducing red, blotchy skin.

EXAMPLE 10

Use of Extracellular Matrix Compositions for Stimulation of Hair Growth

This example illustrates the stimulation of hair growth by administration of ECM compositions.

Following preclinical safety and efficacy studies that indicated minimal toxic properties and suggested that the induction of anagen in telogen follicles in a murine model of hair growth might be accelerated by injection of hECM, a pilot study was undertaken to assess the activity of the preparation in man. The clinical study was a double-blind, placebo-controlled, randomized single site clinical trial, conducted in San Pedro Sula, Honduras and was primarily designed to evaluate safety in the clinical application of the hECM product. The secondary goal of the study was to evaluate clinical activity of the product or "proof of concept". Also as part of the study, whether perturbation/stimulation to the scalp prior to hECM injection would have any additive effect on hair growth was evaluated. Three different perturbation devices were chosen: 1) micro-dermabrasion (MegaPeel™, DermaMed Intl, Inc., Lenni, Pa.); 2) overlapping passes of non ablative 1540 and ablative 2940 Erbium Laser (Palomar Medical Technologies, Inc., Burlington, Mass.); and, 3) stimulation with Low Level Light Therapy by the Revage670™ (Apira Science Inc., Newport Beach, Calif.). The selected study participants were randomly assigned to one of these three perturbation methods. Two hECM preparations were evaluated in the study; a 10× concentrated, serum-free preparation, and a second, non-concentrated, bovine serum containing preparation. The presence of Wnt proteins in the hECM used in these studies was assessed by immunoblot analysis using a primary antibody recognizing the Wnt7a protein (Santa Cruz Biologicals, CA). The canonical Wnt bioactivity of hECM was confirmed by demonstrating nuclear translocation of β-catenin in human epidermal keratinocytes in vitro. LiCl was used as a positive control (data not shown), and treatment with vehicle or hECM in the presence of the Wnt receptor antagonist DKK-1 did not produce β-catenin translocation. The hECM solution also contained VEGF and KGF, as determined by ELISA.

After obtaining informed consent, 26 healthy subjects between 18-55 yrs of age were enrolled. Inclusion criteria included a Fitzpatrick score of I-IV, Norwood/Hamilton Classification for male pattern hair loss 4-6, and no history of prior hair treatments or immunological compromise. Four zones were identified as treatment sites on each subject's scalp, two anterior and two posterior. Each treatment site was marked by a tattoo on its periphery. The anterior two sites were randomized and injected with one of the two hECM preparations or placebo (unconditioned medium) with no pre-injection perturbation. The posterior treatment sites were perturbed using one of the 3 treatments mentioned above followed immediately by injection with hECM or placebo, also randomized right/left. In all patients, each site received four evenly placed intradermal 0.1 cc injections on day zero.

A combination of investigator global assessments, hair counts via macrophotography, and test subject self-assessments were performed at zero time, week 12 and week 22. In 6 patients, punch biopsies (4 mm) were performed at baseline and 48 hours after the week 22 visit and were used for histopathological evaluation. Safety outcomes were also measured through visual examination by the clinician at each time point for inflammation, redness, edema, itching, burning, swelling and any other adverse events. Global and macro photography was reviewed by independent dermatologists for any observable adverse events including redness, swelling and ingrown hairs. The biological and clinical effects of treatment were evaluated through TrichoScan macrophotographic image acquisition and analysis for anagen:telogen ratios, hair diameter, hair density, hair thickness, and vellus and nonvellus hair counts. Investigators utilized a rating system to determine visual improvement in regional hair growth.

The primary objective of the study was to assess clinical safety of hECM administration in human subjects. All patients tolerated the procedures well and no significant complaints, clinical symptoms or signs of an adverse reaction were reported in any subjects. The histopathological evaluation of the treatment site biopsies taken at 22 weeks post-treatment revealed minimal to slight inflammation at the injection site, and no abnormal morphology, hamartomas or other pathological responses were observed. From these observations, it is concluded that a single, intradermal injection of hECM did not result in any significant toxicity, pathology or other adverse event during the course of the study.

A secondary objective to assess the clinical effect of hECM on hair growth was accomplished by Trichoscan image analysis. Results are expressed as group means±SEM unless otherwise noted. The equivalence of treatment sites at day zero prior to manipulation was determined using a one-way ANOVA. Subsequent differences between group means within a treatment group at day 0, 12 and 22 weeks post-treatment were evaluated using paired (repeated-measures), two-tailed Student's t-tests. All other differences between group means were evaluated using unpaired, two-tailed Student's t-test. Statistical significance was set at level of $\alpha=0.05$. A comparison of the day 0, pretreatment group means of the hair growth indicator measurements between the untreated and treated designated sites noted no statistically significant differences. Any subsequent differences in growth at 12 or 22 weeks post-administration could therefore be inferred as a result of experimental treatment.

Figure 27:
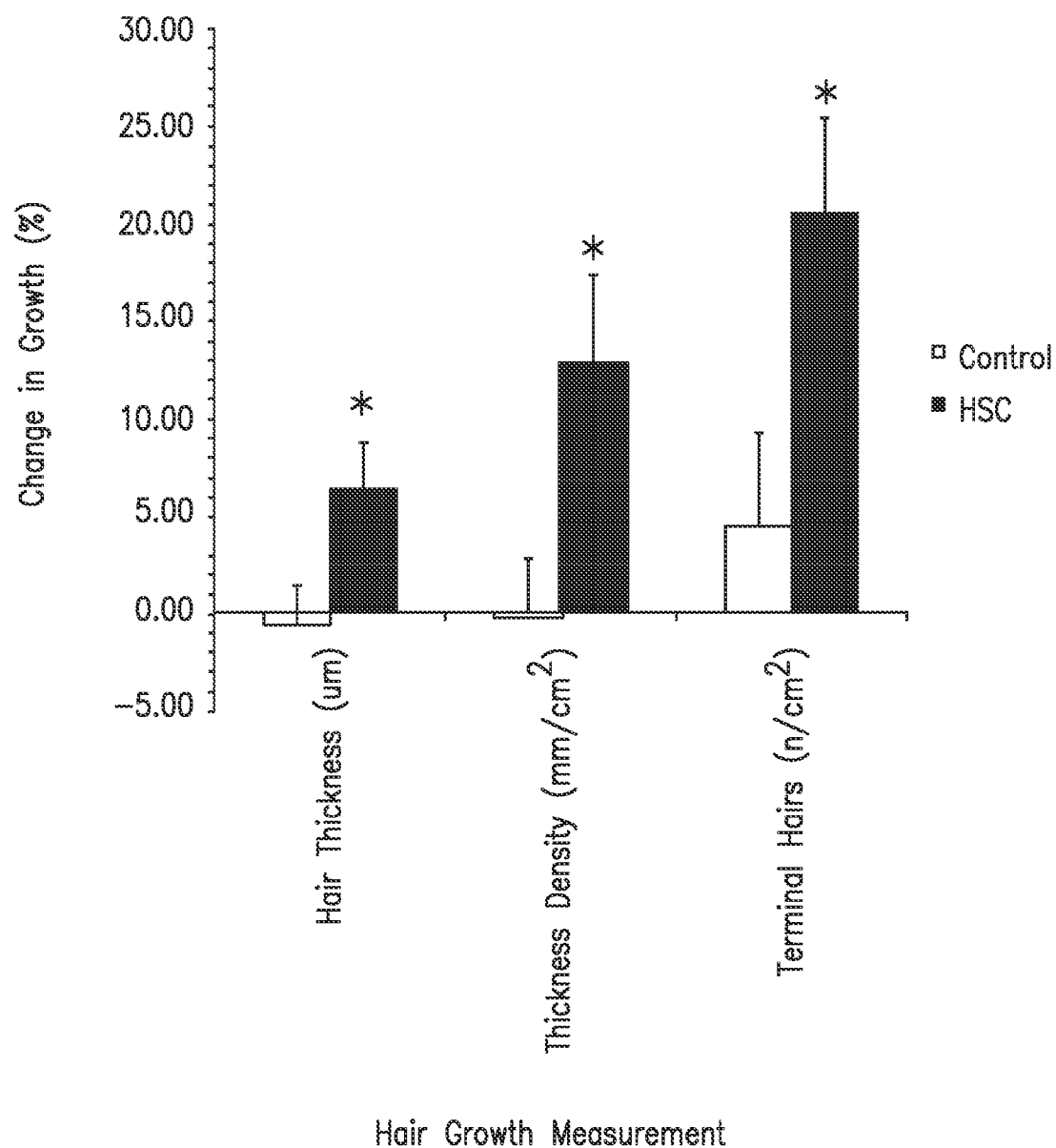
FIG. 27 shows a graphical representation of hair growth measurement.

Trichoscan image analysis of placebo treated sites (n=12) at 12 and 22 weeks showed no significant improvements in any of the measured hair growth indicators. In addition, no significant effects were seen with the serum containing hECM preparation. However, over the initial 12 week evaluation period, the higher concentration, serum-free hECM formulation treated sites (n=13) demonstrated an increase in all hair growth indicators with the exception of vellus hair density, which remained unchanged over the course of the study (FIGS. 1D, E). Perturbation prior to the administration of hECM did not result in an enhancement in growth from that of the serum-free hECM administration alone. At 12 weeks, a statistically significant increase from Day 0 values in the hair shaft thickness ($p<0.05$), hair thickness density ($p<0.05$) and the number of nonvellus, terminal hairs ($p<0.005$) was observed in the hECM treated sites (FIG. 27). The improvements caused by hECM treatment were significantly greater than that observed in placebo treated sites hair shaft thickness (6.3%±2.5% vs. −0.63%±2.1%; $p<0.05$), thickness density (12.8%±4.5% vs. −0.2%±2.9%; $p<0.05$), and terminal hair density (20.6±4.9% vs. 4.4±4.9%; $p<0.05$). One subject showed a 22.4% increase in total hair count and a 27.8% increase in terminal hairs at three months following a single injection of hECM. Although a similar trend was seen at 22 weeks, significance was lost as there was no further growth improvement in the subjects. These results clearly demonstrate that a single intradermal administration of hECM significantly improved hair growth in subjects with androgenetic alopecia.

This first-in-man clinical study demonstrates the safety of the fibroblast-secreted hECM protein preparation and indicates initial efficacy in hair restoration. The hECM proteins produced by the fibroblasts grown under hypoxic conditions include factors that are important in the hair cycle regulation. In terms of cell lineage, fibroblasts are the parent cells of the hair papilla cells. In studies in vitro the presence of Wnt proteins, VEGF, FGF, KGF and also follistatin have been determined. The role of Wnt proteins is established to be important in the hair follicle, playing a crucial role in the initiation of hair growth. In addition, Wnt activity is important in the hair cycle, initiating in the later stages of telogen the activation of cells and gene expression required for the formation of a hair germ from keratinocytes that will commence the next anagen stage of hair growth. Therefore, it is expected that the stimulation of hair regrowth induced by the delivery of hECM is due, at least in part, to Wnt activity.

The efficacy results seen with a single injection of hECM represent a novel approach in hair growth treatment. FDA approved products, minoxidil (e.g., Rogaine™) and finasteride (e.g., Propecia™), require daily use of the therapeutic to induce and maintain efficacy. Specifically, these products show their greatest efficacy in reducing loss of hair, with a small percentage of new hair growth seen after at least four months of daily use. In contrast, a single injection of hECM resulted in a statistically significant growth of new terminal hairs and an increase in hair density and thickness. The mechanism(s) responsible for hair growth have been studied for over a decade as researchers have demonstrated the underlying importance of Wnt proteins and wound growth factors in stimulating dermal papilla-associated stem cells. This clinical pilot study is the first demonstration that a preparation containing Wnt proteins and wound growth factors has a biologically active stimulatory affect on new hair induction in humans.

EXAMPLE 11

Fabrication of Compliant Polyethylene Terephthalate Prosthesis Coated with Embryonic ECM Current clinically available synthetic vascular grafts such as Polyethylene Terephthalate (PET) frequently fail when used for small-diameter vascular substitution due to thrombosis and intimal hyperplasia. The failure is attributed to the lack of a confluent endothelial monolayer and a compliance mismatch between the vascular graft and surrounding tissue. A biomechanically compliant small diameter (1.5 mm) non-woven PET fiber structure was fabricated including human Extracellular Matrix (hECM) developed under embryonic conditions and including proteins mimicking the properties of natural blood vessel ECM. The hECM proteins were coated on the nonwoven PET fiber structure through dip coating and covalent surface amino grafting poly(vinyl amine) (PVA) methods, to address the primary causes of graft failure. The hECM proteins were not crosslinked to PET allowing RGD and CS5 surface exposure as cell-binding domains for endothelial cells. Previous works have shown that hECM dip coated polypropylene polymers abased the inflammatory reaction when implanted in rats. Also, in previous studies we optimized the nonwoven PET fiber scaffold diameter and pore size for Endothelial (EC) and Smooth Muscle (SMC) cells growth, phenotype, and retention under shear-stress conditions as well as the nonwoven PET fiber structures mechanical behavior mimicking small-diameter aorta. This study examines the hECM coating bonding, dosage and uniformity on the PET scaffolds.

The following methods were utilized. Neat PET (Dupont, Wilmington, Del.), was used to produce nonwoven PET fibers using the melt-blowing process with an average 50 μm fiber diameter, and the juxtaposition of individual PET fiber layers (0°/90°) was used to fabricate the 3D structure. The hECM was prepared under embryonic conditions hECM by culturing neonatal dermal fibroblasts on dextran microspheres in a stirred bioreactor for eight weeks. The first four weeks in 10% bovine calf serum containing medium then weaned to a serum free medium formulation. The addition of hECM on the nonwoven PET vascular scaffolds was performed by amino-modifying the PET fibers by: 0.1M NaOH, 0.1M KCl, 750 mM PVA-HCl (Polysciences, USA), 400 μl 1,4-diaxone; followed by sonication, and 24 h heat treatment. Reagents were purchased from Sigma Aldrich, Canada unless stated otherwise. The nonwoven PET fiber structures (aminated and untreated) were then immersed into hECM (0.1 mg/ml to 0.6 mg/ml diluted in PBS) overnight at 4° C. To reduce non covalent bonding the samples were washed 3× into PBS under 10 min sonication cycles. The hECM coverage of the nonwoven PET fiber structures was chemically characterized by: 1) Fourier Transformed Infrared (FTIR) spectroscopy, 2) Scanning Electron Microscopy (SEM) and energy dispersive (EDX) spectra for localized chemical identification, 3) hydrophilicity by water drop method (Video Contact Angle 2000) and 4) X-ray photoelectron spectroscopy (XPS). The hECM coating was also visualized by fluorescently binding Rhodamine B isothiocyanate (RBITC) to hECM on a confocal microscope (LSCM, Leica, Germany). The dosage of the hECM coating was quantified by trypsining the hECM coating and quantifying it via micro BCA protein assay (Pierce Chemical Co, IL).

Figure 28:
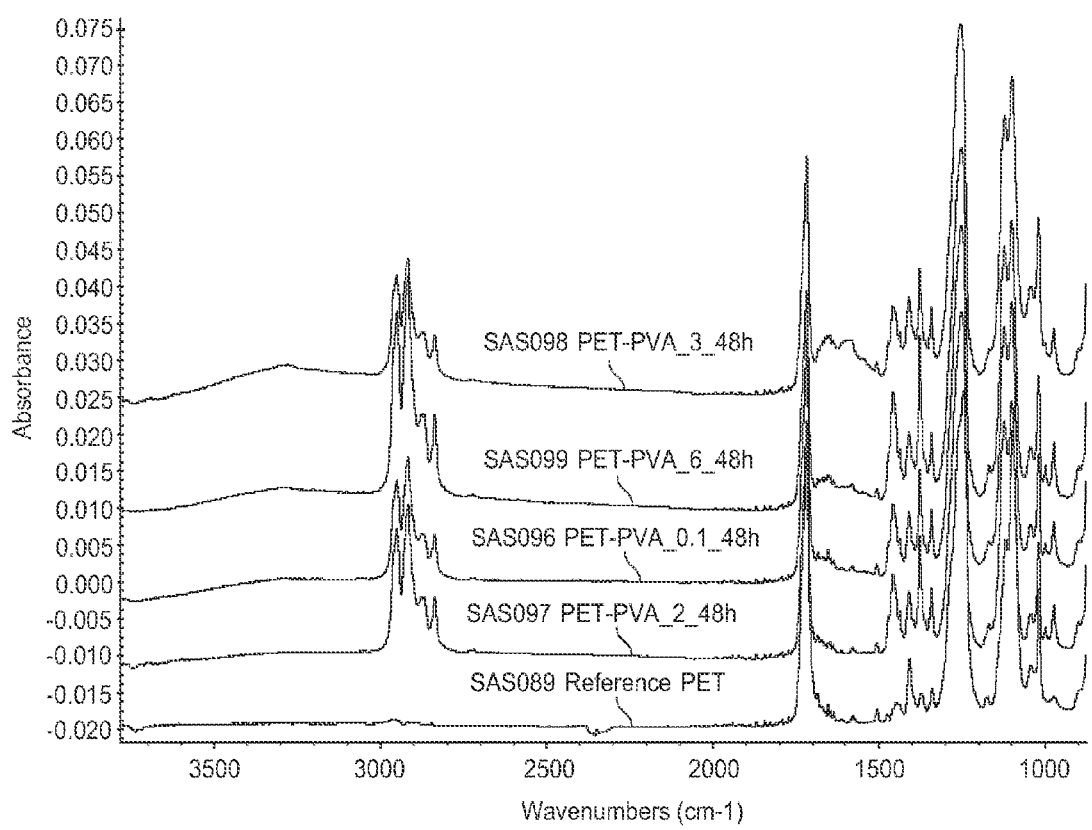
FIG. 28 shows a graphical representation of Fourier Transformed Infrared (FTIR) spectroscopy.

The FTIR study demonstrated the appearance of three major peaks arising from the increasing concentration of the hECM coating on the aminated nonwoven PET fibers: the 1522 cm$^{-1}$ (Amide II sN—H and mC—N), 1656 cm$^{-1}$ (Amide I, sC=O) and 3320 cm$^{-1}$ (sNH) bands (FIG. 28). The FTIR results suggest highest hECM coverage of the aminated PET fibers succeeds with the 0.6 mg/ml hECM solution. The opposite trend was seen with non aminated PET fibers where small hECM peaks only appeared at low hECM concentrations (0.1 mg/ml to 0.2 mg/ml).

The SEM and RBITC fluorescence photomicrographs demonstrated a homogenous hECM coverage (hECM is clearly observed on PET surface), with the highest hECM concentration (0.6 mg/ml) on aminated PET fibbers, supporting the FTIR trend. On the other hand, the low hECM concentrations (up to 0.2 mg/ml) adhered best on untreated PET fibers, as seen with FTIR. The Micro BSA assay revealed at least 2 times higher hECM retention on aminated as compared to the non treated PET fibers (0.1 mg/cm$^2$ and 0.04 mg/cm$^2$ respectively). Lastly the contact angle of PET (75°), decreased with PET amination (45°) further decreasing to 32° with the immobilization of 0.6 mg/ml hECM.

Coating of hECM on PVA aminated nonwoven vascular PET fiber structures demonstrated a high density hECM coating method without crosslinking cell-binding hECM domains to the PET structure.

EXAMPLE 12

Embryonic ECM Coated on Small Diameter Vascular Grafts

The retention of Human Aortic Endothelial Cells (HAoEC) on noncoated and hECM-coated PET vascular scaffolds was assessed after exposure to pulsatile flow shear stress in a flow circuit reproducing femoral artery and venous flow waveforms and pulsatility.

Nonwoven PET fibers scaffolds were produced by the melt-blowing process. Functionalization of PET fibers with hECM was performed using poly(vinyl amine). HAoEC were seeded ($2.0 \times 10^5$/cm$^2$) on both noncoated and hECM-coated PET vascular scaffolds and statically co-incubated for 3 days before transfer to vascular rheometer simulating physiological pulsatile-flow waveform under arterial (shear rate of 300 s-1) and venous (shear rate of 100 s-1) flow conditions. Following incubation, the cellular retention was characterized by SEM observations, Alamar Blue viability assay and fluorescent HAoEC visualization through Alexa Fluor 488 (F-actin) labeling.

A substantial reduction in cell loss was observed in the hECM-coated PET vascular scaffolds when compared to the noncoated PET vascular scaffolds, following both arterial and venous shear stress conditions. The cell number retained on the hECM-coated PET vascular scaffold was 3× higher (retention rate ~85%) than in uncoated ones after 1 h of flow under arterial rates. Similar results of significantly higher HAoEC retention on hECM-coated grafts were observed after 1 h of flow under arterial rates. This trend of higher cellular retention on hECM-coated PET vascular scaffolds after arterial and venous shear-stress conditions was also confirmed by the 3-fold increase in both metabolic activity (measured by Alamar Blue cell viability assay) and number of cells (counted on SEM photomicrographs) obtained in these scaffolds.

Functionalization of PET small-diameter (1.5 mm) grafts with a high density hECM coating method without crosslinking the RGD-binding domains efficiently enhanced the resistance of HAoEC to physiologically simulated in vitro shear forces.

EXAMPLE 13

Coating Polymers with hECM Significantly Improves Biocompatibility

Human ECM generated under embryonic conditions was used to coat to polymeric scaffolds and tested in vivo or biocompatibility. The hECM was generated by neonatal dermal fibroblasts grown on dextran microspheres grown in a stirred bioreactor. Nylon, polyprolene (PPE), and polyethylene terephthalate (PET) nonwoven scaffolds were ECM coated. The hECM was coupled to the polymeric scaffolds using: Glutaraldehyde, "dip & dry", UVA, Acetic acid etch, poly(vinyl amine) (PVA) and Sulfo Sanphah. The various hECM-coatings were characterized using: Fourier Transformed Infrared (FTIR) and energy dispersive (EDX) spectra and visualized using Scanning Electron Microscopy (SEM) and immunofluorescence. The best ECM-coated and uncoated scaffolds were then surgically implanted in the subcutaneous space of SCID mice. The histological samples of excised implants were assessed for inflammatory response, cellular infiltration, foreign body giant cells and capsule formation.

The FTIR results suggest highest ECM coverage via the PVA and UVA techniques from ECM solution of 0.6 mg/ml. The high ECM solution density suggests complete polymeric coverage with ECM via the polymeric surface activated amine groups. A complete ECM coverage was desired as to "hide" the polymer from the physiological environment. This trend was confirmed by the SEM and fluorescence micrographs where homogenous and dense ECM coverage was seen.

Human aortic endothelial cells (HAoEC) seeded to ECM-coated and uncoated scaffolds were assayed for cellular proliferation with the Alamar Blue assay. Typically the materials that demonstrated the highest ECM coverage (under FTIR and SEM) also bound cells more efficiently and supported two-fold increase in cellular proliferation.

Lastly, the subcutaneously implanted ECM-coated (PET, PPE and nylon polymeric scaffolds) demonstrated a significant reduction in immune cell infiltration and foreign body giant cell formation when compared to uncoated scaffolds. Additionally, improved collagen capsule formation and tissue integration was observed with the ECM coated various polymers when compared with their uncoated controls.

Although the invention has been described with reference to the above examples, it will be understood that modifications and variations are encompassed within the spirit and scope of the invention. Accordingly, the invention is limited only by the following claims.

What is claimed is:

1. A method of producing a soluble composition for promoting hair growth in a human subject comprising:
    culturing fibroblast cells under hypoxic conditions on a microcarrier bead or three dimensional surface in a suitable growth medium, under 1-5% oxygen for at least 2 weeks, thereby producing multipotent stem cells, wherein the multipotent stem cells produce and secrete a soluble composition that promotes hair growth when administered to the hair follicles of a subject, resulting in increased hair growth; and
    collecting the growth medium after said 2 weeks.

2. A method of producing a soluble composition for promoting hair growth in a human subject comprising:
    culturing fibroblast cells under hypoxic conditions on a microcarrier bead or three dimensional surface in a suitable growth medium, under 1-5% oxygen for at least 2 weeks, wherein the cells produce and secrete a soluble composition that promotes hair growth when administered to the hair follicles of a subject, resulting in increased hair growth; and
    collecting the growth medium after said two weeks.

3. The method of claim 1 or 2, wherein the soluble composition produced is formulated for administration to a hair follicle.

4. The method of claim 3, wherein the composition is further formulated for administration to a cell in vivo.

5. The method of claim 3, wherein the further formulated for administration to a cell ex vivo.

6. The method of claim 3, wherein the hair follicle is transplanted into a subject.

7. The method of claim 1 or 2, wherein the surface comprises mesh.

8. The method of claim 1 or 2, wherein the growth medium comprises serum.

9. The method of claim 1 or 2, wherein the growth medium is serum-free.

10. The method of claim 1 or 2, wherein the composition is suitable for intradermal or topical administration.

11. A method of promoting hair growth in a subject comprising:
    administering directly to hair follicles of a human subject a composition produced by culturing fibroblast cells under hypoxic conditions on a microcarrier bead in a suitable growth medium, under 1-5% oxygen for at least 2 weeks, thereby producing multipotent stem cells, wherein the multipotent stem cells produce and secrete a soluble composition that promotes hair growth when administered to the hair follicles of a subject, resulting in increased hair growth, and wherein the growth medium after said 2 weeks is collected to obtain the soluble composition containing increased levels of VEGF and KGF as compared with a composition from cells grown under normoxic conditions, thereby promoting hair growth in the subject.

12. A method of promoting hair growth in a subject comprising:
    administering directly to hair follicles of a human subject a composition produced by culturing fibroblast cells under hypoxic conditions on a microcarrier bead in a suitable growth medium, under 1-5% oxygen for at least 2 weeks, wherein the cells produce and secrete a soluble composition that promotes hair growth when administered to the hair follicles of a subject, resulting in increased hair growth, and wherein the growth medium is collected after said two weeks to obtain the soluble composition containing increased levels of VEGF and KGF as compared with a composition from cells grown under normoxic conditions, whereby hair growth is promoted.

13. The method of claim 11 or 12, wherein the contacting is by intradermal or topical administration.

14. The method of claim 11 or 12, wherein the cultured cells are neonatal fibroblast cells.

15. The method of claim 1 or 11, wherein the soluble composition comprises hair growth stimulating effective amounts of at least one or more of Wnt proteins, VEGF, FGF, KGF, follistatin and a combination thereof.

16. The method of claim 15, wherein the Wnt proteins, VEGF, KGF, FGF and follistatin are upregulated as compared with soluble compositions produced in oxygen conditions of about 15-20% oxygen.

17. The method of claim 3 or 11, wherein the composition is formulated for injectable administration.

* * * * *